(12) United States Patent
Kondo

(10) Patent No.: US 9,675,693 B2
(45) Date of Patent: Jun. 13, 2017

(54) METHODS AND DRUGS TARGETING EVA1 OR CEACAM1 GENE EXPRESSION FOR TREATMENT AND DIAGNOSING OF GLIOMA

(75) Inventor: Toru Kondo, Kobe (JP)

(73) Assignee: RIKEN, Wako-shi, Saitama (JP)

( * ) Notice: Subject to any disclaimer, the term of this patent is extended or adjusted under 35 U.S.C. 154(b) by 0 days.

(21) Appl. No.: 13/877,023

(22) PCT Filed: Sep. 29, 2011

(86) PCT No.: PCT/JP2011/072428
§ 371 (c)(1),
(2), (4) Date: May 16, 2013

(87) PCT Pub. No.: WO2012/043747
PCT Pub. Date: Apr. 5, 2012

(65) Prior Publication Data
US 2013/0224208 A1  Aug. 29, 2013

(30) Foreign Application Priority Data

Sep. 30, 2010 (JP) ................................ 2010-222832
Jun. 29, 2011 (JP) ................................ 2011-144115

(51) Int. Cl.
| | | |
|---|---|---|
| A61K 39/44 | (2006.01) | |
| A61K 39/395 | (2006.01) | |
| C07K 16/30 | (2006.01) | |
| A61K 31/542 | (2006.01) | |
| A61K 31/7105 | (2006.01) | |
| G01N 33/68 | (2006.01) | |
| C07K 16/28 | (2006.01) | |
| A61K 39/00 | (2006.01) | |

(52) U.S. Cl.
CPC ...... *A61K 39/39558* (2013.01); *A61K 31/542* (2013.01); *A61K 31/7105* (2013.01); *C07K 16/28* (2013.01); *C07K 16/2803* (2013.01); *C07K 16/3053* (2013.01); *G01N 33/6893* (2013.01); *A61K 2039/505* (2013.01); *C07K 2317/34* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,558,852 A * | 9/1996 | Bigner et al. ............... | 424/1.49 |
| 2007/0178458 A1 | 8/2007 | O'Brien et al. | |
| 2007/0293416 A1 | 12/2007 | Markel | |
| 2009/0163434 A1 | 6/2009 | Bader et al. | |
| 2009/0191225 A1 | 7/2009 | Chang et al. | |
| 2009/0227533 A1 | 9/2009 | Bader et al. | |
| 2013/0287772 A1 | 10/2013 | Halbert et al. | |

FOREIGN PATENT DOCUMENTS

| | | |
|---|---|---|
| JP | 2009-232705 A | 10/2009 |
| JP | 2010-529966 A | 9/2010 |
| WO | 2005024055 | 3/2005 |
| WO | 2005113812 | 12/2005 |
| WO | 2008/073919 A2 | 6/2008 |
| WO | WO2009/045443 * | 4/2009 |
| WO | 2009/126558 A1 | 10/2009 |
| WO | 2011109440 | 9/2011 |

OTHER PUBLICATIONS

Carter (Experimental Cell Research, vol. 317, p. 1261-1269, 2011).*
Jones (Pharmaceutical Research, vol. 24, No. 9, p. 1759-1771, 2007).*
Eck and Wilson, Goodman & Gilman's The Pharmacological basis of Therapeutics, 1996, McGraw-Hill, New York, NY. p. 77-101.*
Niidome and Huang (Gene Therapy, 2002, 9:1647-1652).*
Zhang et al (Molecular Therapy, 2012, 20:1298-1304).*
Gao et al (The AAPS Journal, 2007, 9:E92-E104).*
Parker et al (Expert Reviews in Molecular Medicine, 2003, 5:1-15).*
Verma and Somia (Nature, 1997, 389:239-242).*
International Preliminary Report on Patentability for PCT/JP2011/072428 dated Apr. 30, 2013, along with the Written Opinion.
Matsuno et al., "Specific gene suppression using antisense strategy for growth suppression of glioma", Medical Electron Microscopy, 37(3):158-161 (2004).
Tilki et al., "One molecule, two faces: Epithelial loss of cell adhesion molecule CEACAM1 activates angiogenesis in bladder and prostate cancer", Der Urolge, Ausgabe A; Zeitschrift Für Klinische and Praktische urologie Organ der Deutschen Gesellschaft für urologie, 46(9):1128-1134 (2007).
Lacovelli et al., "Lymphoid EVA1 Expression is required for DN1-DN3 Thymocytes Transition", PLOS One, 4(10):e7586, pp. 1-7 (2009).
Singer et al., "Carcinoembryonic antigen-related cell adhesion molecule 1 expression and signalizing in human, mouse and rat leukocytes: Evidence for replacement of the short cytoplasmic domain isoform by glycosylphosphatidylinositol-linked protein in human leukocytes", The Journal of Immunology, 168(10):5139-5146 (2002).
Communication for EP Application No. 11 82 9300.0 dated Apr. 24, 2014, with Supplementary European Search Report dated (Apr. 14, 2014), International Preliminary Report on Patentability (dated Apr. 9, 2013) and Written Opinion (dated Oct. 25, 2011).

(Continued)

*Primary Examiner* — Michael D Allen
(74) *Attorney, Agent, or Firm* — Sughrue Mion, PLLC

(57) ABSTRACT

An object is to provide glioma treatment and testing methods, and a method for delivering a desired substance to a glioma, all of which target a molecule specifically expressed in a glioma, as well as drugs and so forth used in these methods. It has been found out that targeting Eva1 or Ceacam1 enables glioma treatment and testing, and delivering of a desired substance to a glioma.

1 Claim, 35 Drawing Sheets

(56) References Cited

OTHER PUBLICATIONS

Alireza Ebrahimnejad et al., "CEACAM1 Enhances Invasion and Migration of Melanocytic and Melanoma Cells", American Journal of Pathology, Nov. 2004, pp. 1781-1787, vol. 165, No. 5.

Diane M. Simeone et al., "CEACAM1, a Novel Serum Biomarker for Pancreatic Cancer", Pancreas, May 2007, pp. 436-443, vol. 34, No. 4.

Peter Kletting et al., "Radioimmunotherapy with Anti-CD66 Antibody: Improving the Biodistribution Using a Physiologically Based Pharmacokinetic Model", The Journal of Nuclear Medicine, Mar. 2010, pp. 484-491, vol. 51, No. 3.

Barbara Jarzab et al., "Gene Expression Profile of Papillary Thyroid Cancer: Sources of Variability and Diagnostic Implications", Cancer Research, Feb. 2005, pp. 1587-1597, vol. 65, No. 4.

Maria Guttinger et al., "Epithelial V-like Antigen (EVA), a Novel Member of the Immunoglobulin Superfamily, Expressed in Embryonic Epithelia with a Potential Role as Homotypic Adhesion Molecule in Thymus Histogenesis", The Journal of Cell Biology, May 1998, pp. 1061-1071, vol. 141, No. 4.

S. Difilippantonio et al., "Gene expression profiles in human non-small and small-cell lung cancers", European Journal of Cancer 39, 2003, pp. 1936-1947.

Piyush B. Gupta et al., "Identification of Selective Inhibitors of Cancer Stem Cells by High-Throughput Screening", Cell 138, Aug. 2009, pp. 645-659.

Thiruvengadam Arumugam et al., "Epithelial to Mesenchymal Transition Contributes to Drug Resistance in Pancreatic Cancer", Cancer Res Jul. 2009, pp. 5820-5828, vol. 69, No. 14.

Katharina Kuespert et al., "CEACAMs: their role in physiology and pathophysiology", Current Opinion in Cell Biology 2006, pp. 565-571, vol. 18.

Scott D. Gray-Owen et al., "CEACAM1: contact-dependent control of immunity", Nature Reviews Immunology, Jun. 2006, pp. 433-446, vol. 6.

Maria Huber et al., "The Carboxyl-terminal Region of Biliary Glycoprotein Controls Its Tyrosine Phosphorylation and Association with Protein-tyrosine Phosphatases SHP-1 and SHP-2 in Epithelial Cells", The Journal of Biological Chemistry, Jan. 1999, pp. 335-344, vol. 274, No. 1.

Thomas R. Barnett et al., "Carcinoembryonic Antigens: Alternative Splicing Accounts for the Multiple mRNAs that Code for Novel Members of the Carcinoembryonic Antigen Family", The Journal of Cell Biology, Feb. 1989, pp. 267-276, vol. 108.

Luo Wang et al., "C-CAM1, a Candidate Tumor Suppressor Gene, is Abnormally Expressed in Primary Lung Cancers", Clinical Cancer Research 2000, pp. 2988-2993, vol. 6.

W. Liu et al., "CEACAM1 impedes thyroid cancer growth but promotes invasiveness: a putative mechanism for early metastases", Oncogene 2007, pp. 2747-2758, vol. 26.

Shikha Gaur et al., "Altered splicing of CEACAM1 in breast cancer: Identification of regulatory sequences that control splicing of CEACAM1 into long or short cytoplasmic domain isoforms", Molecular Cancer 2008, 12 pgs., vol. 7, No. 46.

International Search Report for PCT/JP2011/072428 dated Oct. 25, 2011.

* cited by examiner

Fig. 1

```
hEval   1   MYGKSSTRAVLLLLGIQLTALWPIAAVEIYTSRVLEAVNGTDARLKCTFS    50
mEval   1   MYGKSPALVLPLLSLQLTALCPTEAVEIYTSGALEAVNGTDVRLKCTFS    50 hEval  51   SFAPVGDALTVTWNFRPLDGGPEQFVFYHIDPFQPMSGRFKDRVSWDGN   100
mEval  51   SFAPVGDALTVTWNFRPRDGGREQFVFYHMDPFRPMSGRFKDRVVWDGN   100 hEval 101   PERYDASILLWKLQFDDNGTYTCQVKNPPDVDGVIGEIRLSVVHTVRFSE  150
mEval 101   PERYDVSILLWKLQFDDNGTYTCQVKNPPDVDGLVGTIRLSVVHTVPFSE  150 hEval 151   IHFLALAIGSACALMIIIVIVVVLFQHYRKKRWAERAHKVVEIKSKEEER  200
mEval 151   IYFLAVAIGSACALMIVVIVVVLFQHFRKKRWADRADKAEGTKSKEEEK  200 hEval 201   LNQEKKVSVYLEDTD    215
mEval 201   LNQGNKVSVFVEDTD    215
```

METHODS AND DRUGS TARGETING EVA1 OR CEACAM1 GENE EXPRESSION FOR TREATMENT AND DIAGNOSING OF GLIOMA

CROSS REFERENCE TO RELATED APPLICATIONS

This application is a National Stage of International Application No. PCT/JP2011/072428 filed Sep. 29, 2011, claiming priority based on Japanese Patent Application Nos. 2010-222832 filed Sep. 30, 2010 and 2011-144115 filed Jun. 29, 2011, the contents of all of which are incorporated herein by reference in their entirety.

TECHNICAL FIELD

The present invention relates to a glioma treatment method, a glioma testing method, a method for delivering a desired substance to a glioma, and drugs used in these methods. More specifically, the pre sent invention relates to glioma treatment and testing methods, and a method for delivering a desired substance to a glioma, all of which target Eva1 and/or Ceacam1. Further, the present invention relates to drugs used in these methods.

BACKGROUND ART

A glioma is a collective term for tumors arising from neural stem cells, neural precursor cells, and neuroglial cells (glial cells). Gliomas account for approximately 25% of primary brain tumors in Japan, and are representative of malignant brain tumors. Moreover, gliomas are classified into astrocytic tumor, oligodendroglial tumor, oligoastrocytic tumor, ependymal tumor, and the like according to cells from which the gliomas are originated. Furthermore, gliomas are evaluated by grades from 1 to 4 according to the clinical malignancy established by WHO. Incidentally, grade 4 tumors are the most malignant and the prognosis is the worst, and particularly tumors of grades 3 and 4 are called malignant gliomas.

The treatment of the malignant gliomas is based on a surgery with adjuvant therapy of radiation therapy and chemotherapy, but has not changed much for several decades. Particularly, no effective treatment method for the most malignant glioblastoma multiforme (GBM) of malignant gliomas of central nervous system tissues has been found.

For this reason, searching is in progress for novel molecules, which could be targets of treatment and diagnosis for gliomas. So far, there has been reported, for example, that a DBCCR1L gene is specifically expressed in a glioma derived from oligodendrocytes (PTL 1).

Meanwhile, a single-pass transmembrane-type cell membrane protein Eva1 (epithelial V-like antigen, also called MPZL2) is a molecule involved in a cytoskeletal system, and is known to be expressed in a thymus and the like. Moreover, it has been reported that this protein is expressed in small-cell carcinoma (SCC), metastatic small-cell lung carcinoma (SCLC), pancreatic cancer, papillary thyroid cancer, and so on (NPLs 1 to 4).

However, no report has been made regarding a relation between Eva1 and gliomas at all.

Moreover, Ceacam1 (CARCINOEMBRYONIC ANTI-GEN-RELATED CELL ADHESION MOLECULE 1) is a member of the carcinoembryonic antigen (CEA) family, and is known to regulate cell adhesion via homotypic binding and heterotypic binding to other CEA proteins. Further, Ceacam1 is believed to be involved in cell proliferation, inhibition of the cytotoxicity of immune cells, VEGF-induced angiogenesis, apoptosis, metastasis, as well as regulation of innate immune response and adaptive immune response (NPLs 5 and 6).

Furthermore, it has been shown that Ceacam1-L, one of splicing variants of Ceacam1, encodes an immunoreceptor tyrosine-based inhibitory motif at the cytoplasmic tails and demonstrates a tumor-suppressing activity based on this motif (NPLs 5 to 7). Meanwhile, there is also a report that the expression of Ceacam1-L is promoted in lung, colorectal, and thyroid cancers (NPLs 8 to 11).

As described above, it is not clearly understood what function Ceacam1 demonstrates in lung cancer and the like. Particularly, the association with gliomas has not been analyzed sufficiently until now.

CITATION LIST

Patent Literature

[PTL 1] Japanese Unexamined Patent Application Publication No. 2009-232705

Non Patent Literatures

[NPL 1] Difilippantonio, et al., Eur. J. Cancer, 2003, col. 39, pp. 1936 to 1947
[NPL 2] Piyush, et al., Cell, 2009, vol. 138, pp. 645 to 659
[NPL 3] Arumugam, et al., Cancer Res., 2009, vol. 69, no. 14, pp. 5820 to 5828
[NPL 4] Jarzab, et al., Cancer Res., 2005, vol. 65, no. 4, pp. 1587 to 1597
[NPL 5] Kuespert, K., et al., Curr. Opin. Cell Biol. 2006, vol. 18, pp. 565 to 571
[NPL 6] Gray-Owen, S. D., et al, Nat. Rev. Immunol. 2006, vol. 6, pp. 433 to 446
[NPL 7] Huber, M., et al., J. Biol. Chem., 1999, vol. 274, pp. 335 to 344
[NPL 8] Barnett, T. R., et al., J. Cell Biol. 1989, vol. 108, pp. 267 to 276
[NPL 9] Wang, L., et al., Clin. Cancer Res., 2000, vol. 6, pp. 2988 to 2993
[NPL 10] Liu, W., et al., Oncogene, 2007, vol. 26, pp. 2747 to 2758
[NPL 11] Gaur, S., et al., Mol. Cancer, 2008, vol. 7, 46

SUMMARY OF INVENTION

Technical Problem

The present invention has been made in view of such circumstances. An object of the present invention is to find molecules specifically expressed in a glioma, and to provide glioma treatment and testing methods, and a method for delivering a desired substance to a glioma, all of which target the molecule, as well as drugs and so forth used in these methods.

Solution to Problem

The present inventor has earnestly studied to achieve the above object. As a result, the inventor has found out that an Eva1 gene is specifically expressed in a glioma, and that molecules (an anti-Eva1 protein antibody, a peptide having a dominant-negative phenotype against an Eva1 protein, an RNA capable of binding to a transcription product of the Eva1 gene) capable of suppressing the function of the Eva1 gene are able to suppress the growth potential, tumor-forming potential, and tissue invading potential of glioma cells as well as the tumor mass-forming potential of glioma stem cells. Moreover, the present inventor has found out that it is possible to deliver a desired substance to glioma stem cells by use of the anti-Eva1 protein antibody. Further, the present inventor has found out through the research using a brain tumor database that there is a high correlation between the survival rate of glioma patients and the expression of the Eva1 gene in the gliomas derived from the patients.

In addition, the present inventor has found out that expression patterns of a large number of genes are changed by suppressing the expression of Eva1 in glioma stem cells. Furthermore, the inventor has earnestly studied focusing on the observation on a Ceacam1 gene whose expression is significantly reduced by suppressing the Eva1 expression. This result has revealed that Ceacam1 is not expressed in normal brain tissues but is expressed at high level in glioma stem cells and gliomas (mainly GBM). Furthermore, through the research using the brain tumor database, a high correlation has been found out between the survival rate of the glioma patients and the expression of the Ceacam1 gene in the gliomas derived from the patients. Additionally, the present inventor has also revealed that the malignancy of glioma stem cells is promoted by enhancing the expression of Ceacam1-L, while the malignancy of gliomas is reduced by suppressing the expression of Ceacam1.

Based on these findings, the present inventor has found out that targeting Eva1 or Ceacam1 enables glioma treatment and testing, and delivering of a desired substance to a glioma. These discoveries have led to the completion of the present invention.

More specifically, the present invention provides the following inventions.

(1) A glioma treatment method comprising suppressing a function of at least any one gene of an Eva1 gene and a Ceacam1 gene in a subject.
(2) A glioma therapeutic drug comprising, as an active ingredient, a molecule capable of suppressing a function of at least any one gene of an Eva1 gene and a Ceacam1 gene.
(3) The therapeutic drug according to (2), wherein the molecule capable of suppressing a function of at least any one gene of an Eva1 gene and a Ceacam1 gene is any one of the following molecules (a) to (f):
 (a) an anti-Eva1 protein antibody;
 (b) a peptide having a dominant-negative phenotype against an Eva1 protein;
 (c) an RNA capable of binding to a transcription product of the Eva1 gene;
 (d) an anti-Ceacam1 protein antibody;
 (e) a peptide having a dominant-negative phenotype against a Ceacam1 protein; and
 (f) an RNA capable of binding to a transcription product of the Ceacam1 gene.
(4) A glioma testing method comprising detecting an expression of at least any one gene of an Eva1 gene and a Ceacam1 gene in a subject.
(5) A glioma testing drug comprising, as an active ingredient, a molecule capable of binding to an expression product of at least any one gene of an Eva1 gene and a Ceacam1 gene.
(6) The testing drug according to (5), wherein the active ingredient is at least any one antibody of an anti-Eva1 protein antibody and an anti-Ceacam1 protein antibody.

(7) A method for delivering a desired substance to a glioma in a subject, the method comprising administering, to the subject, at least any one antibody of an anti-Eva1 protein antibody to which the desired substance binds and an anti-Ceacam1 protein antibody to which the desired substance binds.
(8) A drug for delivering a desired substance to a glioma in a subject, the drug comprising, as an active ingredient, at least any one antibody of an anti-Eva1 protein antibody and an anti-Ceacam1 protein antibody.

Advantageous Effects of Invention

According to the present invention, targeting Eva1 or Ceacam1 enables glioma treatment and testing, and delivering of a desired substance to a glioma.

BRIEF DESCRIPTION OF DRAWINGS

FIG. 1 is a figure showing an alignment of the amino acid sequence (amino acid sequence of SEQ ID NO: 2) of human Eva1 (hEva1) and the amino acid sequence (amino acid sequence of SEQ ID NO: 4) of mouse Eva1 (mEva1). In the figure, the underlined amino acid sequence shows the sequence (86th to 102nd amino acids) of a synthetic peptide used as an antigen of an anti-Eva1 antibody. Moreover, the bold letters represent a signal sequence (1st to 20th amino acids), a portion encompassed by a square indicates a transmembrane domain (152nd to 175th amino acids), and the arrows indicate cysteine residues.

DESCRIPTION OF EMBODIMENTS

<Glioma Treatment Method>

Figure 2:
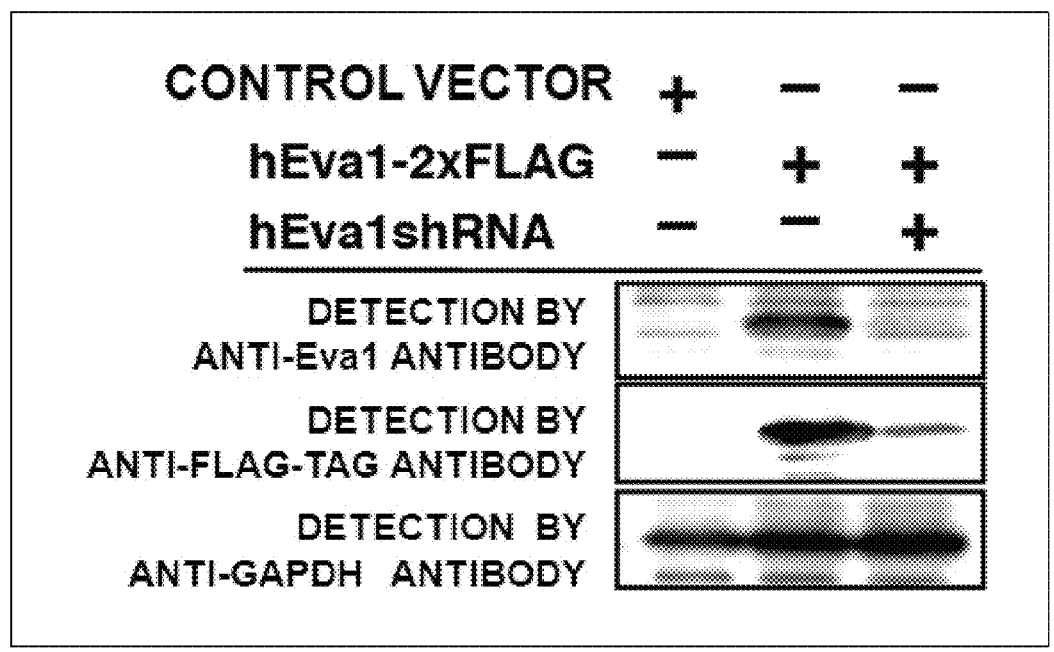
FIG. 2 shows photographs for illustrating the result of evaluating the anti-Eva1 antibody by western blotting using a hEva1 protein fused with a FLAG® (DYKDDDDK (SEQ ID NO: 77)) peptide; manufactured by SIGMA-ALDRICH CO). Note that the analysis result using an anti-FLAG® antibody is a positive control of the analysis result using the anti-Eva1 antibody, and the analysis result using an anti-GAPDH antibody was used as an internal standard (loading control).

The present invention provides a glioma treatment method comprising suppressing a function of at least any one gene of an Eva1 gene and a Ceacam1 gene in a subject.

In the present invention, a "glioma" is a collective term for tumors arising from neural stem cells, neural precursor cells, and neuroglial cells. Examples thereof include glioblastoma multiforme (GBM), astrocytomas, medulloblastoma, ependymoma, oligodendroglioma, choroid plexus papilloma, particularly anaplastic astrocytoma, anaplastic oligodendroastrocytoma, and anaplastic oligodendroglioma, but are not limited to these diseases.

Note that examples of the glioma treatment according to the present invention include those involving suppression of the growth potential of glioma cells, suppression of the tumor-forming potential of glioma cells, suppression of the tissue invading potential of glioma cells, suppression of tumor mass-forming potential of glioma stem cells, suppression of angiogenesis in a glioma, or the like.

The "subject" in the treatment method of the present invention is a glioma patient. When a glioma in an animal other than human is to be treated, examples of the subject include mice, rats, dogs, cats, cattle, horses, pigs, birds, and the like.

In the treatment method of the present invention, the phrase "suppressing a function of a gene" means to include both suppressing an expression of a gene (suppression of transcription, suppression of translation) and suppressing functions of a transcription product (mRNA) and a translation product (protein).

In the present invention, the "Eva1 gene" whose function is to be suppressed is a gene typically comprising a DNA sequence of SEQ ID NO: 1 if derived from human, or a gene typically comprising a DNA sequence of SEQ ID NO: 3 if derived from mouse. Nevertheless, the DNA sequence of a gene may be mutated naturally (i.e., non-artificially) by a mutation or the like. Thus, in the present invention, the function of such naturally-occurring mutants may also be suppressed.

In the present invention, the "Ceacam1 gene" whose function is to be suppressed is also called a BGP (BILIARY GLYCOPROTEIN), BGP1 (BILIARY GLYCOPROTEIN 1) or CD66 (CD66 antigen) gene. The gene is located in 19q13.2 of human or in chromosome 7 of mouse. If derived from human, the gene is typically a gene comprising a DNA sequence of SEQ ID NO: 13 (human Ceacam1-L gene) and a gene comprising a DNA sequence of SEQ ID NO: 15 (human Ceacam1-S gene). Meanwhile, if derived from mouse, the gene is typically a gene comprising a DNA sequence of SEQ ID NO: 17 (mouse Ceacam1-L gene) and a gene comprising a DNA sequence of SEQ ID NO: 19 (mouse Ceacam1-S gene). Nevertheless, the DNA sequence of a gene may be mutated naturally (i.e., non-artificially) by a mutation or the like. Thus, in the present invention, the function of such naturally-occurring mutants may also be suppressed.

Moreover, as described in Examples later, it has been revealed that the Ceacam1-L gene and a Ceacam6 gene are expressed in human glioma stem cells. Accordingly, in the treatment method of the present invention, the function of the Ceacam6 gene may also be suppress together with at least any one gene of the Eva1 gene and the Ceacam1 gene.

Note that, in the present invention, the "Ceacam6 gene" is also called a NCA (NONSPECIFIC CROSSREACTING ANTIGEN), NORMAL CROSSREACTING ANTIGEN, CEAL (CEA-LIKE PROTEIN) gene. The gene is located in 19q13.2 of human. If derived from human, the gene typically comprises a DNA sequence of SEQ ID NO: 21. Nevertheless, the DNA sequence of a gene may be mutated naturally (i.e., non-artificially) by a mutation or the like. Thus, in the present invention, the function of such naturally-occurring mutants may also be suppressed. Moreover, when the function of the Ceacam6 gene is suppressed, an anti-Ceacam6 protein antibody, a peptide having a dominant-negative phenotype against a Ceacam6 protein, and an RNA capable of binding to a transcription product of the Ceacam6 gene can be used as in "suppressing a function of at least any one gene of an Eva1 gene and a Ceacam1 gene" described below. These molecules can be prepared according to methods described in the section of <Glioma Therapeutic Drug> later.

The "suppressing a function of at least anyone gene of an Eva1 gene and a Ceacam1 gene" can be accomplished by using a "molecule capable of suppressing a function of at least any one gene of an Eva1 gene and a Ceacam1 gene (hereinafter also referred to as "molecule capable of suppressing a function of an Eva1 gene, etc.")" described below. For example, it is possible to use an anti-Eva1 protein antibody, a peptide having a dominant-negative phenotype against an Eva1 protein, an RNA capable of binding to a transcription product of the Eva1 gene, an anti-Ceacam1 protein antibody, a peptide having a dominant-negative phenotype against a Ceacam1 protein, and an RNA capable of binding to a transcription product of the Ceacam1 gene.

Examples of a method for administering the molecule to a subject include direct administration into the brain, intravenous injection, and the like. An example of the method for directly administering the molecule capable of suppressing a function of an Eva1 gene, etc. into a brain is a method in which a cannula or the like is inserted by stereotactic surgery so that the molecule can be administered to a glioma through the cannula. In a case where the molecule capable of suppressing a function of an Eva1 gene, etc. is not directly administered to a brain, it is possible to utilize a method in which the molecule bound to a brain barrier-permeable substance is administered. However, the method is not limited thereto. When the subject is an organism developing GBM, the molecule capable of suppressing a function of an Eva1 gene, etc. can be delivered to the GBM by intravenous injection or the like without binding to a brain barrier-permeable substance because a blood-brain barrier (BBB) a normal brain has is not formed in a blood vessel formed in a brain tumor where angiogenesis has occurred.

An example of the brain barrier-permeable substance is a rabies virus-derived, 29-amino-acid glycoprotein (see Kumar, et al., Nature, 5 Jul. 2007, vol. 448, pp. 39 to 43), but is not limited thereto.

<Glioma Therapeutic Drug>

The present invention provides a glioma therapeutic drug comprising, as an active ingredient, a molecule capable of suppressing a function of at least anyone gene of an Eva1 gene and a Ceacam1 gene.

Examples of the "molecule capable of suppressing a function of an Eva1 gene, etc." include an anti-Eva1 protein antibody, a peptide having a dominant-negative phenotype against an Eva1 protein, an RNA capable of binding to a transcription product of the Eva1 gene, an anti-Ceacam1 protein antibody, a peptide having a dominant-negative phenotype against a Ceacam1 protein, and an RNA capable of binding to a transcription product of the Ceacam1 gene.

Note that, as described in Examples later, it has been revealed that a shRNA targeting the Eva1 gene or a shRNA targeting the Ceacam1 gene suppresses glioma growth and the like. Consequently, a causal relation has been revealed between the suppression of the function of the Eva1 gene or Ceacam1 gene and the suppression of glioma growth and the like. Further, it has been revealed that the anti-Eva1 antibody inhibits glioma stem cells from forming tumor cell mass. Thus, it is apparent that it is possible to suppress glioma growth and the like by use of the molecules, including the shRNAs and antibodies, capable of suppressing a function of these genes.

The anti-Eva1 protein antibody or the anti-Ceacam1 protein antibody (hereinafter also referred to as "anti-Eva1 protein antibody, etc.") may be a polyclonal antibody, a monoclonal antibody, or a functional fragment of an antibody. Moreover, the "antibody" includes all classes and subclasses of immunoglobulins. The "functional fragment" of an antibody means a part (partial fragment) of an antibody, which specifically recognizes the Eva1 protein or the Ceacam1 protein. Specific examples thereof include Fab, Fab', F(ab')2, a variable region fragment (Fv), a disulfide bonded Fv, a single chain Fv (scFv), a sc(Fv)2, a diabody, a polyspecific antibody, polymers thereof, and the like.

Further, the anti-Eva1 protein antibody, etc. includes a chimeric antibody, a humanized antibody, a human antibody, and functional fragments of these antibodies. For administration as a therapeutic drug to human, the antibody of the present invention is desirably a chimeric antibody, a humanized antibody, or a human antibody from the viewpoint of side effect reduction.

In the present invention, a "chimeric antibody" is an antibody obtained by linking a variable region of an antibody of one species to a constant region of an antibody of another species. A chimeric antibody can be obtained as follows, for example. Specifically, a mouse is immunized with an antigen. A portion corresponding to an antibody variable part (variable region) which binds to the antigen is cut out from a gene of a monoclonal antibody of the mouse. The portion is linked to a gene of a constant part (constant region) of an antibody derived from human bone marrow. This is incorporated into an expression vector, which is then introduced into a host for the production of a chimeric antibody (for example, Japanese Unexamined Patent Application Publication No. Hei 8-280387, U.S. Pat. No. 4,816, 397, U.S. Pat. No. 4,816,567, U.S. Pat. No. 5,807,715).

Moreover, in the present invention, a "humanized antibody" is an antibody obtained by grafting (CDR grafting) a gene sequence of an antigen-binding site (CDR) of anon-human-derived antibody onto a human antibody gene. The preparation methods are known (see, for example, EP239400, EP125023, WO90/07861, WO96/02576). In the present invention, a "human antibody" is an antibody, all regions of which are derived from human. In preparing a human antibody, it is possible to utilize a transgenic animal (for example, a mouse) capable of producing a repertoire of the human antibody by immunization. Preparation methods for a human antibody are known (For example, Nature, 1993, 362, 255-258, Intern. Rev. Immunol, 1995, 13, 65-93, J. Mol. Biol 1991, 222, 581-597, Nature Genetics, 1997, 15, 146-156, Proc. Natl. Acad. Sci. USA, 2000, 97: 722-727, Japanese Unexamined Patent Application Publication No. Hei 10-146194, Japanese Unexamined Patent Application Publication No. Hei10-155492, Japanese Patent No. 2938569, Japanese Unexamined Patent Application Publication No. Hei 11-206387, International Application Japanese-Phase Publication No. Hei 8-509612, International Application Japanese-Phase Publication No. Hei 11-505107).

Furthermore, the anti-Eva1 protein antibody, etc. includes antibodies whose amino acid sequences are modified without impairing desirable activities (such as activity of binding to the Eva1 protein or the Ceacam1 protein, anti-glioma activity, and/or other biological properties). An amino acid sequence mutant can be prepared by introduction of a mutation into a DNA encoding an antibody chain or by peptide synthesis. A site of the antibody where the amino acid sequence is modified may be a constant region of a heavy chain or a light chain of the antibody or a variable region (framework region and CDR) thereof, as long as the resulting antibody has activities equivalent to those before the modification. It is conceivable that modification on an amino acid other than CDR has relatively small influence on binding affinity for an antigen. As of now, there are known screening methods for antibodies whose affinity for an antigen has been enhanced by modifying an amino acid of CDR (PNAS, 102: 8466-8471 (2005), Protein Engineering, Design & Selection, 21: 485-493 (2008), International Publication No. WO2002/051870, J. Biol. Chem., 280: 24880-24887 (2005), Protein Engineering, Design & Selection, 21: 345-351 (2008)).

The number of amino acids modified is preferably 10 amino acids or less, more preferably 5 amino acids or less, and most preferably 3 amino acids or less (for example, 2 amino acids or less, or 1 amino acid). The amino acid modification is preferably conservative substitution. In the present invention, the "conservative substitution" means substitution with a different amino acid residue having a chemically similar side chain. Groups of amino acid residues having chemically similar amino acid side chains are well known in the technical field to which the present invention pertains. For example, amino acids can be grouped into acidic amino acids (aspartic acid and glutamic acid), basic amino acids (lysine, arginine, histidine), and neutral amino acids such as amino acids having a hydrocarbon chain (glycine, alanine, valine, leucine, isoleucine, proline), amino acids having a hydroxy group (serine, threonine), sulfur-containing amino acids (cysteine, methionine), amino acids having an amide group (asparagine, glutamine), an amino acid having an imino group (proline), and amino acids having an aromatic group (phenylalanine, tyrosine, tryptophan). The amino acid sequence mutant preferably has an antigen-binding activity equivalently to that of subject antibodies (for example, antibodies described in the present Examples). The antigen-binding activity can be evaluated, for example, through analysis using a flow cytometer, ELISA, western blotting, immunoprecipitation, or the like.

Furthermore, in the present invention, for the purpose of increasing the stability of the antibody or other purposes, an amino acid subjected to deamidation or an amino acid adjacent to the amino acid subjected to the deamidation may be substituted with a different amino acid to suppress the deamidation. Moreover, the stability of the antibody can also be increased by substituting glutamic acid with a different amino acid. The present invention also provides an antibody thus stabilized.

The modification of the antibody may be a modification on post-translational process of the antibody, for example, the change in the number of sites of glycosylation or in location of the glycosylation. This can improve, for example, the ADCC activity of the antibody. Glycosylation of the antibody is typically N-linked or O-linked glycosylation. The glycosylation of the antibody greatly depends on host cells used for expression of the antibody. The glycosylation pattern can be modified by known methods such as introduction or deletion of a certain enzyme involved in carbohydrate production (Japanese Unexamined Patent Application Publication No. 2008-113663, U.S. Pat. No. 5,047,335, U.S. Pat. No. 5,510,261, U.S. Pat. No. 5,278,299, International Publication No. WO99/54342).

The anti-Eva1 protein antibody, etc. used in the therapeutic drug of the present invention may be bound to a substance, such as a cytotoxic agent, for glioma treatment as described in the section of <Delivering Method to Glioma, and Delivering Drug to Glioma> later. By using such an antibody, a so-called missile therapy is possible.

Examples of the peptide having a dominant-negative phenotype against an Eva1 protein the glioma therapeutic drug comprises as the active ingredient include polypeptides having an amino acid sequence of SEQ ID NO: 2 or 4 subjected to substitution, deletion, addition and/or insertion. Preferable is a peptide comprising an extracellular region of the Eva1 protein described in Examples later.

Moreover, examples of the peptide having a dominant-negative phenotype against a Ceacam1 protein the glioma therapeutic drug comprises as the active ingredient include polypeptides having an amino acid sequence of SEQ ID NO: 14, 16, 18, or 20 subjected to substitution, deletion, addition and/or insertion.

Examples of the RNA capable of binding to a transcription product of the Eva1 gene or the RNA capable of binding to a transcription product of the Ceacam1 gene (hereinafter also referred to as "RNA capable of binding to a transcription product of the Eva1 gene, etc.") the glioma therapeutic drug comprises as the active ingredient include complementary dsRNAs (double-stranded RNAs) to transcription products of the genes encoding the Eva1 protein or the Ceacam1 protein or DNAs encoding the dsRNAs.

Each of the DNAs encoding the dsRNAs comprises: an antisense DNA encoding an antisense RNA for a region of any of the transcription products (mRNAs) of the target gene; and a sense DNA encoding a sense RNA for a region of any of the mRNAs. The antisense RNA and the sense RNA can be expressed by the antisense DNA and the sense DNA, respectively. Moreover, the dsRNA can be prepared by these antisense RNA and sense RNA.

As the configuration to incorporate the dsRNA expression system into a vector or the like, the antisense RNA and the sense RNA may be expressed from the same vector, or the antisense RNA and the sense RNA may be expressed from different vectors, respectively. As the configuration in which the antisense RNA and the sense RNA are expressed from the same vector, for example, an antisense RNA expression cassette and a sense RNA expression cassette are constructed in each of which a promoter capable of expressing a short RNA, such as a pol III type, is linked upstream of the antisense DNA or the sense DNA, and these cassettes are inserted into the vector in the same direction or opposite directions.

Moreover, it is also possible to construct an expression system in which the antisense DNA and the sense DNA are arranged in opposite directions in such a manner as to face each other on different strands. This configuration includes: a single double-stranded DNA (siRNA-encoding DNA) in which an antisense RNA-encoding strand is paired with a sense RNA-encoding strand; and promoters facing each other on both sides of the DNA so that the antisense RNA and the sense RNA can be expressed from the respective strands. In this case, in order to avoid addition of unnecessary sequences downstream of the sense RNA and the antisense RNA, it is preferable to provide a terminator at the 3' end of each of the strands (the antisense RNA-encoding strand, the sense RNA-encoding strand). As this terminator, a sequence of four or more consecutive A (adenine) bases, or the like can be used. In addition, in this palidromic expression system, the type of the two promoters is preferably different.

Meanwhile, As the configuration in which the antisense RNA and the sense RNA are expressed from different vectors, for example, an antisense RNA expression cassette and a sense RNA expression cassette are constructed in each of which a promoter capable of expressing a short RNA, such as a pol III type, is linked upstream of the antisense DNA or the sense DNA, and these cassettes are incorporated into different vectors. Note that those skilled in the art could prepare the dsRNA by chemically synthesizing the strands.

The dsRNA used in the present invention is preferably a siRNA or a shRNA (short hairpin RNA). A siRNA means double-stranded RNA made of short strands in such a range that no toxicity is demonstrated within cells. Meanwhile, a shRNA means a single-stranded RNA in which a sense RNA and an antisense RNA are arranged with a spacer sequence therebetween. Hydrogen bonds are formed between the sense RNA and the antisense RNA in cells or the like, and the spacer sequence has a hairpin structure. A siRNA can be formed from the shRNA as the hairpin structure is cut out in the cells.

Furthermore, the length of the dsRNA is not particularly limited, as long as the expression of the target gene can be suppressed and no toxicity is demonstrated. The length is for example 15 to 49 base pairs, preferably 15 to 35 base pairs, and more preferably 21 to 30 base pairs.

The DNAs encoding the dsRNAs do not always have to have completely the same base sequence as that of the target gene, but the homology of the sequences is at least 70% or more, preferably 80% or more, and further preferably 90% or more (for example, 95%, 96%, 97%, 98%, 99% or more). The homology of the sequences can be determined with a BLAST program.

Examples of another form of the "RNA capable of binding to a transcription product of the Eva1 gene, etc." in the present invention include a DNA (antisense DNA) encoding an antisense RNA complementary to the transcription product of the Eva1 gene or the transcription product of the Ceacam1 gene, and a DNA encoding an RNA (ribozyme) having a ribozyme activity of specifically cleaving the transcription product of the Eva1 gene or the transcription product of the Ceacam1 gene.

The molecule capable of suppressing a function of an Eva1 gene, etc. of the present invention may be bound to the above-described brain barrier-permeable substance. The therapeutic drug of the present invention may comprise other ingredients in addition to the molecule capable of suppressing a function of an Eva1 gene, etc. Examples of the other ingredients include a carrier, an excipient, a disintegrator, buffer, an emulsifier, a suspension, a stabilizer, a preservative, an antiseptic, physiological salt, and the like. As the excipient, lactose, starch, sorbitol, D-mannitol, white sugar, or the like can be used. As the disintegrator, starch, carboxymethyl cellulose, calcium carbonate, or the like can be used. As the buffer, a phosphate, a citrate, an acetate, or the like can be used. As the emulsifier, gum arabic, sodium alginate, tragacanth, or the like can be used. As the suspension, glyceryl monostearate, aluminium monostearate, methyl cellulose, carboxymethyl cellulose, hydroxymethyl cellulose, sodium lauryl sulfate, or the like can be used. As the stabilizer, propylene glycol, diethylin sulfite, ascorbic acid, or the like can be used. As the preservative, phenol, benzalkonium chloride, benzyl alcohol, chlorobutanol, methylparaben, or the like can be used. As the antiseptic, sodium azide, benzalkonium chloride, para-hydroxybenzoic acid, chlorobutanol, or the like can be used.

<Glioma Testing Method>

The present invention provides a glioma testing method comprising detecting an expression of at least any one gene of an Eva1 gene and a Ceacam1 gene in a subject.

Moreover, as described in Examples later, a high correlation has been found out between the survival rate of glioma patients and an expression of the Eva1 gene or the Ceacam1 gene in gliomas derived from the patients. Accordingly, the testing method of the present invention enables not only testing for whether or not a glioma is developed, but also testing for a prognosis of glioma patients. Such tests are not particularly limited. For example, the prognosis of glioma patients can be determined based on a graph shown in FIG. 20 or 27.

Examples of the "subject" in the testing method of the present invention include organisms and samples (for example, cells, tissues, organs, body fluids, and so forth) separated from organisms. The "organism" is not limited to a glioma patient, and may be a healthy subject (including one who may develop a glioma). When a test is to be conducted for a glioma in an animal other than human, examples of the "organism" are animals such as mice, rats, dogs, cats, cattle, horses, pigs, and birds.

In the present invention, the "Eva1 gene" whose expression is to be detected is a gene typically comprising a DNA sequence of SEQ ID NO: 1 if derived from human, or a gene typically comprising a DNA sequence of SEQ ID NO: 3 if derived from mouse. Nevertheless, the DNA sequence of a gene may be mutated naturally (i.e., non-artificially) by a mutation or the like. Thus, in the present invention, such naturally-occurring mutants may also be detected.

Moreover, in the present invention, the "Ceacam1 gene" whose expression is to be detected is, if derived from human, typically a gene comprising a DNA sequence of SEQ ID NO: 13 (human Ceacam1-L gene) and a gene comprising a DNA sequence of SEQ ID NO: 15 (human Ceacam1-S gene). Meanwhile, if derived from mouse, the gene is typically a gene comprising a DNA sequence of SEQ ID NO: 17 (mouse Ceacam1-L gene) and a gene comprising a DNA sequence of SEQ ID NO: 19 (mouse Ceacam1-S gene). Nevertheless, the DNA sequence of a gene may be mutated naturally (i.e., non-artificially) by a mutation or the like. Thus, in the present invention, such naturally-occurring mutants may also be detected.

In the present invention, the phrase "detecting an expression of a gene" means to include both detecting whether the gene is expressed or not and detecting the degree of the expression. A level of the gene expressed can be grasped as an absolute level or a relative level. When a relative level is to be grasped, for example, the level of the gene expressed can be determined in comparison with a level of the gene expressed from a prepared reference sample. The "reference sample" is a sample which has been identified regarding whether or not the target gene is expressed in advance. For example, a pathological tissue having a site where a glioma is present identified in advance can be used as the reference sample of the present invention. Moreover, a tissue where a glioma is not developed (normal tissue) can also be used as the reference sample of the present invention.

Further, in the present invention, the "expression of a gene" means to include both transcription and translation of the gene. Thus, in the present invention, the "detecting an expression of a gene" includes detecting at both a transcription level (mRNA level) and a translation level (protein level).

In the present invention, known methods can be used to detect an expression of a gene. Examples of the detecting method at a transcription level include RT-PCR, DNA microarray analysis, northern blotting, in situ hybridization, dot blot, and Raze protection assay. Meanwhile, examples of the detecting method at a translation level include detecting methods using an antibody (immunological methods) such as immunohistochemical staining, imaging cytometry, flow cytometry, ELISA, radioimmunoassay, immunoprecipitation, immunoblotting, antibody array, and in vivo imaging. In the present invention, from the viewpoint of convenience, the detecting method at a translation level is preferable, and particularly the detecting methods using an antibody (immunological methods) are preferable.

In the testing method of the present invention, an antibody bound to a labeling substance can be used. By using the antibody bound to a labeling substance, the amount of the antibody bound to an Eva1 protein or the amount of the antibody bound to a Ceacam1 protein can be measured directly. Moreover, it is possible to utilize indirect detecting methods such as a method utilizing a secondary antibody bound to a labeling substance and a method utilizing a polymer bound to a labeling substance and a secondary antibody. Here, the "secondary antibody" is an antibody that exhibits specific binding to the antibody of the present invention. For example, when the antibody of the present invention is prepared as a rabbit antibody, an anti-rabbit IgG antibody can be used as the secondary antibody. Labeled secondary antibodies usable to antibodies derived from various species such as rabbits, goats, and mice are commercially available. In the present invention, it is possible to use a secondary antibody selected as appropriate, depending on the species from which the antibody of the present invention is derived. Protein G, Protein A, or the like, to which a labeling substance is bound can also be used instead of a secondary antibody.

Information obtained by performing the method of the present invention targeting glioma patients can be utilized for evaluation and grasping of the pathological condition of the patients, evaluation of a treatment effect, and so forth. For example, when the method of the present invention is performed together with a glioma treatment, the treatment effect can be evaluated based on the resulting information thus obtained. Specifically, a change in expressions of the Eva1 gene and/or the Ceacam1 gene in a pathological tissue is examined by performing the method of the present invention after drug administration, and the treatment effect can be determined on the basis of a change in increase or decrease of the Eva1 gene level and/or the Ceacam1 gene level. In this manner, the method of the present invention may be utilized for monitoring a treatment effect.

Glioma testing is conducted normally by a doctor (including one instructed by a doctor. The same shall apply hereinafter). The data on the level of the Eva1 gene expressed and the level of the Ceacam1 gene expressed in a pathological tissue, which are obtained by the method of the present invention, are useful for a diagnosis by a doctor. Thus, the method of the present invention can also be stated as a method for collecting and presenting data useful for a diagnosis by a doctor.

<Glioma Testing Drug>

The present invention provides a glioma testing drug comprising, as an active ingredient, a molecule capable of binding to an expression product of at least any one gene of an Eva1 gene and a Ceacam1 gene in a subject.

In the present invention, the "expression product of at least any one gene of an Eva1 gene and a Ceacam1 gene" refers to a transcription product (mRNA) or a translation product (protein) of the Eva1 gene and/or the Ceacam1 gene. Examples of the molecule capable of binding to the transcription product of the Eva1 gene or the Ceacam1 gene include primers used in RT-PCR and probes used in DNA microarray analysis, northern blotting, and the like. The molecule is a polynucleotide containing a base sequence complementary to the base sequence of the transcription product of the Eva1 gene or the Ceacam1 gene. Preferably, the molecule is a polynucleotide containing a base sequence having consecutive 15 bases or more complementary to the base sequence of the transcription product of the Eva1 gene or the Ceacam1 gene.

Examples of the molecule capable of binding to the translation product of the Eva1 gene or the Ceacam1 gene include an anti-Eva1 protein antibody and an anti-Ceacam1 protein antibody. The "antibody" may be a polyclonal antibody, a monoclonal antibody, or a functional fragment of an antibody. Moreover, the "antibody" includes all classes and subclasses of immunoglobulins. The "functional fragment" of an antibody means a part (partial fragment) of an antibody, which specifically recognizes the Eva1 protein. Specific examples thereof include Fab, Fab', F(ab')2, a variable region fragment (Fv), a disulfide bonded Fv, a single chain Fv (scFv), a sc(Fv)2, a diabody, a polyspecific antibody, polymers thereof, and the like.

When the antibody of the present invention is a polyclonal antibody, the polyclonal antibody can be obtained as follows. Specifically, an animal to be immunized is immunized with an antigen (the Eva1 protein or the Ceacam1 protein, a partial peptide thereof, cells expressing these, or the like). The polyclonal antibody can be obtained by purification of an antiserum from the animal by conventional means (for example, salting-out, centrifugation, dialysis, column chromatography, or the like). Meanwhile, a monoclonal antibody can be prepared by a hybridoma method or a recombinant DNA method. An example of the hybridoma method is a method by Kohler and Milstein (Kohler & Milstein, Nature, 256: 495 (1975)). An example of the recombinant DNA method is a method by which the antibody of the present invention is produced as a recombinant antibody as follows. A DNA encoding the antibody of the present invention or a peptide thereof is cloned from a hybridoma, B cells, or the like. The cloned DNA is incorporated into an appropriate vector, which is introduced into host cells (for example, a mammalian cell line, *Escherichia coli*, yeast cells, insect cells, plant cells, or the like) for the production (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192: 767-775 (1990)).

As the "molecule capable of binding to an expression product of at least any one gene of an Eva1 gene and a Ceacam1 gene" of the present invention, those molecules bound to a labeling substance can be used. By detecting the label, the amount of the molecules bound to the expression product of the Eva1 gene or the expression product of the Ceacam1 gene can be measured directly. The labeling substance is not particularly limited, as long as the labeling substance can bind to these molecules and can be detected by a chemical or optical method. Examples thereof include peroxidases, β-D-galactosidase, microperoxidase, horseradish peroxidase (HRP), fluorescein isothiocyanate (FITC), rhodamine isothiocyanate (RITC), alkaline phosphatases, biotin, radioactive substances, and the like.

When the subject in the testing method of the present invention is an organism, the administration of the molecule capable of binding to the expression product of the Eva1 gene or the expression product of the Ceacam1 gene can be selected from the methods described in the section of <Glioma Treatment Method> above.

The testing drug of the present invention may comprise other ingredients described in the section of <Glioma Therapeutic Drug> in addition to the molecule capable of binding to the expression product of the Eva1 gene or the expression product of the Ceacam1 gene.

<Delivering Method to Glioma, and Delivering Drug to Glioma>

The present invention provides: a method for delivering a desired substance to a glioma in a subject, the method comprising administering, to the subject, at least any one antibody of an anti-Eva1 protein antibody to which the desired substance binds and an anti-Ceacam1 protein antibody to which the desired substance binds; and a drug for delivering a desired substance to a glioma in a subject, the drug comprising, as an active ingredient, at least any one antibody of an anti-Eva1 protein antibody and an anti-Ceacam1 protein antibody.

In the present invention, the "desired substance" is not particularly limited. When a glioma is to be treated, examples of the substance include cytotoxic agents, particularly ribosome inactivating proteins (RIPs), that is, saporin, ricin, Shiga toxin, and the like. When a glioma testing is to be conducted, examples of the substance include labeling substances described above. When research and development are to be conducted targeting a glioma, examples thereof include test substances for evaluating the action on the glioma.

The "anti-Eva1 protein antibody" and the "anti-Ceacam1 protein antibody" to which the desired substance binds are the same as the antibodies described in the section of <Glioma Therapeutic Drug> or the section of <Glioma Testing Drug> above. Moreover, the method for administering, to the subject, the anti-Eva1 protein antibody to which the desired substance binds and/or the anti-Ceacam1 protein antibody to which the desired substance binds can be selected from the methods described in the section of <Glioma Treatment Method> above.

The delivering drug to a glioma may comprise other ingredients described in the section of <Glioma Therapeutic Drug> in addition to the anti-Eva1 protein antibody and/or the anti-Ceacam1 protein antibody to which the desired substance binds.

EXAMPLES

Hereinafter, the present invention will be described more specifically based on Examples. However, the present invention is not limited to the following Examples. Note that the following Examples were carried out based on the experimental method described below.

<Animals, Reagents, and so Forth>

Mice were obtained from Laboratory for Animal Resources and Genetic Engineering at Riken Center for Developmental Biology (CDB) and Charles River Laboratories Japan, Inc. Moreover, all the experimental protocols for the mice were approved by the Riken CDB Animal Experiment Committee. Reagents and growth factors were respectively purchased from Sigma-Aldrich Japan and Pero-Tech Inc. unless otherwise clearly stated.

<Cell Culturing>

Mouse neural stem cells (NSCs), mouse NSCL61, and human glioma stem cells (hGICs) were prepared as described in the following literatures, and cultured in NSC media (DMEM/F12 (manufactured by Gibco, BRL) supplemented with reagents, bFGF (10 ng/ml) and EGF (10 ng/ml)) (see Kondo T, et al., Genes Dev, 2004, vol. 18, pp. 2963 to 2972, and Hide T., et al., Cancer Res., 2009, vol. 69, pp. 7953 to 7959).

In addition, OPCL61 was established as follows. Specifically, first, differentiation into oligodendrocyte precursor cells (OPCs) was induced by culturing mouse-derived p53-deficient neural stem cells (p53-deficient NSCs) using an OPC medium (reagents, PDGFAA (10 ng/ml), bFGF (2 ng/ml), and 0.25% fetal calf serum(FCS)). Then, the OPCs were purified by sequential immunopanning (see Kondo T, et al., Genes Dev, 2004, vol. 18, pp. 2963 to 2972). Subsequently, $2\times10^6$ OPCs thus obtained were suspended in 100 μl of a mouse NSC Nucleofector solution (manufactured by Lonza Group Ltd.) containing 10 μg of pCMS-EGFP-HRasL61 encoding GFP and a constitutive active form of HRas. Thereafter, this plasmid vector was introduced into the OPCs using a gene-introducing device (product name: Nucleofector, manufactured by Lonza Group Ltd.). The OPCs having the genes introduced therein were cultured in an optimized medium, and GFP-positive cells were isolated by using flow cytometry (with JSAN Cell Sorter: product name, manufactured by Bay bioscience Co., Ltd.).

Glioma (glioblastoma) cell lines (C6, T98G, Tp483, SF126, U87, and U251) were maintained in DMEM supplemented with 10% fetal calf serum (FCS), 100 units/ml of penicillin G, and 100 ug/ml of streptomycin (manufactured by GIBCO). For Eva1 staining, the cells were cultured in a NSC medium for 7 days, and analyzed by employing flow cytometry SF126 was purchased from HS Research Resources Bank.

<Fluorescence Activated Cell Sorting (FACS)>

The hGIC and glioma cell lines were immunolabeled with a rabbit-derived anti-Eva1 polyclonal antibody (10 μg/ml) and an ALEXA FLUOR® 568 (Alexa 568-labeled goat-derived anti-rabbit IgG antibody, manufactured by Molecular Probes, diluted to 1/400 when used). Then, the immunolabeled cells were passed through JSAN Cell Sorter (manufactured by Bay bioscience Co., Ltd.), and analyzed using excitation light of two wavelengths (488-nm solid-state laser and 638-nm semiconductor laser). Note that propidium iodide (PI)-positive cells (for example, dead cells) were excluded from the analysis.

<Immunostaining>

Dissected mouse brains were fixed in 4% paraformaldehyde at 4° C. overnight. After the fixation, the brains were cryoprotected using PBS containing 12 to 18% sucrose and embedded in an OCT compound. Then, coronal sections (thickness: 10 µm) were prepared from the cerebral cortexes. Note that Eva1 was activated using HistoVT One (manufactured by Nacalai Tesque, Inc.) according to the instruction. Next, in order to infiltrate the antibodies, the sections were pretreated with 0.3% TRITON™ X-100 (4-(1,1,3,3-Tetramethylbutyl)phenyl-polyethylene glycol, t-Octylphenoxypolyethoxyethanol, Polyethylene glycol tert-octylphenyl ether)-containing PBS, and subsequently treated in a blocking solution (2% skim milk, 0.3% TRITON™ X-100, PBS) for 1 hour. Thereafter, the sections were incubated together with the primary antibodies at 4° C. for 16 hours. The fixed cells were immunostained as described in the following literature (see Kondo T, et al., EMBO J, 2000, vol. 19, pp. 1998 to 2007). Moreover, the following antibodies were used to detect antigens in the cells: rabbit-derived anti-Eva1 polyclonal antibody (5 µg/ml);
mouse-derived anti-rat Nestin monoclonal antibody (manufactured by BD Biosciences, diluted to 1/400 when used);
rat-derived anti-GFP monoclonal antibody (manufactured by Nacalai Tesque, Inc., diluted to 1/500 when used);
mouse-derived anti-CD31 monoclonal antibody (manufactured by Abcam plc., diluted to 1/200 when used); and
mouse-derived anti-Ceacam1 monoclonal antibody (manufactured by R&D Systems, Inc., diluted to 1/50 when used).

These antibodies were detected using ALEXA FLUOR® 568 (Alexa 568-labeled goat-derived anti-rabbit IgG, manufactured by Molecular Probes, diluted to 1/400 when used), ALEXA FLUOR® 488 (Alexa 488-labeled goat-derived anti-rabbit IgG or anti-rat IgG, manufactured by Molecular Probes, diluted to 1/400 when used), or Cy3-labeled goat-derived anti-mouse IgG antibody (manufactured by Jackson ImmunoResearch Laboratories, Inc., diluted to 1/400 when used). Further, in order to visualize the nuclei, the cells were subjected to counter staining with Hoechst 33342 (1 µg/ml).

<Human Brain Tumor>

Human-derived glioma stem cells, hGICs (hGIC1 and hGIC2), described in "Hide T., et al., Cancer Res., 2009, vol. 69, pp. 7953 to 7959" were used. Moreover, human-derived primary GBM (primary glioblastoma multiforme) tissues, human primary glioma tissues, were provided from Department of Neurosurgery, School of Medicine, Kumamoto University. Further, these human-derived samples were used with the approvals of the ethical committees of Riken CDB and Graduate School of Medical Sciences, Kumamoto University according to the research guidelines of both. Note that hGICs, hGIC1, and hGIC2 are also referred to as hGSCs, hGSC1, and hGSC2, respectively.

In addition, poly(A)+ RNA was prepared from these samples using QuickPrep mRNA Purification Kit (manufactured by GE Healthcare), and the cDNA was synthesized using Transcription First Strand cDNA Synthesis Kit (manufactured by Roche Diagnostics K. K.).

Moreover, paraffin-embedded human brain tumors were prepared into sections 6 µm in thickness. Further, for Eva1 staining, HistoVT One (manufactured by Nacalai Tesque, Inc.) was used according to the instruction to retrieve the antigen. Next, the sections were pretreated in 5% skim milk-containing TPBS at room temperature for 30 minutes, incubated together with the rabbit-derived anti-Eva1 polyclonal antibody (diluted to 1/50 when used) at room temperature for 2 hours, and then immunostained using ALEXA FLUOR® 488 (Alexa 488-labeled goat-derived anti-rabbit IgG, manufactured by Molecular Probes, diluted to 1/400 when used). Further, in order to visualize all the nuclei, the cells were subjected to counter staining with Hoechst 33342 (1 µg/ml).

<Intracranial Cell Transplantation into Nude Mouse Brains>

NSCL61 and hGICs were suspended in 5 µl of media, and injected into brains of 5- to 8-week old female nude mice anesthetized with 10% pentobarbital in advance. The stereotaxic coordinates of the injection site were 2 mm forward from lambda, 2 mm rearward from the sagittal suture, and 5 mm deep.

<RT-PCR>

RT-PCR was carried out as described in the following literature (see Kondo T, et al., EMBO J, 2000, vol. 19, pp. 1998 to 2007). Cycle parameters were 20 seconds at 94° C., 30 seconds at 57° C., and 35 seconds at 72° C. for 35 cycles. Note that the cycle parameters for gapdh amplification were 15 seconds at 94° C., 30 seconds at 53° C., and 90 seconds at 72° C. for 22 cycles. Moreover, for amplification of each gene, oligonucleotide DNA primers shown in Table 1 were synthesized and used.

TABLE 1

| Gene name | 5' primer | SEQ ID NO | 3' primer | SEQ ID NO |
|---|---|---|---|---|
| eva1 | TTCTCCAGCTTTGCCCCTGT | 5 | CCGCCCATCGCTTTTTCCGG | 6 |
| ceacam1 for mouse | ATCCTCCCAAGAGCTCTTTATC | 23 | TTTGTGCTCTGTGAGATCTCG | 24 |
| ceacam1 for human | ACACCATGGGGCACCTCTCA | 25 | GATCGTCTTGACTGTGGTCCT | 26 |
| human ceacam1-L | ACTCTGTGAACCTGACCTGCT | 27 | TTACTGCTTTTTACTTCTGAATA | 28 |
| human ceacam1-S | ACTCTGTGAACCTGACCTGCT | 29 | GGTCCTGAGCTGCCGGTCTT | 30 |
| mouse ceacam1-L | CAACATCCAGTGGCTCTTCAA | 31 | CTTCTTTTTACTTCTGAATAAAC | 32 |
| mouse ceacam1-S | CAACATCCAGTGGCTCTTCAA | 33 | TCAGAAGGAGCCAGATCCGC | 34 |
| fgf5 | CTCACGGGGAGAAGCGTCTC | 35 | TGGCACTTGCATGGAGTTTTC | 36 |
| krt6 | AGCAGGAGATTGCTGAGATC | 37 | GCACCACAGAGATGTTGACT | 38 |

TABLE 1 -continued

| Gene name | 5' primer | SEQ ID NO | 3' primer | SEQ ID NO |
|---|---|---|---|---|
| calcitonin-related polypeptide alpha (calca) for mouse | ATGGGCTTCCTGAAGTTCTCC | 39 | CTTAGATCTGGGGCTGTCCA | 40 |
| calcitonin-related polypeptide alpha (calca) for human | ATGGGCTTCCAAAAGTTCTCC | 41 | CTTAGATCTGGGGCTGTCCA | 42 |
| calcitonin-related polypeptide beta (calcb) for mouse | TTCTTTCCTTTTCTGGCTCTCA | 43 | TCAGGCCTGCAGGTCCCTG | 44 |
| calcitonin-related polypeptide beta (calcb) for human | ATGGGTTTCCGGAAGTTCTCC | 45 | ACATTGGTGGGCACGAAGTTG | 46 |
| stanniocalcin 1 (stc1) | TTTTGCATGCCTGGAAAACTCC | 47 | GTCTGTCTGCAGGATGTGGAA | 48 |
| pyruvate dehydrogenase kinase, isozyme 1 (pdk1) | TATGTACCATCCCATCTCTATC | 49 | GACAGAGCCTTAATGTAGATAAC | 50 |
| aldehyde dehydrogenase 1 family, member A3 (aldh1a3) | AAGAAGGAAGGGGCCAAGCT | 51 | TGGTGACAGTTTTCACTTCTGT | 52 |
| hairy/enhancer-of-split related with YRPW motif 1 (hey1) | GCGGACGAGAATGGAAACTTG | 53 | AGTCCTTCAATGATGCTCAGAT | 54 |
| plasminogen activator, urokinase (plau) | GACCCTGGTGCTATGTGCAG | 55 | CCAAAGCCAGTGATCTCACAG | 56 |
| matrix metallopeptidase 13 (mmp13) | GGCTTAGAGGTGACTGGCAAA | 57 | GTCCAGGTTTCATCATCATCAAA | 58 |
| pyroglutamylated RFamide peptide receptor (grfpr) | CATCCTTTTAAAATGAAGTGGCA | 59 | TTCTTCTTCCTGGCTATTTTGG | 60 |
| DNA-damage-inducible transcript 4-like (ddit4l) | AACCCGGCCAGCATTTCAGA | 61 | CCAAGTTCACGTGCATAACAC | 62 |
| biglycan (bgn) | CGCATCTCAGAGGCCAAGCT | 63 | GTTGTTGAAGAGGCTGATGCC | 64 |
| nuclear factor I/X (nfix) | GCTTCTCTAAAGAAGTCAGGAAA | 65 | GACAAACCGGTTGGCAGAGG | 66 |
| neuroblastoma, suppression of tumorigenicity 1 (nbl1) | GTCCATGTGGGAGATTGTGAC | 67 | TCAGTCCTCAGCCCCCTCTT | 68 |
| protein kinase D1 (prkd1) | ATGGAAGAAGGGAGTGATGAC | 69 | GTGTCCTTGCTGGTGTAGTG | 70 |

<Construction of Vectors>

Full-length mouse eva1 was amplified from mouse NSC cDNA using RT-PCR and KOD plus polymerase (manufactured by TOYOBO CO., LTD.) according to the instruction, and cloned in a pMOSBlue vector (manufactured by Roche Diagnostics K. K.). Note that the nucleotide sequence was verified using BigDye Terminator Kit version 3.1 (manufactured by Applied BioSystems Inc.) and an ABI sequencer model 3130x1 (manufactured by Applied BioSystems Inc.). Then, the mouse eva1 cDNA was inserted into a pCDNA3-2×FLAG® (DYKDDDDK peptide)-c vector (manufactured by Invitrogen Corporation), and pcDNA3-eva1-2×FLAG® (DYKDDDDK peptide)-c was obtained.

Note that, in order to amplify the full-length mouse eva1 cDNA, the following oligonucleotide DNA primers were synthesized.

5' primer:
(SEQ ID NO: 7)
5'-AGAATTCGCCACCATGTATGGCAAGAGCCCCGC-3'

3' primer:
(SEQ ID NO: 8)
5'-ACTCGAGGTCTGTATCTTCCACAAAACA-3'.

Further, human and mouse ceacam1-L cDNA fragments were respectively inserted into pcDNA3-2×FLAG® (DYKDDDDK peptide) vectors, and pcDNA3.1-hceacam1-L-2×FLAG® (DYKDDDDK peptide)-c and pcDNA3.1-mceacam1-L-2×FLAG® (DYKDDDDK peptide)-c were obtained.

Note that, in order to amplify the full-length mouse ceacam1-L cDNA fragment, the following oligonucleotide DNA primers were synthesized.

5' primer:
(SEQ ID NO: 71)
5'-AGAATTCGCCACCATGGAGCTGGCCTCAGCACA-3'

3' primer:
(SEQ ID NO: 72)
5'-ACTCGAGCTTCTTTTTTACTTCTGAATA-3'.

In addition, in order to amplify the full-length human ceacam1-L cDNA fragment, the following oligonucleotide DNA primers were synthesized.

5' primer:
(SEQ ID NO: 73)
5'-AGCTAGCGCCACCATGGGGCACCTCTCAGCCCC-3'

-continued

3' primer:
(SEQ ID NO: 74)
5'-ACTCGAGCTGCTTTTTTACTTCTGAATA-3'.

Moreover, in order to knockdown mouse eva1, human eva1, mouse ceacam1, and human ceacam1, hairpin sequences of these were prepared using InvivoGen siRNA Wizard-(http at sirnawizard.com), and respectively inserted into psiRNA-h7SKhygro G1 expression vectors (manufactured by InvivoGen), and psiRNA-h7SKhygro-meva1sh, psiRNA-h7SKhygro-heva1sh, psiRNA-h7SK-mCC1sh, and psiRNA-h7SK-hCC1sh were obtained.

Note that the target sequence of mouse eva1 was 5'-GCA-GTCAACGGGACAGATGTT-3' (SEQ ID NO: 9), and the target sequence of human eva1 was 5'-GTGCACACTG-TACGCTTCTCT-3' (SEQ ID NO: 10). In the present Examples, a shRNA targeting the Eva1 genes expressed from these vectors is referred to as "Eva1shRNA", "Eva1sh", or "eva1sh".

The target sequence of mouse ceacam1 was 5'-GGGAAACACTACGGCTATAGA-3' (SEQ ID NO: 75), and the target sequence of human ceacam1 was 5'-GGATG-GCAACCGTCAAATTGT-3' (SEQ ID NO: 76). In addition, in the present Examples, a shRNA targeting the Ceacam1 genes expressed from these vectors is referred to as "ceacam1shRNA" or "ceacam1 sh".

The target sequence of control shRNA (shRNA targeting an EGFP gene) was 5'-GCAAGCTGACCCTGAAGTTCA-3' (SEQ ID NO: 11).

Additionally, transfection was carried out using Nucleofector (manufactured by Lonza Group Ltd.) according to the manufacturer's instruction as described in Hide, T., et al., Cancer Res., 2009, vol. 69, pp. 7953 to 7959 and Hide, T., et al., Stem Cells, 2011, vol. 29, iss. 4, pp. 590 to 599.

<Cytotoxicity Assay>

A cytotoxicity assay was carried out using the rabbit-derived anti-Eva1 polyclonal antibody and an anti-rabbit IgG antibody conjugated with a ribosome inactivating protein, saporin (product name: Rab-ZAP, manufactured by Advanced Targeting Systems, Inc.) according to the instruction. Specifically, a rabbit-derived control IgG (manufactured by Jackson ImmunoResearch Laboratories, Inc.) or anti-Eva1 antibody was incubated together with Rab-ZAP (100 ng) in a 96-well plate at room temperature for 30 minutes. Into each well, 5000 cells of hGIC1 were plated and cultured in a $CO_2$ incubator at 37° C. for 2 days. The cell survival rate was measured by a MTT assay as described in the following literature (see Hide T., et al., Cancer Res., 2009, vol. 69, pp. 7953 to 7959).

<Gene Microarray Analysis>

DNA microarray analysis was carried out using 3D-Gene Mouse Oligo chip 24 k (the number of genes detected: 23,522, manufactured by Toray Industries, Inc.). The total RNA used in the analysis was labeled with Cy5 using Amino Allyl Message AMP II aRNA Amplification Kit, manufactured by Applied BioSystems Inc.). Then, the Cy5-labeled aRNA pool thus obtained was hybridized to a microarray according to the manufacturer's protocol (3d-gene.com). Moreover, the hybridization signal was scanned using ScanArray Express Scanner (manufactured by Perkin Elmer Inc.), and the obtained data was processed using GenePixPro version 5.0 (manufactured by Molecular Devices, LLC.). Further, the raw data of each spot was normalized by substitution with the mean intensity of background signals that were determined from all the signal intensities of the blank spots within the 95% confidence interval. Then, raw data intensity was evaluated as valid if the intensity was higher than two standard deviations (SD) of the background signal intensities. Further, the detected signals of each gene were normalized by a global normalization method (the median of the detected signal intensities was adjusted to 25).

<Western Blotting>

Western blotting was carried out as described in the following literature (see Takanaga H, et al., Stem Cells, 2009, vol. 27, pp. 165 to 74). Note that pcDNA3-eva1-2× FLAG® (DYKDDDDK peptide)-c and the like were introduced into Cos7 cells by transfection, and proteins extracted from the cells 2 days after the transfection were used in the western blotting analysis. Moreover, the blotted membrane was probed using the rabbit-derived anti-Eva1 antibody (diluted to 1/500 when used), a mouse-derived anti-FLAG® (DYKDDDDK peptide) antibody (manufactured by SIGMA-ALDRICH CO., diluted to 1/1000 when used), or a mouse-derived anti-GAPDH antibody (manufactured by Chemicon International, Inc., diluted to 1/1000 when used). Further, an ECL system (manufactured by Amersham plc.) was used for the detection.

<Statistical Analysis>

The survival data were analyzed for significance by the Kaplan-Meier method using GraphPad Prism version 4 software (p values were calculated using the Log-rank test).

Example 1

<Preparation of Peptide Antibody>

First of all, the antibody (anti-Eva1 antibody) according to the present invention was prepared. Specifically, first, as the antigen thereof, 86th to 102nd amino acids (PMSGR-FKDRVSWDGNPE, SEQ ID NO: 12, see FIG. 1) was selected as the antigen from a human-derived Eva1 protein (hEva1, an extracellular region (1st to 150th amino acids) in SEQ ID NO: 2). Next, a synthetic peptide comprising the selected amino acid sequence was prepared and used to immunize a rabbit. Then, sera were collected from the rabbit, and purified using a peptide affinity column. Thus, a rabbit-derived anti-Eva1 polyclonal antibody was prepared.

Additionally, the specificity of the obtained anti-Eva1 antibody was evaluated by western blotting. FIG. 2 shows the obtained result. As apparent from the result shown in FIG. 2, in the western blotting using the protein derived from the Cos7 cells having pcDNA3-eva1-2×FLAG® (DYKDDDDK peptide)-c introduced therein, it was observed that the antibody according to the present invention was able to detect a 2×FLAG® (DYKDDDDK peptide)-attached Eva1 protein (hEva1-2×FLAG®) similarly to an anti-FLAG® (DYKDDDDK peptide) antibody. Moreover, in the western blotting using a protein derived from cells expressing only a control vector (pcDNA3), it was observed that the antibody according to the present invention did not non-specifically detect proteins other than Eva1. Further, in the western blotting using a protein derived from cells in which the expression of hEva1-2×FLAG® (DYKDDDDK peptide) was suppressed by hEva1 shRNA, it was observed that the antibody according to the present invention was able to specifically detect a small amount of the Eva1 protein expressed in cells as in the case of the anti-FLAG® (DYKDDDDK peptide) antibody.

Example 2

<Expression of Eva1 in Glioma Stem Cells>

Figure 3:
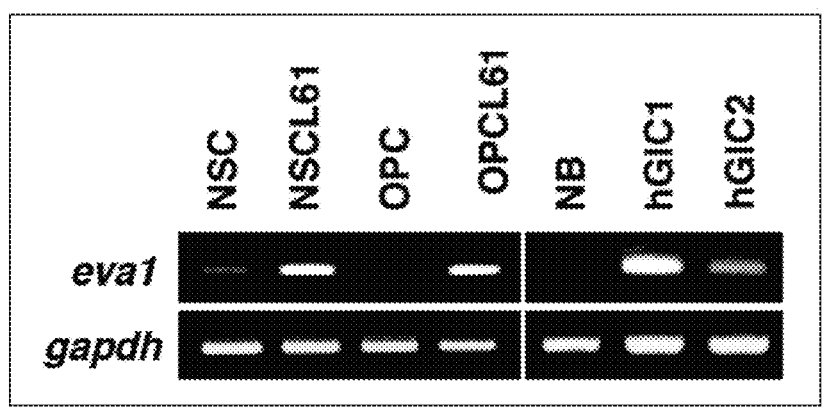
FIG. 3 shows photographs of electrophoreses for illustrating the RT-PCR analysis result on an expression of Eva1 in mouse glioma stem cells and human glioma stem cells. Note that the expression of a gapdh gene was used as an internal standard.

In order to examine an expression of Eva1 at an mRNA level in glioma stem cells (NSCL61, OPCL61, hGIC1, hGIC2) and normal cells (NSC, OPC, NB (neuroblast, neural stem cells)), RT-PCR was carried out. FIG. 3 shows the obtained result.

Figure 4:
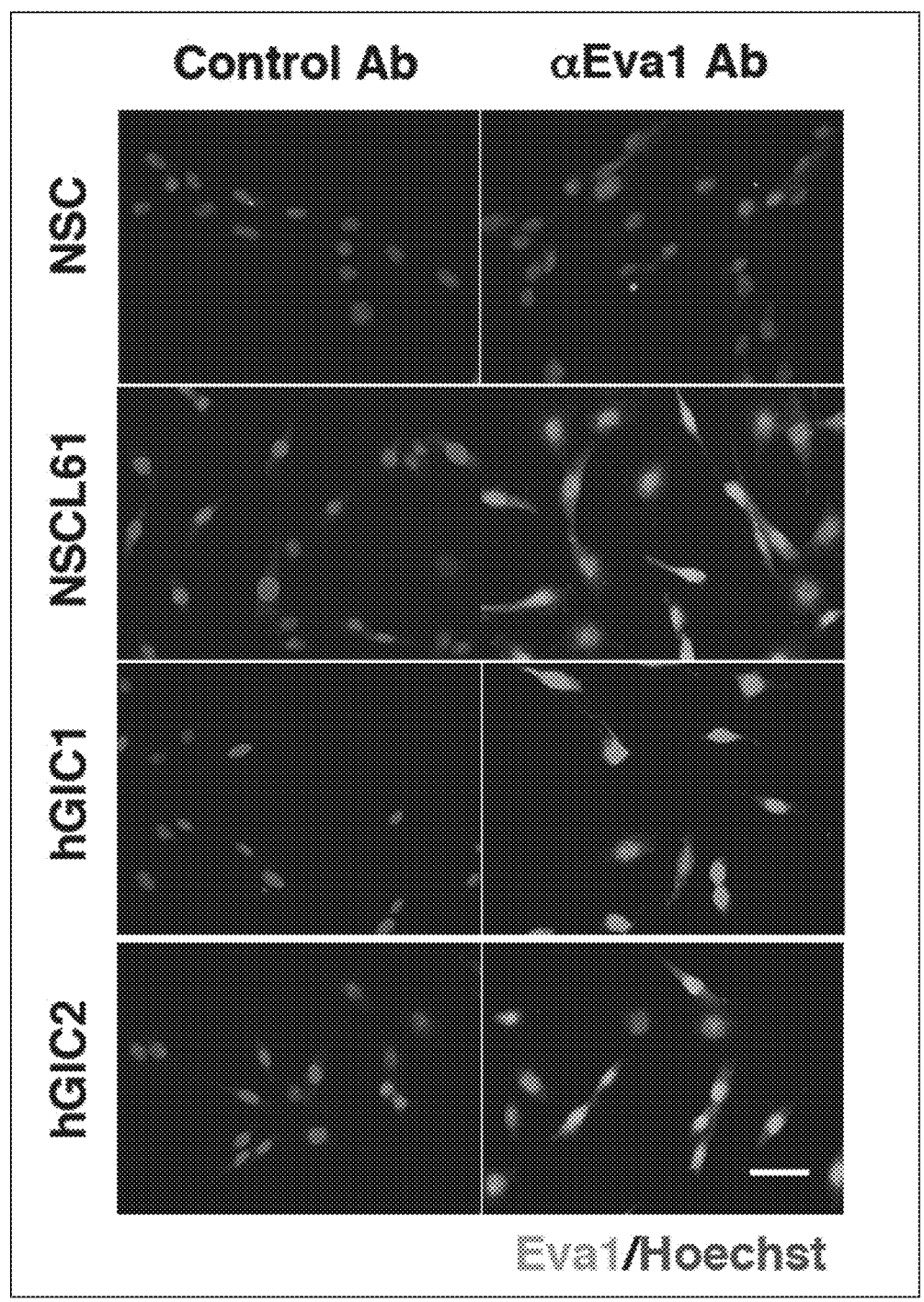
FIG. 4 shows micrographs for illustrating the immunostaining analysis result on an expression of an Eva1 protein in NSCL61 and hGICs. Note that a portion exhibiting green fluorescence in the figure indicates a site stained with the anti-Eva1 antibody, and a portion exhibiting blue fluorescence in the figure indicates a nucleus in the cell subjected to counter staining using Hoechst 33342. Moreover, in the figure, the scale bar represents 50 µm.
Figure 5:
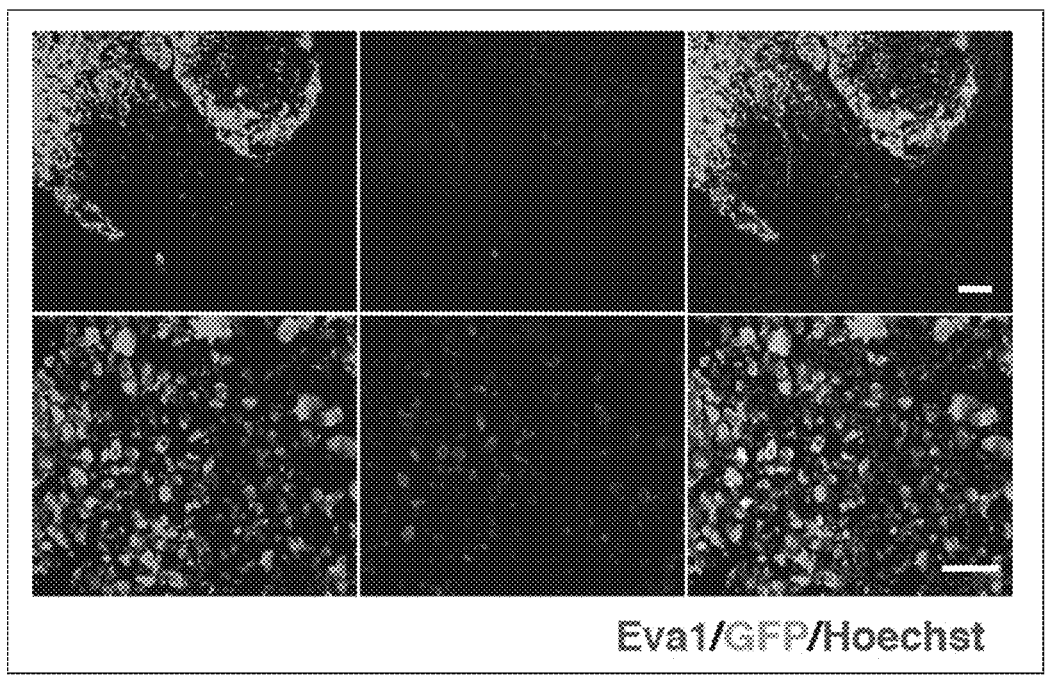
FIG. 5 shows micrographs for illustrating the immunostaining analysis result on an expression of an Eva1 protein in NSCL61-derived tumors. Note that a portion exhibiting red fluorescence in the figure indicates a site stained with the anti-Eva1 antibody (see two panels in the middle), a portion exhibiting green fluorescence in the figure indicates an expression of GFP (see two panels on the left), and a portion exhibiting blue fluorescence in the figure indicates a nucleus in the cell subjected to counter staining using Hoechst 33342. Moreover, in the figure, the scale bar represents 200 µm. Note that since GFP has been incorporated into a vector introduced to establish NSCL61, the expression indicates NSCL61 or cells derived from NSCL61.
Figure 6:
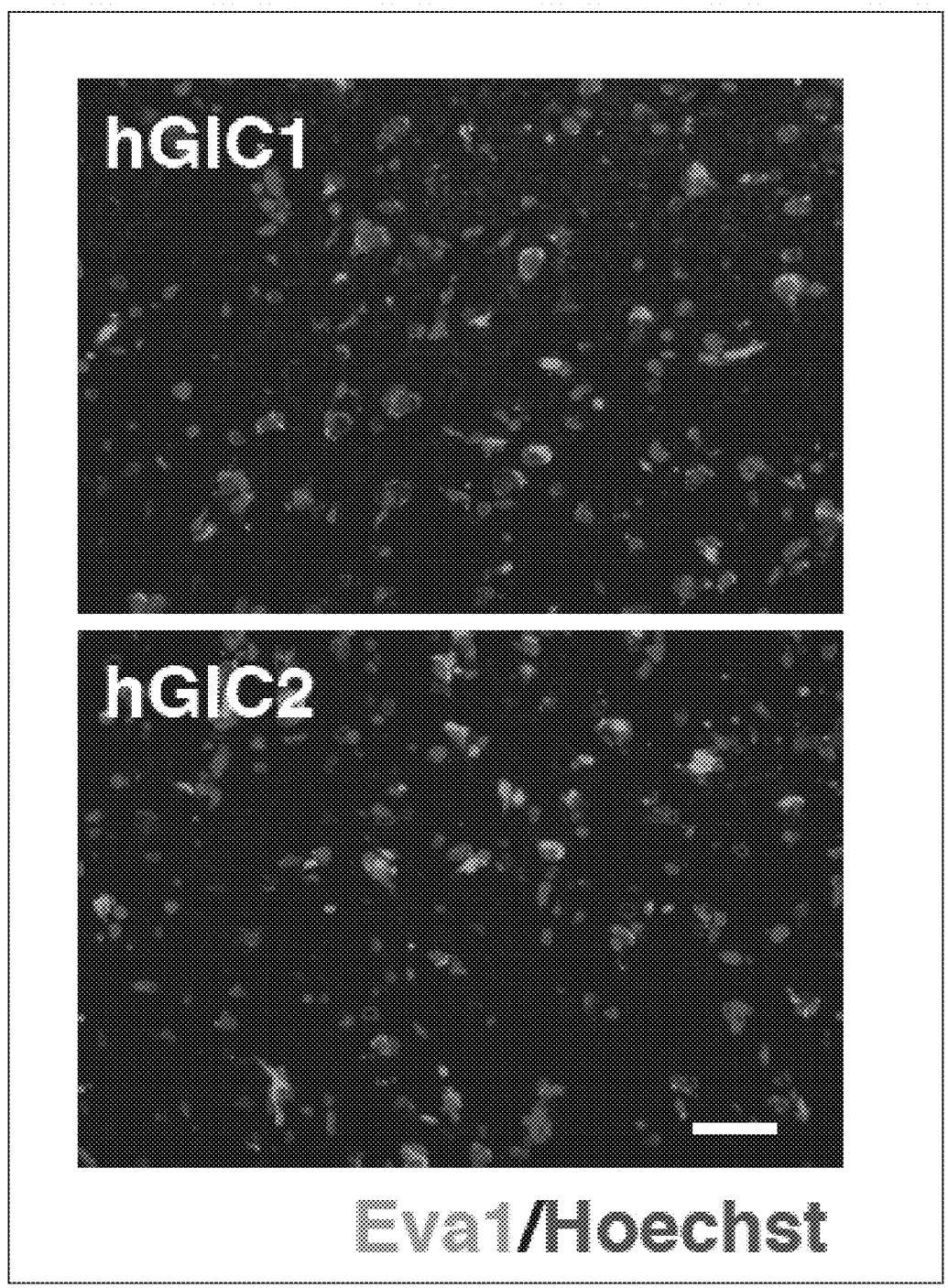
FIG. 6 shows micrographs for illustrating the analysis result on an expression of an Eva1 protein in hGIC-derived xenograft tumors. Note that a portion exhibiting green fluorescence in the figure indicates a site stained with the anti-Eva1 antibody, and a portion exhibiting blue fluorescence in the figure indicates a nucleus in the cell subjected to counter staining using Hoechst 33342. Moreover, in the figure, the scale bar represents 50 µm.
Figure 7:
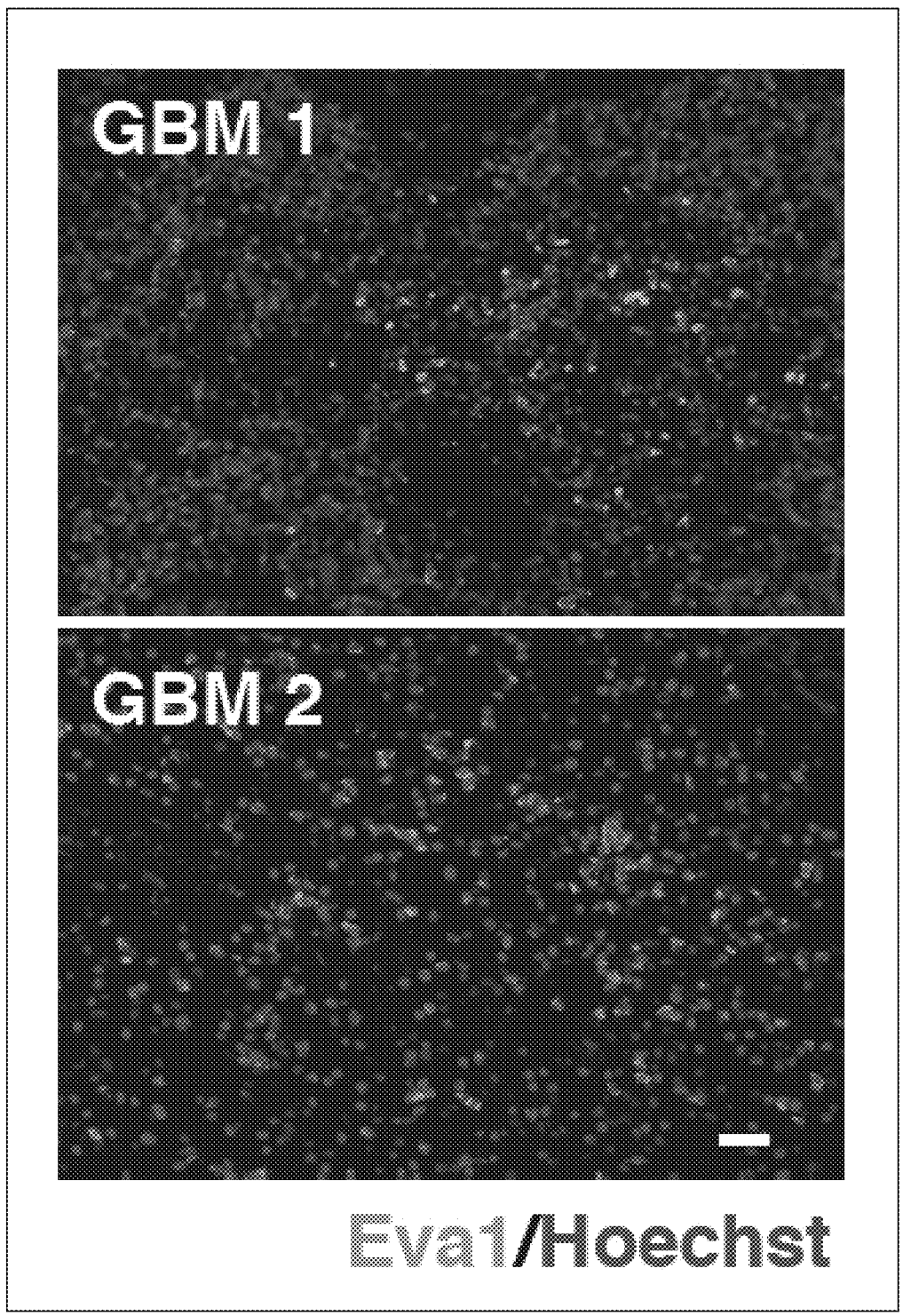
FIG. 7 shows micrographs for illustrating the immunostaining analysis result on an expression of an Eva1 protein in a glioma tissue primary GBM (primary glioblastoma multiforme). Note that a portion exhibiting green fluorescence in the figure indicates a site stained with the anti-Eva1 antibody, and a portion exhibiting blue fluorescence in the figure indicates a nucleus in the cell subjected to counter staining using Hoechst 33342. Moreover, in the figure, the scale bar represents 50 µm.

Moreover, in order to examine an expression of Eva1 at a protein level in these cells, immunostaining was carried out using the anti-Eva1 antibody. FIG. 4 shows the obtained result. Further, in order to examine an expression of Eva1 at a protein level in a glioma formed by transplanting NSC61 or hGIC into the nude mouse brain, immunostaining was carried out using the anti-Eva1 antibody. FIGS. 5 and 6 show the obtained result. Additionally, in order to examine an expression of Eva1 at a protein level in a human-derived primary GMB tissue, immunostaining was carried out using the anti-Eva1 antibody. FIG. 7 shows the obtained result.

Figure 8:
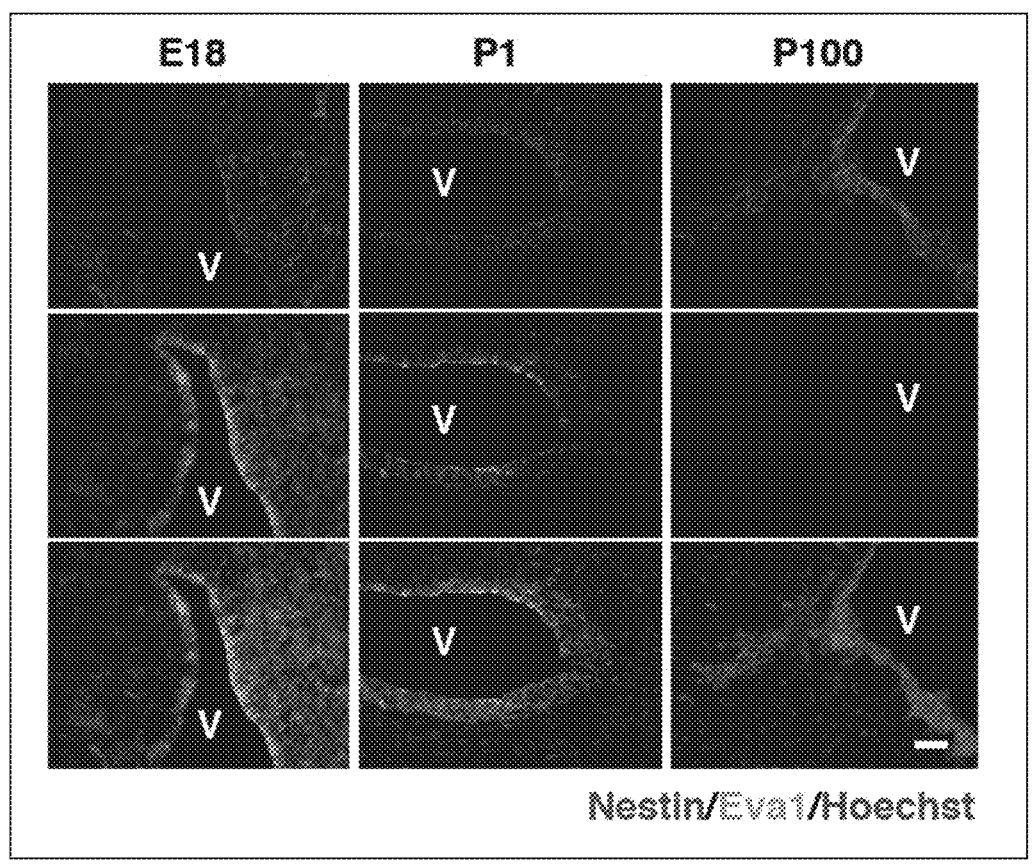
FIG. 8 shows micrographs for illustrating the immunostaining analysis result on an expression of an Eva1 protein in the sagittal sections of mouse brains (at embryonic day 18 (E18), postnatal day 1 (P1), postnatal day 100 (P100)). A portion exhibiting green fluorescence in the figure indicates an expression of Eva1 (see three panels in the second row from the top), a portion exhibiting red fluorescence in the figure indicates an expression of Nestin (see upper three panels), and a portion exhibiting blue fluorescence in the figure indicates a nucleus in the cell subjected to counter staining using Hoechst 33342. Moreover, in the figure, "V" indicates a ventricule, and the scale bar represents 50 µm.

Furthermore, in order to examine an expression of Eva1 at a protein level in the developmental process of the mouse brain, immunostaining was carried out on the sagittal sections of mouse brains (at embryonic day 18 (E18), postnatal day 1 (P1), postnatal day 100 (P100)) using the anti-Eva1 antibody and an anti-Nestin (marker protein of neural stem cells) antibody. FIG. 8 shows the obtained result.

As apparent from the result shown in FIG. 3, eva1 was expressed in the mouse-derived glioma stem cells (NSCL61, OPCL61) and in the human-derived glioma stem cells (hGIC1, hGIC2), but not expressed in OPC and NB. The expression was observed only at quite a low level in NSC as well. Moreover, as apparent from the result shown in FIG. 4, Eva1 was expressed in the mouse-derived glioma stem cells (NSCL61) and in the human-derived glioma stem cells (hGIC1, hGIC2), but the expression was observed only at quite a low level in the normal cells (NSC).

Further, as apparent from the result shown in FIGS. 5 to 7, the expression of Eva1 was observed in the glioma stem cell-derived tumor tissues formed in the nude mouse brains and in the human-derived primary GMB tissues as well. Particularly, in the NSCL61-derived tumor tissue, cells expressing Eva1 at high level were observed more in the peripheral portion of the tumor than in the entire tumor tissue.

In addition, the result shown in FIG. 8 revealed that the Eva1 expression was detected locally in the neural stem cells in the brain at the developmental stages (E18, P1), but the expression disappeared in the brain of the adult (P100). This seems contradicting with the results shown in FIGS. 3 and 4. However, the NSCs used in FIGS. 3 and 4 were cultured in the test tubes for an extended period (3 months or longer). Hence, presumably the Eva1 expression in the NSCs used in FIGS. 3 and 4 was reduced as in the case of the neural stem cells in the brain of the adult (P100) shown in FIG. 8.

Example 3

<Expression of Eva1 in Glioma Tissues and Glioma Cell Lines>

Next, in order to examine the expression of Eva1 in a glioma tissue revealed in Example 2 in detail, RT-PCR was carried out to examine an expression of Eva1 at an mRNA level in glioma tissues removed by surgical operation. Note that the glioma tissues examined were as follow:

GBM: glioblastoma multiforme (grade 4 according to the WHO diagnostic criteria);
AO: anaplastic oligodendroglioma (grade 3 according to the WHO diagnostic criteria);
AOA: anaplastic oligo-astrocytoma (grade 3 according to the WHO diagnostic criteria); and
OLI: oligodendroglioma (grade 2 according to the WHO diagnostic criteria).

Figure 9:
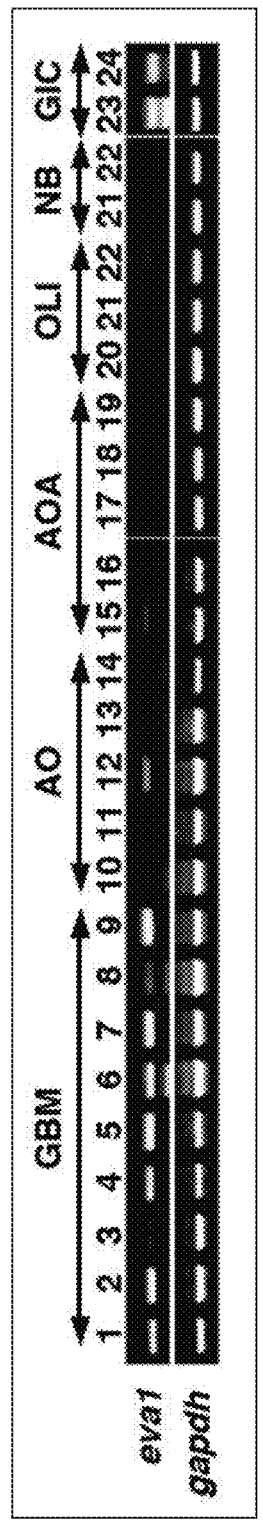
FIG. 9 shows photographs of electrophoreses for illustrating the RT-PCR analysis result on an expression of Eva1 in human primary glioma tissues and human glioma stem cells. Note that the expression of a gapdh gene was used as an internal standard.

Moreover, in addition to the glioma tissues, normal brain tissues (NB: Normal brain or CB: Control human brain) and the hGICs used in Example 2 were also subjected to RT-PCR. FIG. 9 shows the obtained result.

Furthermore, in order to examine an expression of Eva1 at an mRNA level in human GEM-derived glioma cell lines and a rat glioma cell line, RT-PCR was carried out. Note that the glioma cell lines examined were as follow:

T98G: human glioma cells (see Stein, et al., J. Cell. Physiol., 1979, vol. 99, pp. 43 to 54);
Tp483: human glioma cells (see Law, et al., Cancer Genet Cytogenet., 2005, vol. 160, pp. 1 to 14);
SF126: human glioma cells (see Rosenblum, et al., Pharmacol., 1981, vol. 6, pp. 227 to 235);
U87: human glioma cells (see Clark, et al., PLoS Genetics, 2010, vol. 6, iss. 1, e1000832);
U251: human glioma cells (see Signer, et al., Exp. Neurol., 1981, vol. 40, pp. 201 to 229); and
C6: rat glioma cells (see Benda, et al., Science, 1968, vol. 161, pp. 370 to 371).

Figure 10:
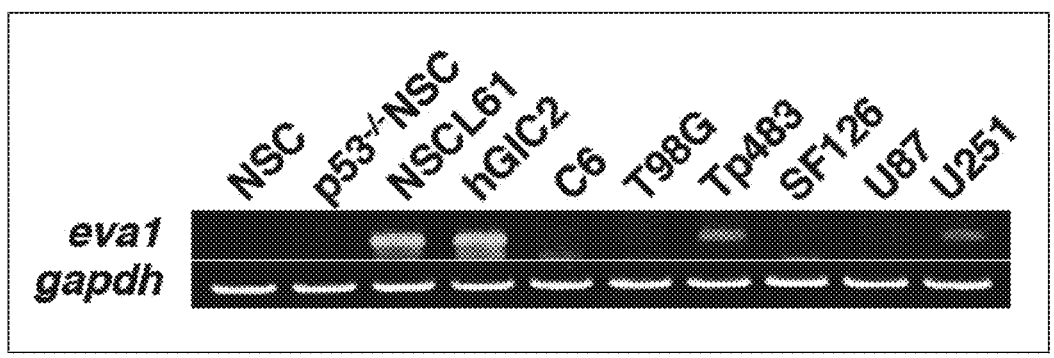
FIG. 10 is a photograph of electrophoreses for illustrating the RT-PCR analysis result on an expression of Eva1 in glioma cell lines. Note that the expression of a gapdh gene was used as an internal standard.

Furthermore, in addition to the glioma cell lines, NSC, NSCL61, and hGIC2 used in Example 2 as well as p53-/- NSC (p53-deficient neural stem cells) from which NSCL61 was obtained were also subjected to RT-PCR. FIG. 10 shows the obtained result.

As apparent from the results shown in FIGS. 9 and 10, eva1 was expressed inmost of the examined GMB tissues, and the eva1 expression was also observed in some of the GBM-derived glioma cell lines.

Example 4

<Expression of Eva1 in Glioma Stem Cells and Glioma Cell Lines>

Figure 11:
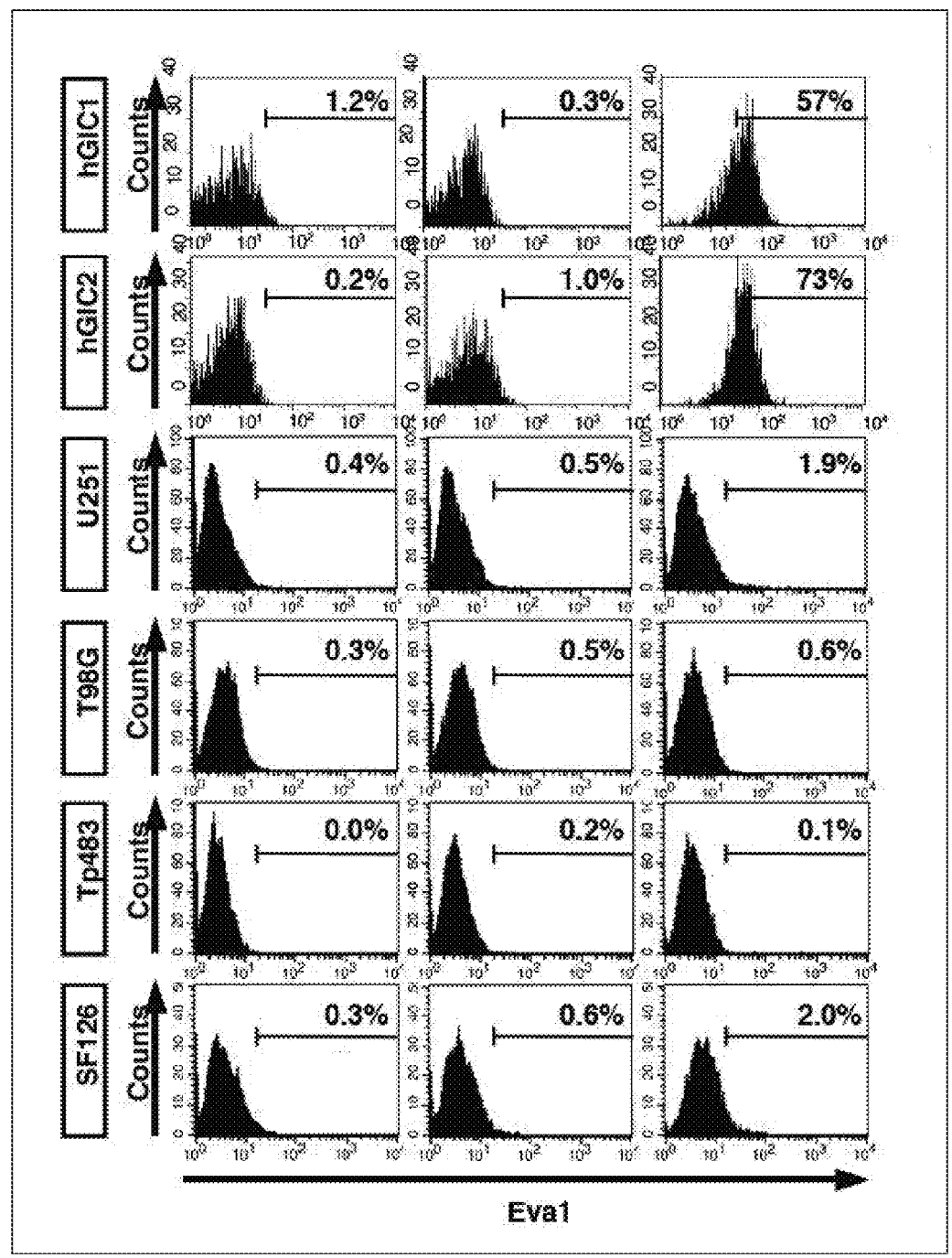
FIG. 11 shows graphs for illustrating the result of immunostaining Eva1 in hGICs and glioma cell lines, which was analyzed by flow cytometry. The left side in the figure illustrates the result of those obtained by reacting each cell type with only a secondary antibody ALEXA FLUOR® 568 (Alexa 568-labeled goat-derived anti-rabbit IgG antibody), the middle in the figure illustrates the result of those obtained by reacting each cell type with only a control antibody (rabbit IgG), and the right side in the figure illustrates the result of those obtained by reacting each cell type with the anti-Eva1 antibody and the secondary antibody.

Next, in order to examine an expression of Eva1 at a protein level in human glioma stem cells and human glioma cell lines, a FACS analysis was carried out using the anti-Eva1 antibody. Note that, as negative controls, those obtained by reacting each cell type with only the secondary antibody ALEXA FLUOR® 568 (Alexa 568-labeled goat-derived anti-rabbit IgG antibody) and those obtained by reacting each cell type with only a control antibody (rabbit IgG) were prepared and analyzed by FACS. FIG. 11 shows the obtained result.

As apparent from the result shown in FIG. 11, a strong Eva1 expression was observed in the human glioma stem cells (hGIC1 and hGIC2). However, in the glioma cell lines, no Eva1 expression was detected by FACS.

Note that it is known that generally even if a glioma cell line is transplanted into a brain, the same pathological findings as those from an actual brain tumor cannot be found; meanwhile, pathological findings similar to those from an actual brain tumor can be easily found from glioma stem cells.

Thus, it is conceivable that Eva1 not expressed in normal tissues of an adult brain but expressed at high level in glioma stem cells and glioma tissues (particularly GBM) as described in Examples 2 to 4 can be utilize not only as a marker of gliomas but also as a treatment target for these. It is also conceivable that because of such a specific expression, particularly high level expression in GBM, Eva1 can also be utilized for a prognosis of glioma patients (predicting the survival rate and survival time after operation on the glioma patients). The following Examples verified these possibilities.

Example 5

<Inhibition of Glioma Stem Cells from Forming Tumor Cell Mass by Anti-Eva1 Antibody>

Figure 12:
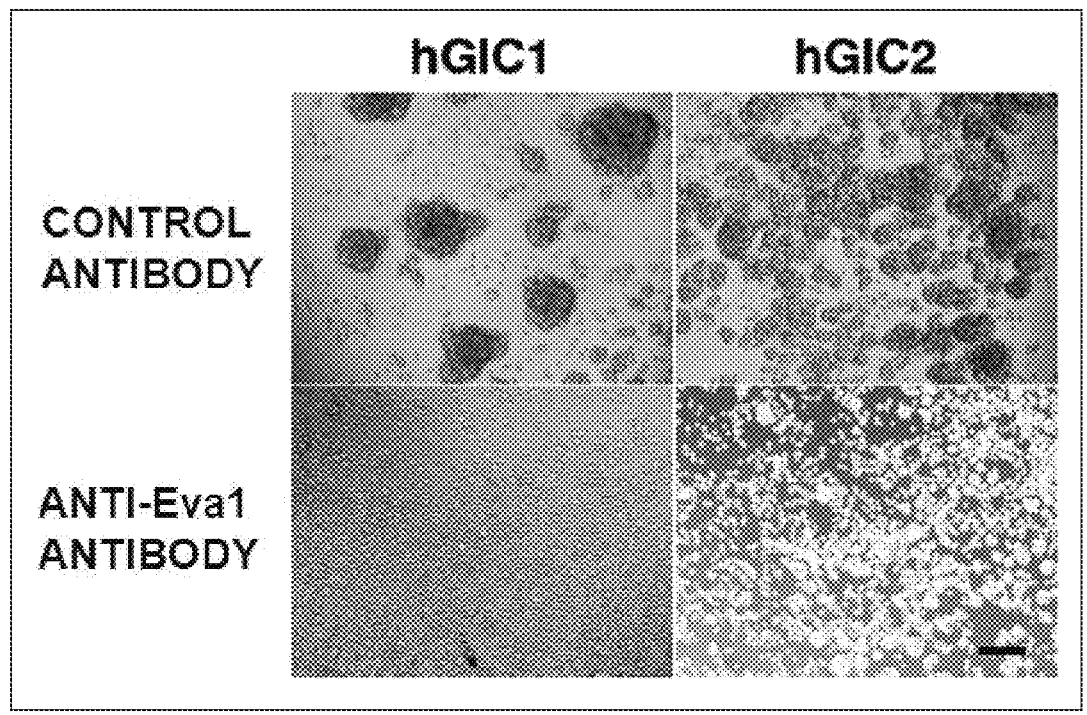
FIG. 12 shows micrographs for illustrating suppression of tumor cell mass (sphere) formation by the anti-Eva1 antibody. In the figure, the scale bar represents 200 µm.

It is known as a characteristic of glioma stem cells that glioma stem cells form a nonadherent tumor cell mass (sphere) when cultured in a serum-free medium (see Vescovi, et al., Nature Reviews CANCER, June 2006, vol. 6, no. 6, pp. 425 to 436). For this reason, the influence of the anti-Eva1 antibody on tumor cell mass formation of glioma stem cells was examined. Specifically, hGIC1 or hGIC2 was cultured for 5 days in a NSC medium (serum free) supplemented with 10 µg/ml of the anti-Eva1 antibody (or rabbit IgG as the control antibody). After subjected to gentle pipetting, the resulting cell mass was observed with an inverted phase contrast microscope. FIG. 12 shows the obtained result. As apparent from the result shown in FIG. 12, the antibody according to the present invention inhibited tumor cell mass formation of the glioma stem cells.

Example 6

<Cytotoxicity Assay using Anti-Eva1 Antibody>

Figure 13:
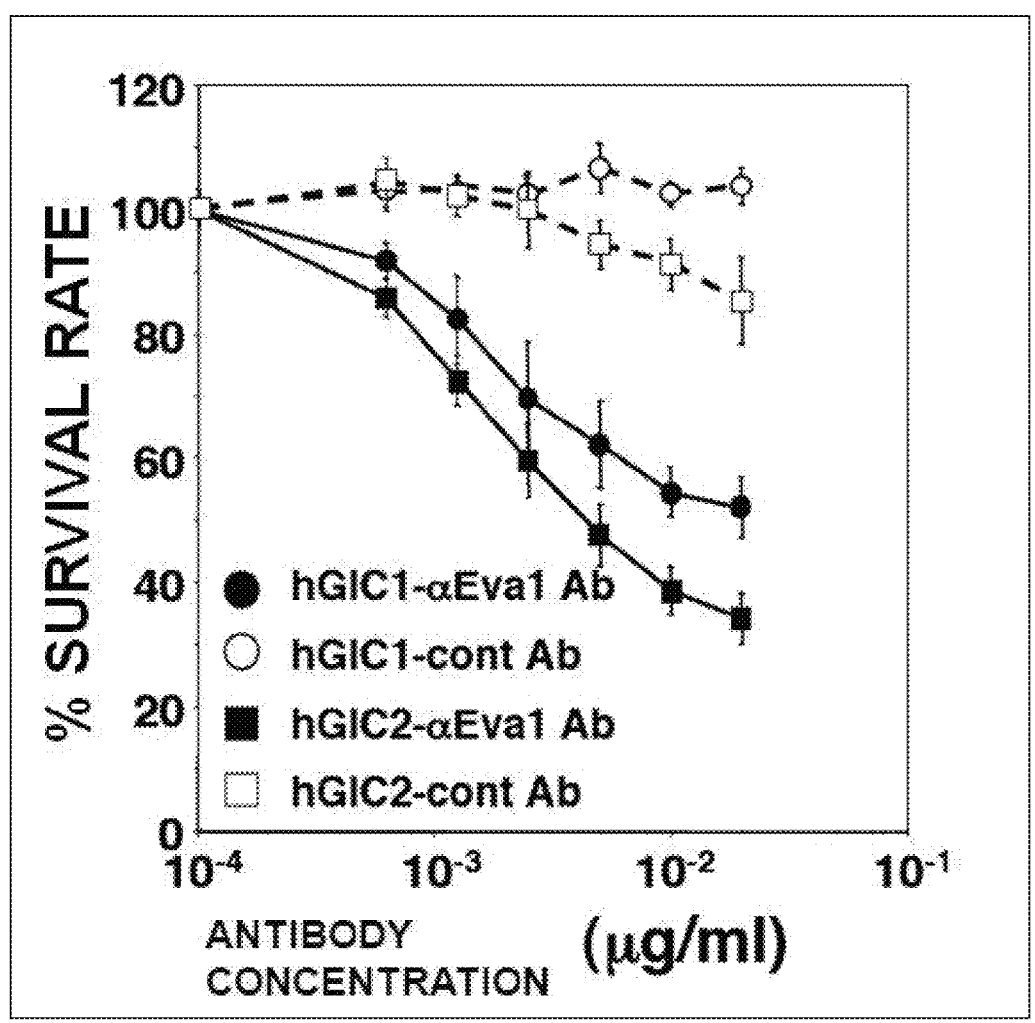
FIG. 13 shows a graph for illustrating the result of a cytotoxicity assay with a combination of the anti-Eva1 antibody and Rab-ZAP. In the figure, "hGIC1-αEva1 Ab" shows the result of adding the anti-Eva1 antibody and Rab-ZAP to hGIC1, and "hGIC2-αEva1 Ab" shows the result of adding the anti-Eva1 antibody and Rab-ZAP to hGIC2. Moreover, "hGIC1-cont Ab" shows the result of adding the control antibody (rabbit IgG) and Rab-ZAP to hGIC1, and "hGIC2-cont Ab" shows the result of adding the control antibody (rabbit IgG) and Rab-ZAP to hGIC2.

In order to verify whether or not the antibody according to the present invention was usable in a delivery method to a glioma, a cytotoxicity assay was carried out using Rab-ZAP. FIG. 13 shows the obtained result. Note that Rab-ZAP is an anti-rabbit IgG antibody conjugated with a ribosome inactivating protein, saporin. Hence, when rabbit IgG binding to a cell is conjugated with Rab-ZAP, saporin is introduced into the cell, causing cell death.

As apparent from the result shown in FIG. 13, the survival rates of hGIC1 and hGIC2 were lower in the cell media to which the anti-Eva1 antibody (αEva1Ab) and Rab-ZAP were added than in the cell media to which the control antibody (cont Ab) and Rab-ZAP were added. In addition, the survival rates were lowered in a manner dependent to the concentration of the antibody added.

Thus, it was demonstrated that the antibody according to the present invention was usable in a method for delivering a desired substance (for example, Rab-ZAP) to a glioma.

Example 7

<Verification of Effect of Suppressing Cell Proliferation and Tumor Formation of Glioma Stem Cells by shRNA Targeting Eva1 Gene>

Figure 14:
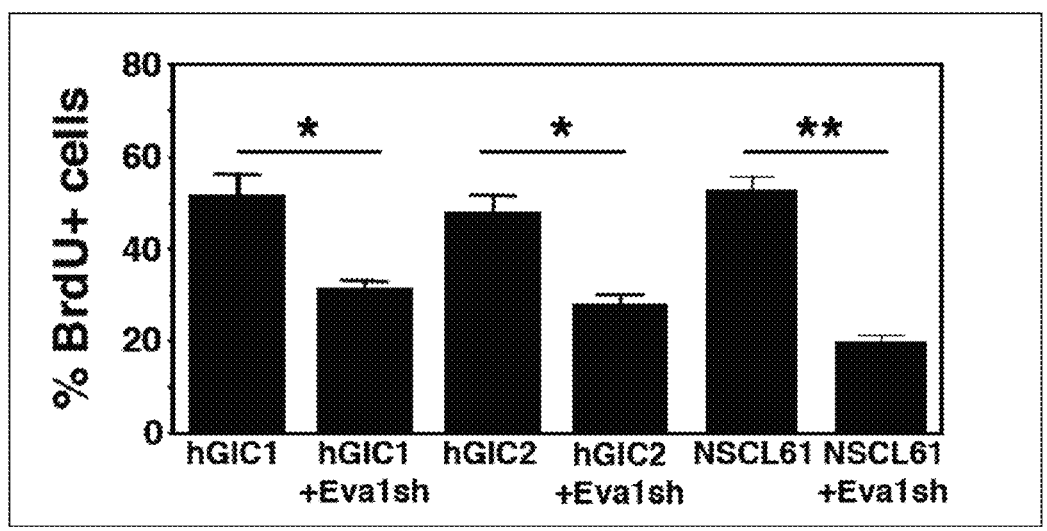
FIG. 14 shows a graph for illustrating that the proliferations of human and mouse glioma stem cells were reduced by expressing a shRNA targeting the Eva1 gene (Eva1sh). In the figure, the vertical axis represents a ratio (%) of cells incorporating 5-bromo-2'-deoxyuridine (BrdU) (BrdU+ cells). One asterisk indicates $p<0.05$, and two asterisks indicate $p<0.001$, in comparison with glioma stem cells (hGIC1, hGIC2, or NSCL61) expressing control shRNA.
Figure 15:
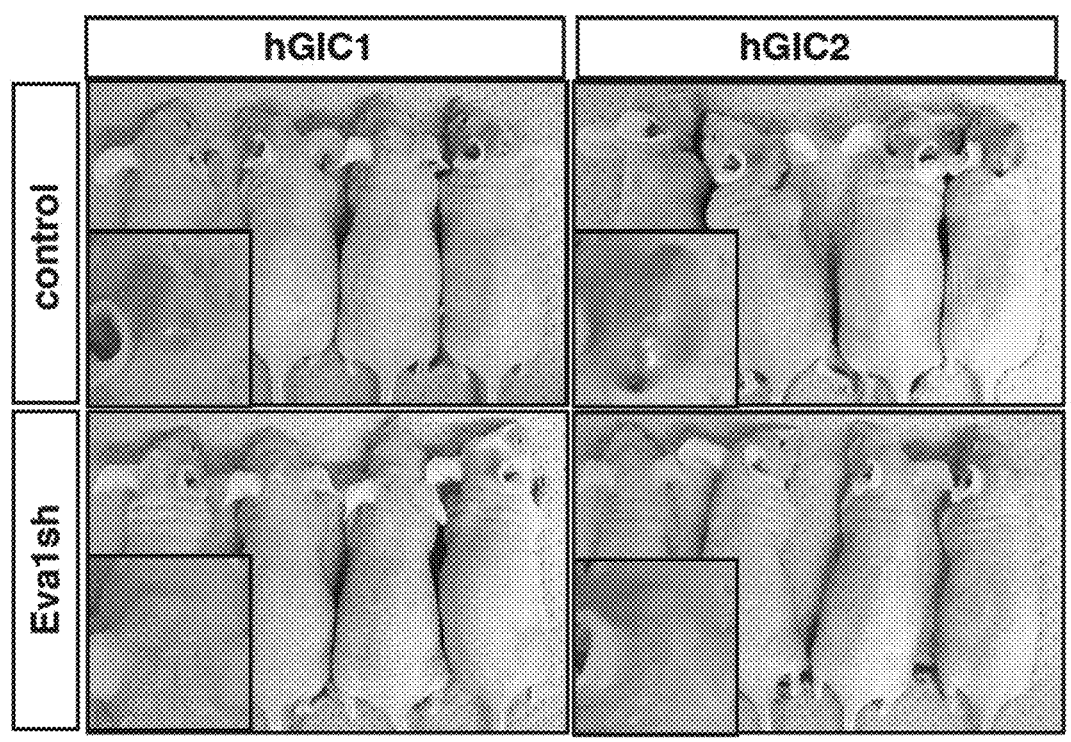
FIG. 15 shows photographs of mice for illustrating that in vivo Eva1sh expression reduced tumor formation of hGICs.
Figure 16:
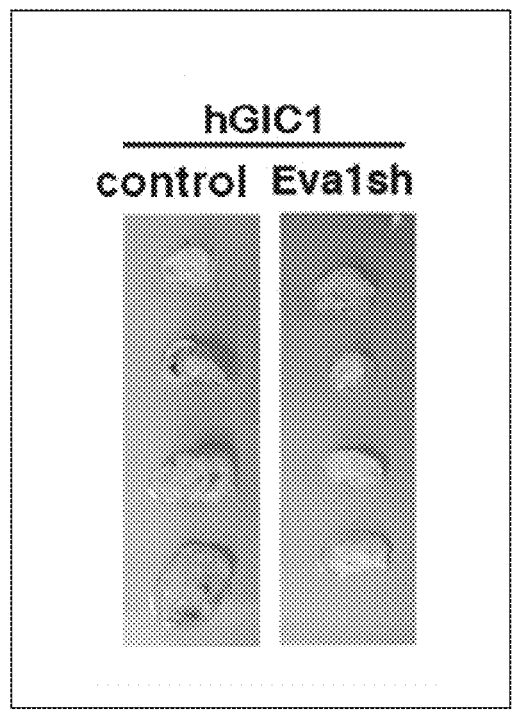
FIG. 16 shows photographs of hGIC1-derived xenograft tumors expressing Eva1sh or control shRNA.
Figure 17:
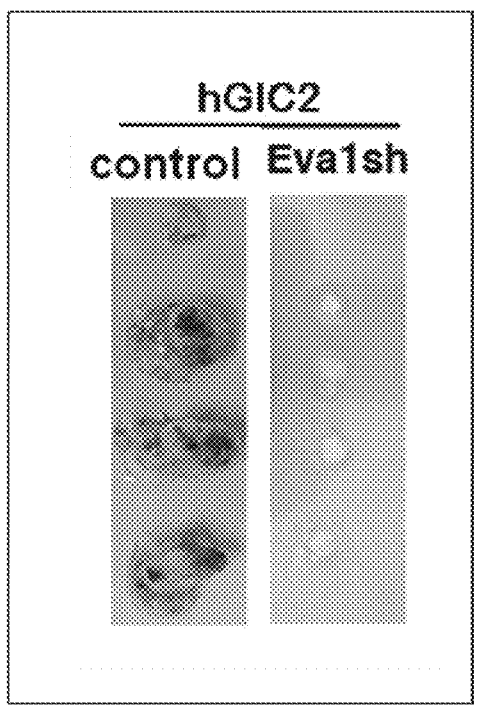
FIG. 17 shows photographs of hGIC2-derived xenograft tumors expressing Eva1sh or control shRNA.
Figure 18:
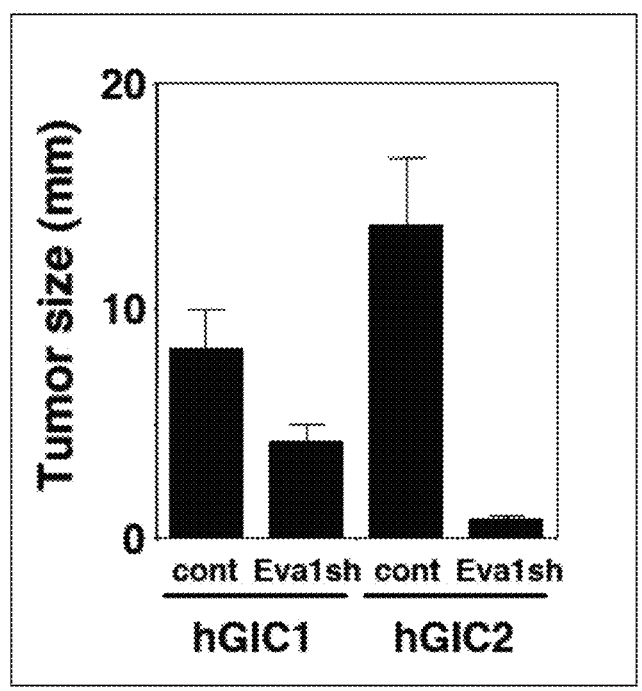
FIG. 18 shows a graph for illustrating the result of measuring the size (major axis) of the hGIC-derived xenograft tumors expressing Eva1sh or control shRNA. In the figure, "cont" shows the result of the hGIC-derived xenograft tumors expressing control shRNA, and "Eva1sh" shows the result of the hGIC-derived xenograft tumors expressing the shRNA targeting the Eva1 gene.

Verified was whether or not an RNA (Eva1shRNA) capable of binding to a transcription product of the Eva1 gene according to the present invention was able to suppress cell proliferation of glioma stem cells by knocking down an expression of an Eva1 protein. Specifically, the cell proliferation of human-derived or mouse-derived glioma stem cells into which Eva1shRNA (psiRNA-h7SKhygro-meva1sh or psiRNA-h7SKhygro-hEva1sh) was introduced was evaluated based on a ratio (%) of cells incorporating 5-bromo-2'-deoxyuridine (BrdU) (BrdU+cells). FIG. 14 shows the obtained result.

Moreover, verified was whether or not Eva1shRNA (Eva1sh) was able to suppress tumor formation of glioma stem cells. Specifically, human glioma stem cells constantly expressing Eva1shRNA were transplanted into nude mouse brains (intracranial cell transplantation). Tumors formed in the brains were observed, and the size was measured 20 days after the transplantation. Note that, as a control, human glioma stem cells constantly expressing the shRNA targeting an EGFP gene were intracranially transplanted. FIGS. 15 to 18 show the obtained result.

As apparent from the result shown in FIG. 14, it was shown that in the human-derived glioma stem cells (hGIC1, hGIC2) and the mouse-derived glioma stem cells (NSCL61), the introduction of Eva1shRNA into the cells reduced the ratio of cells incorporating BrdU, in other words, reduced the ratio of proliferative cells.

Further, as apparent from the result shown in FIGS. 15 to 18, in the human-derived glioma stem cells (hGIC1 and hGIC2), the introduction of Eva1shRNA into the cells reduced the size of the resulting tumors in comparison with the case of introducing control shRNA.

Thus, it was revealed that the RNA (Eva1shRNA) capable of binding to a transcription product of the Eva1 gene according to the present invention was able to suppress cell proliferation and tumor formation of glioma stem cells by knocking down an expression of the Eva1 protein to suppress the function thereof.

Example 8

<Verification of Effect of Suppressing Glioma Tissue Invasion by Molecule Capable of Suppressing Function of Eva1 Gene>

Figure 19:
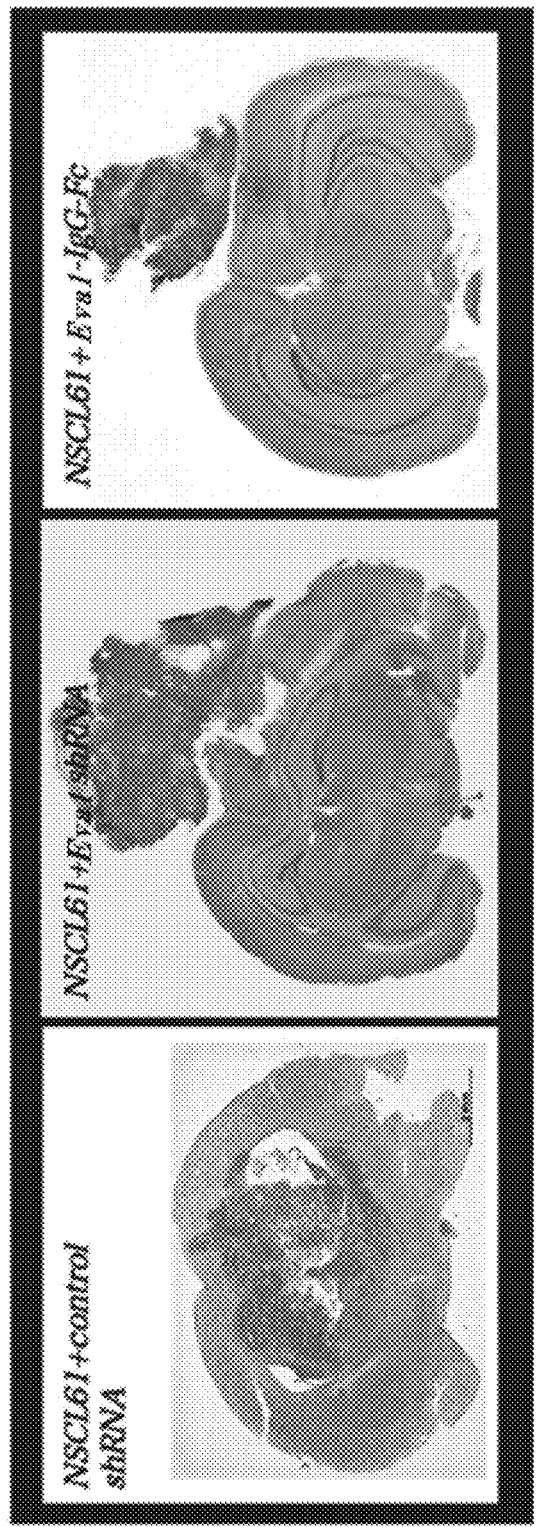
FIG. 19 shows photographs of tumors derived from NSCL61 expressing control shRNA, Eva1shRNA (shRNA targeting the Eva1 gene), or Eva1-IgG-Fc.

Whether or not a molecule capable of suppressing a function of the Eva1 gene according to the present invention was able to suppress glioma tissue invasion was verified using a peptide having a dominant-negative phenotype over the Eva1 protein. Specifically, first, a gene encoding the extracellular region (1st to 150th amino acids in the amino acid sequence of SEQ ID NO: 2) of the Eva1 protein was inserted into a pEF-Fc plasmid vector to prepare a plasmid capable of expressing a fusion protein of the extracellular region of the Eva1 protein with human IgG-Fc (Eva1-IgG-Fc) in a cell (for the pEF-Fc plasmid vector, see "Suda, et al., J Exp Med., 1994, vol. 179, pp. 873 to 879"). Next, this plasmid was introduced into mouse-derived glioma stem cells (NSCL61) to establish a NSCL61 cell line constantly expressing Eva1-IgG-Fc (NSCL61+Eva1-IgG-Fc). Then, obtained cells as the result of the establishment, NSCL61 cells constantly expressing Eva1shRNA (NSCL61+Eva1shRNA), or NSCL61 cells constantly expressing control shRNA (NSCL61+controlshRNA) were intracranially transplanted. Around 3 weeks after the transplantation, tumors formed in the brains were observed. FIG. 19 shows the obtained result.

As apparent from the result shown in FIG. 19, it was observed that the glioma stem cells (NSCL61+controlshRNA) formed invasive GBM in the ventricular systems of all the transplanted mice. Meanwhile, it was revealed that glioma stem cells constantly expressing the molecule capable of suppressing a function of the Eva1 gene (Eva1-IgG-Fc or Eva1shRNA) formed tumors mostly outside the ventricular systems.

Thus, it was revealed that the molecule capable of suppressing a function of the Eva1 gene was able to not only suppress cell proliferation and tumor formation of glioma stem cells, but also suppress GBM tissue invasion.

Example 9

<Correlation between Expression of Eva1 and Survival Rate of Glioma Patients>

Figure 20:
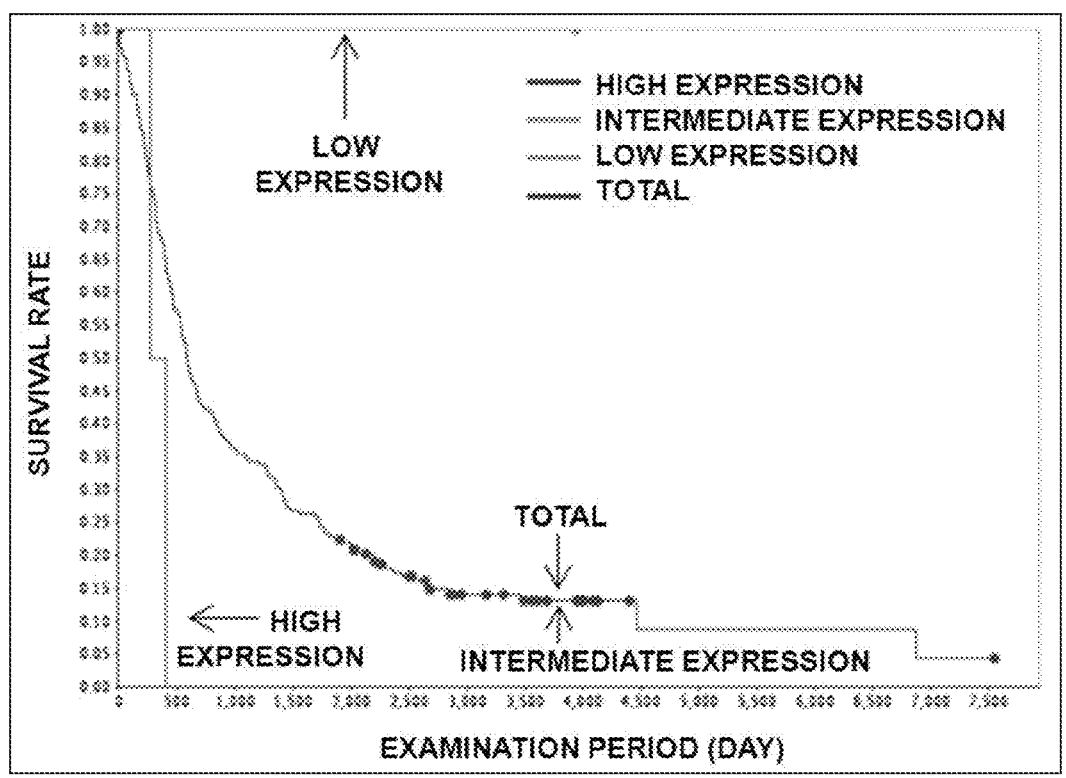
FIG. 20 shows a graph for illustrating the result of examining the relationship between the expression of Eva1 at an mRNA level in gliomas derived from patients and the survival rate of the patients using a brain tumor database REMBRANT (REpository for Molecular BRAin Neoplasia DaTa) of the National Cancer institute of the US. The vertical axis represents "survival rate of glioma patients after operation", and the horizontal axis represents "examination period after operation on glioma patients".

Whether or not a prognosis of glioma patients was possible based on Eva1 expression was verified. Specifically, whether or not there was a correlation between the expression of Eva1 at an mRNA level in gliomas derived from patients and the survival rate of the patients was examined using a brain tumor database REMBRANT (REpository for Molecular BRAin Neoplasia DaTa) of the National Cancer institute of the US. FIG. 20 shows the obtained result.

As apparent from the result shown in FIG. 20, the survival time of the patients with gliomas in which the Eva1 gene was expressed at high level was 500 days or shorter after the prognosis examination was started; meanwhile, the survival rate of the patients in which the Eva1 gene was expressed at low level was as high as 100% at day 4000 after the operation.

Thus, it was revealed that the expression of Eva1 had a strong mutual relation with the survival time and the survival rate of glioma patients. It was demonstrated that detecting Eva1 gene expression was effective in glioma testing, particularly a prognosis of glioma patients.

Example 10

Figure 21:
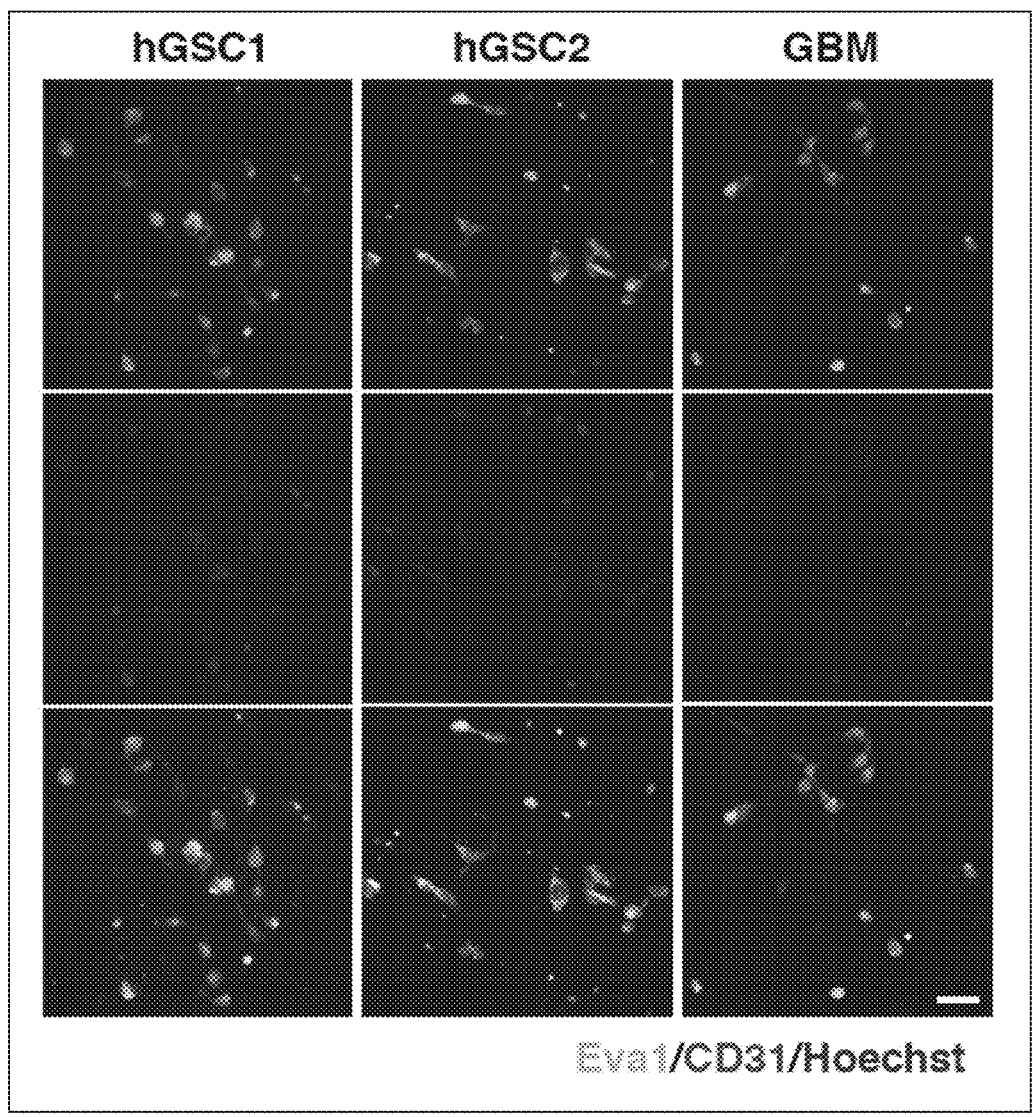
FIG. 21 shows micrographs for illustrating the immunostaining analysis result on expressions of Eva1, CD31, and so forth in hGSCs and human primarily cultured GBM cells. Note that a portion exhibiting green fluorescence in the figure indicates a site stained with the anti-Eva1 antibody (see top three panels), a portion exhibiting red fluorescence in the figure indicates an expression of CD31 (see three panels in the middle), and a portion exhibiting blue fluorescence in the figure indicates a nucleus in the cell subjected to counter staining using Hoechst 33342. Moreover, in the figure, the scale bar represents 100 µm, and bottom three panels are photographs each obtained by superimposing a staining image with the anti-Eva1 antibody, a staining image with an anti-CD31 antibody, and a staining image with Hoechst 33342.
Figure 22:
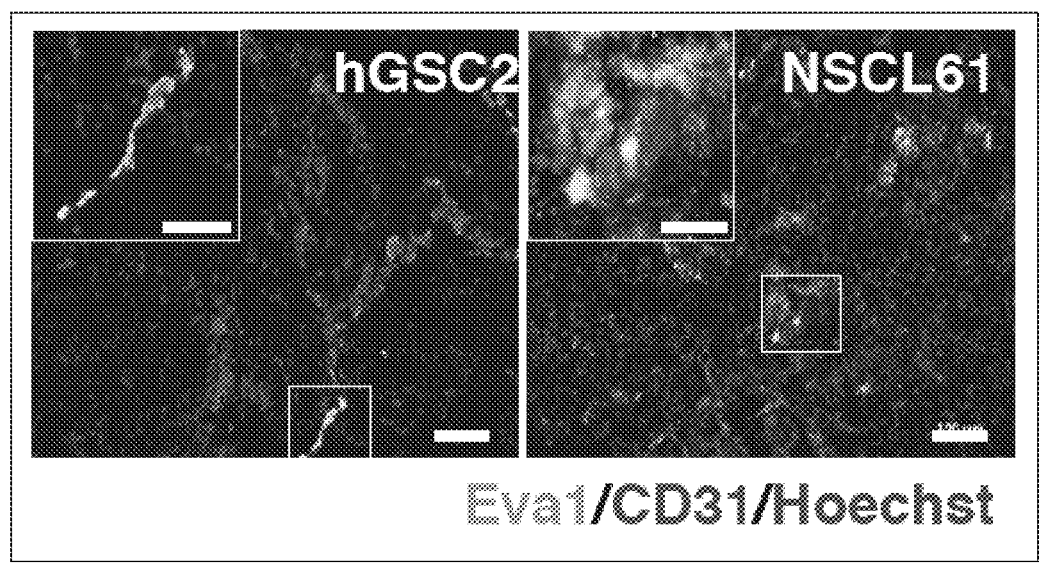
FIG. 22 shows micrographs for illustrating the immunostaining analysis result on expressions of Eva1, CD31, and so forth in NSCL61-derived and hGSC2-derived glioma specimens. Note that a portion exhibiting green fluorescence in the figure indicates a site stained with the anti-Eva1 antibody, a portion exhibiting red fluorescence in the figure indicates an expression of CD31, and a portion exhibiting blue fluorescence in the figure indicates a nucleus in the cell subjected to counter staining using Hoechst 33342. Moreover, in the figure, the scale bar represents 100 µm.

In consideration of such findings that glioma stem cells were capable of transdifferentiation into tumorigenic endothelial cells ("Ricci-Vitiani, L., et al, Nature, 2010, vol. 468, pp. 824 to 828", "Wang, R., et al, Nature, 2010, vol. 468, pp. 829 to 833"), expressions of Eva1 and endothelial cell marker: CD31 in human glioma stem cells (hGSC1 and hGSC2) and human primarily cultured GBM cells were analyzed by the immunostaining method. FIG. 21 shows the obtained result. Moreover, expressions of Eva1 and CD31 in gliomas derived from glioma stem cells (hGSC2 or NSCL61) were analyzed by the immunostaining method. FIG. 22 shows the obtained result.

As apparent from the results shown in FIGS. 21 and 22, it was revealed that the CD31 protein, an endothelial marker, was expressed in the Eva1-positive cells both in vitro (FIG. 21) and in vivo (FIG. 22).

Thus, such a result that CD31 was expressed in the Eva1-positive glioma stem cells (Eva1+ GSC) and findings that glioma stem cells (GSC) transdifferentiate into tumorigenic endothelial cells ("Ricci-Vitiani, L., et al, Nature, 2010, vol. 468, pp. 824 to 828", "Wang, R., et al, Nature, 2010, vol. 468, pp. 829 to 833", "Calabrese, C., et al., Cancer Cell, 2007, vol. 11, pp. 69 to 82") suggest that Eva1+/CD31+ GSC forms a tumor vascular niche useful for maintaining GSC in GBM.

Example 11

Figure 23:
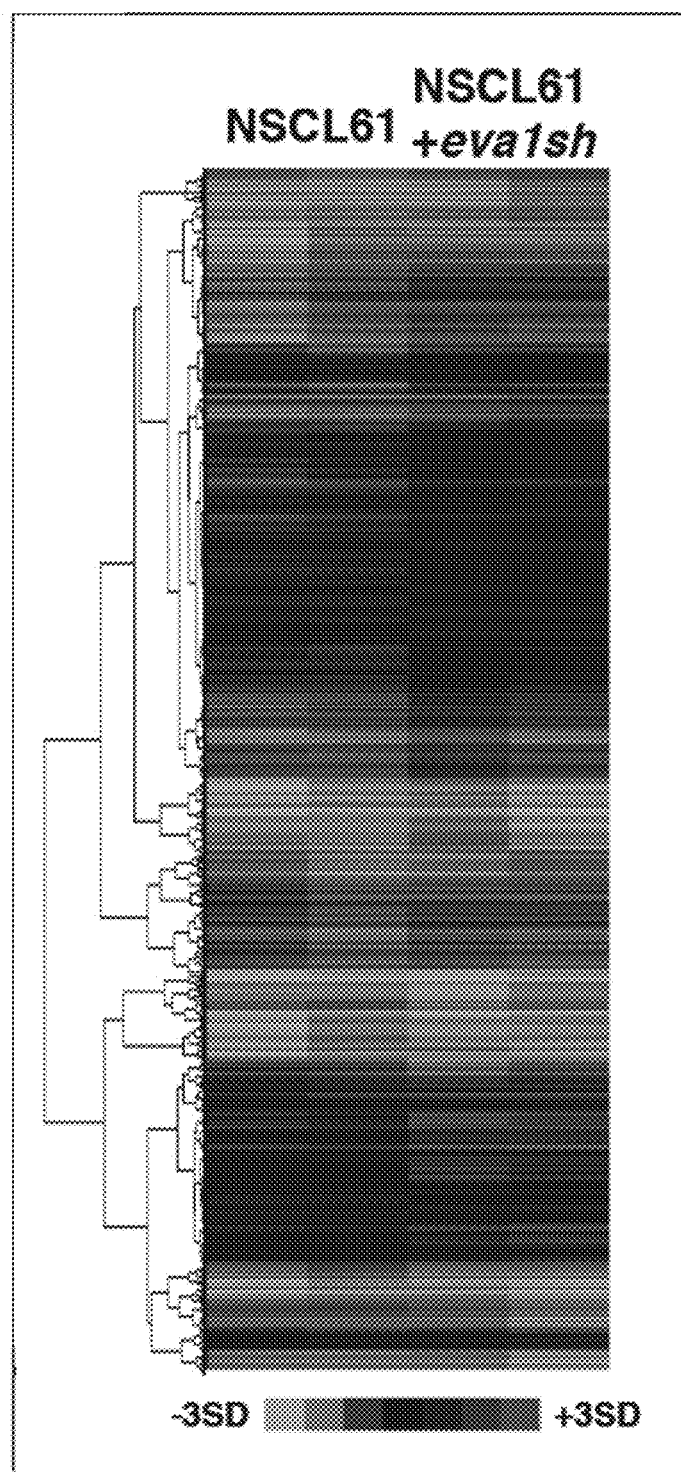
FIG. 23 shows photographs for illustrating the result of hierarchical clustering analysis on NSCL61 and eva1sh-expressing NSCL61 (NSCL61+eva1sh) using TORAY 3D-gene Mouse Oligo Chip 24 k.

Next, in order to examine how Eva1 influenced GSC malignant tumor, a difference in gene expression between NSCL61 and eva1sh-expressing NSCL61 (NSCL61+ eva1sh) was analyzed using DNA microarray. FIG. 23 shows the obtained result.

As a result, it was revealed that in eva1sh-expressing NSCL61, expressions of 1208 genes were promoted and expressions of 650 genes were reduced in comparison with control NSCL61 (FIG. 23). Moreover, it was found out that the gene influenced by eva1-expression suppression the most was ceacam1.

Figure 24:
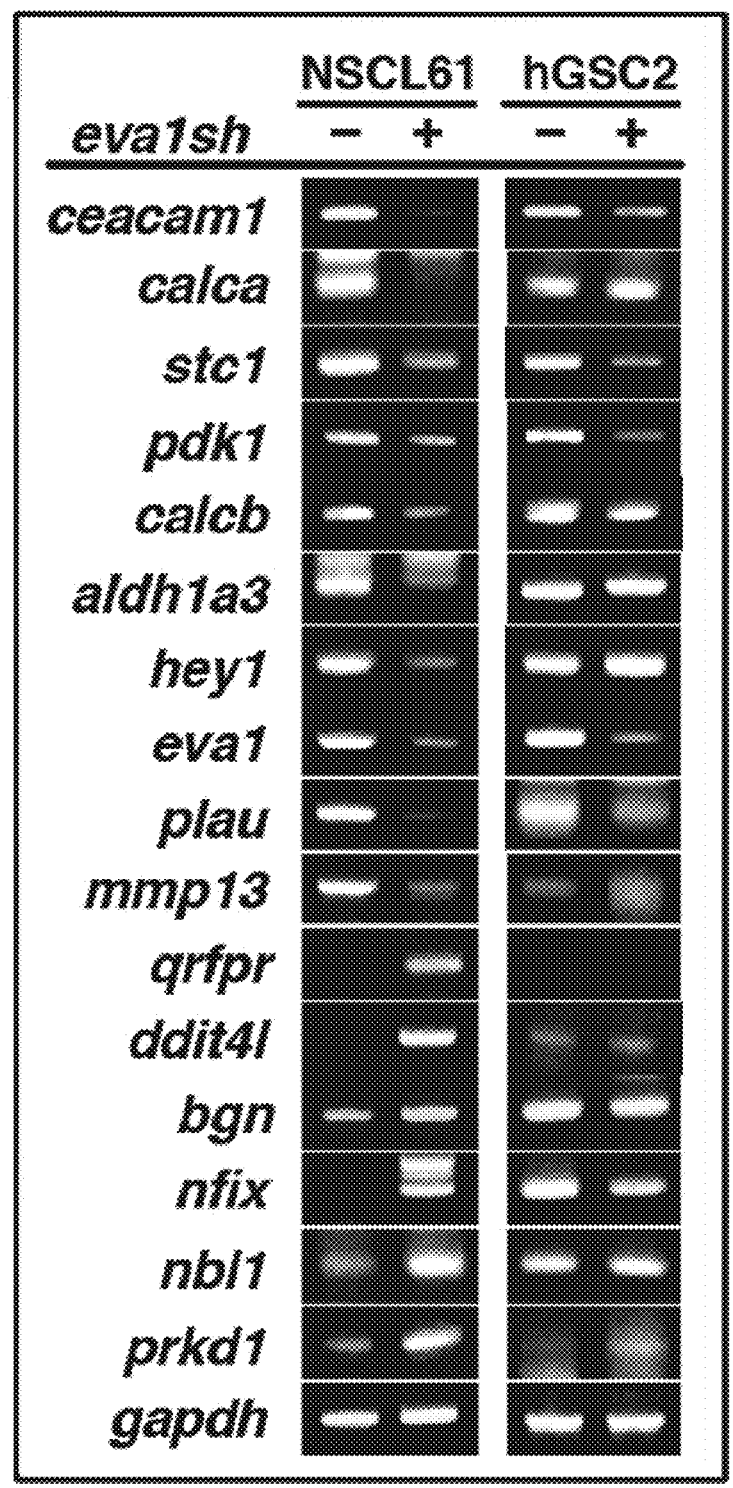
FIG. 24 shows photographs of electrophoreses for illustrating the RT-PCR analysis result on expressions of Ceacam1 gene and so forth in NSCL61, eva1sh-expressing NSCL61, hGSC2, and eva1sh-expressing hGSC2. Note that the expression of a gapdh gene was used as an internal standard. Moreover, "−" indicates cells not expressing eva1sh, and "+" indicates cells expressing eva1sh.

Next, expression patterns of genes, including ceacam1, influenced by eva1sh-expression suppression in NSCL61, hGSC2, and these cells expressing eva1sh were analyzed by RT-PCR. FIG. 24 shows the obtained result.

Figure 25:
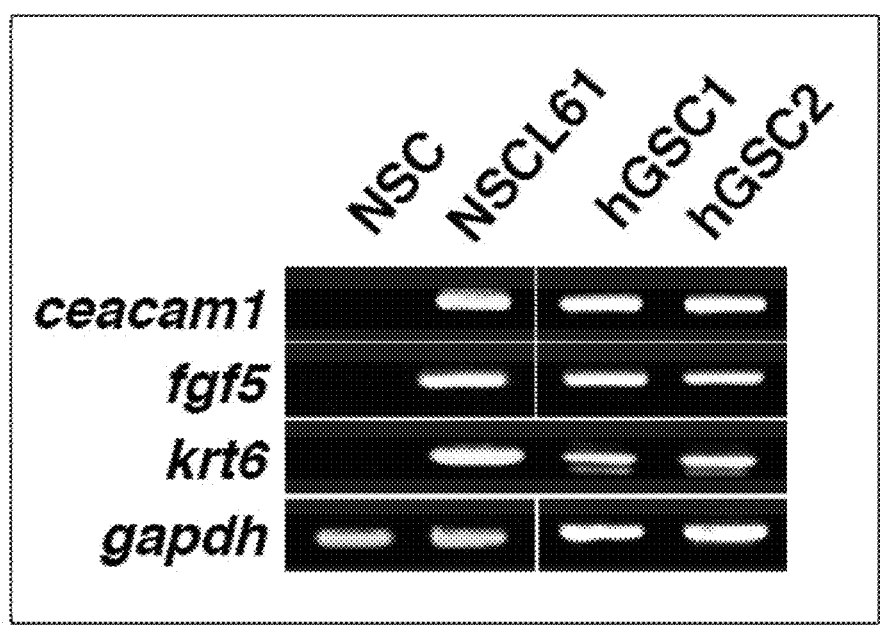
FIG. 25 shows photographs of electrophoreses for illustrating the RT-PCR analysis result on expressions of ceacam1, fgf5, and krt6 in NSC, NSCL61, and hGSCs. Note that the expression of a gapdh gene was used as an internal standard.

Moreover, expressions of ceacam1 and so forth in ceacam1 mouse neural stem cells (NSC) and glioma stem cells (NSCL61, hGSC1, and hGSC2) were analyzed by RT-PCR. FIG. 25 shows the obtained result.

Figure 26:
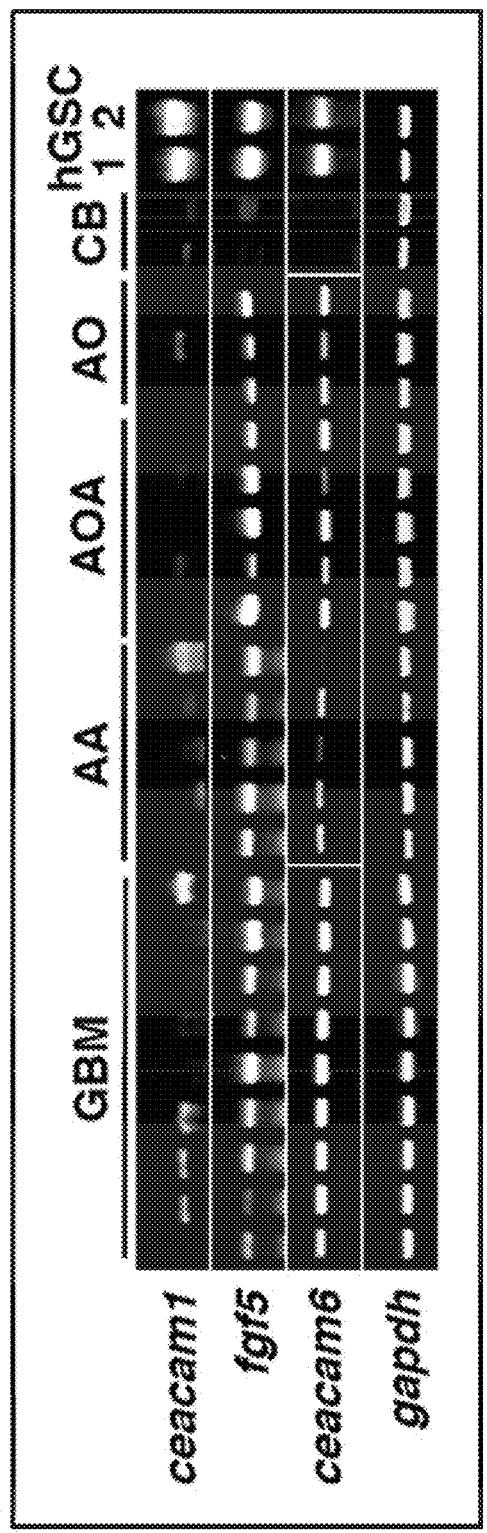
FIG. 26 shows photographs of electrophoreses for illustrating the RT-PCR analysis result on expressions of ceacam1, fgf5, and ceacam6 in human primary gliomas and hGSCs. Note that the expression of a gapdh gene was used as an internal standard.

Further, expressions of ceacam1 and so forth in GBM (glioblastoma multiforme), AA (anaplastic astrocytoma), AOA (anaplastic oligo-astrocytoma), AO (anaplastic oligodendroglioma), CB (normal brain tissues), and hGSCs were analyzed by RT-PCR. FIG. 26 shows the obtained result.

As shown in FIG. 24, the DNA microarray analysis and RT-PCR analysis revealed that the Eva1 knockdown had an influence on expressions of many cancer-associated genes, in addition to Ceacam1, such as pyruvate dehydrogenase kinase isozyme 1 (pdk1), urokinase plasminogen activator (plau), matrix metalloproteinase (mmp13), and protein kinase D1 (prkd1). Additionally, since these factors play essential roles in metastasis, angiogenesis, and cancer cell proliferation, it is suggested that Eva1 adjust malignant property of GSC.

Moreover, as shown in FIGS. 25 and 26, it was revealed that as in the case of Eva1, Ceacam1 was not expressed in normal brain tissues but expressed in glioma stem cells, mainly GBM.

Example 12

Figure 27:
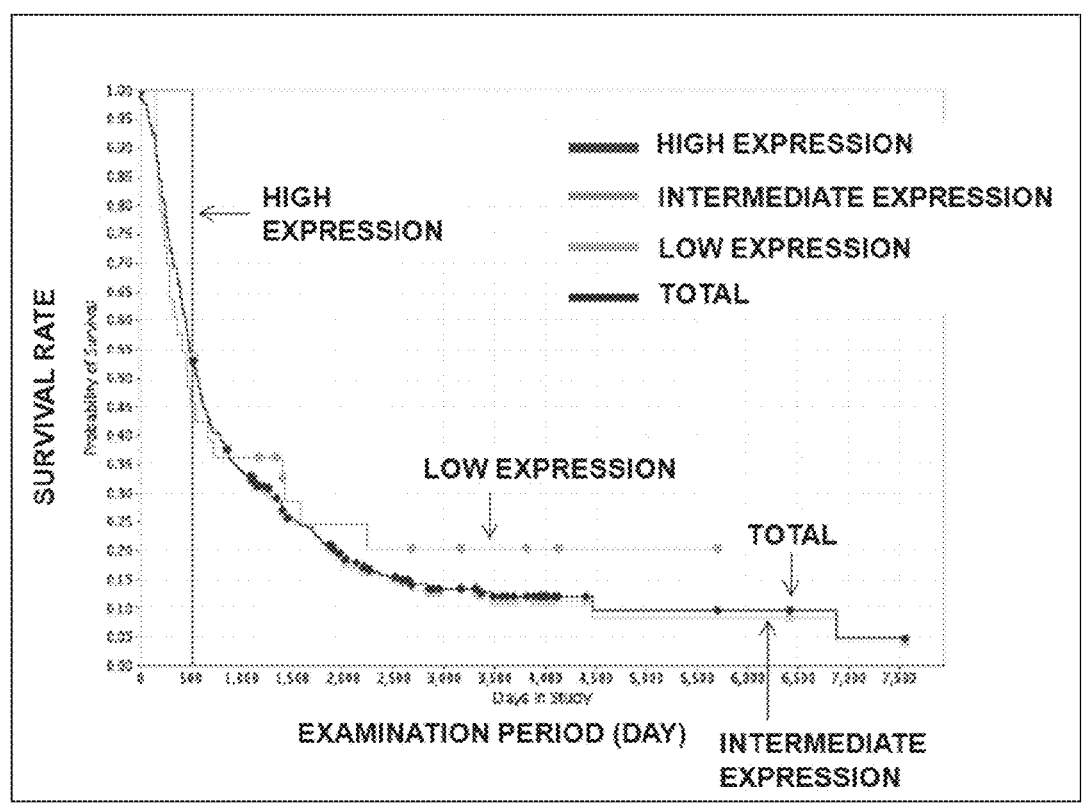
FIG. 27 shows a graph for illustrating the result of examining the relationship between the expression of Ceacam1 at an mRNA level in gliomas derived from patients and the survival rate of the patients using the brain tumor database REMBRANT of the National Cancer institute of the US. The vertical axis represents "survival rate of glioma patients after operation", and the horizontal axis represents "examination period after operation on glioma patients".

Whether or not a prognosis of glioma patients was possible based on an expression of Ceacam1 was verified as in the case of Eva1. Specifically, whether or not there was a correlation between the expression of Ceacam1 at an mRNA level in gliomas derived from patients and the survival rate of the patients was examined using the brain tumor database REMBRANT of the National Cancer institute of the US. FIG. 27 shows the obtained result.

As apparent from the result shown in FIG. 27, the survival time of the patients with gliomas in which the Ceacam1 gene was expressed at high level was 500 days or shorter after the prognosis examination was started; meanwhile, a significant correlation was observed between the expression of the Ceacam1 and the prognosis of glioma patients. Thus, it was demonstrated that detecting Ceacam1 gene expression was effective in glioma testing, particularly a prognosis of glioma patients. Incidentally, although unillustrated, in a similar analysis, no significant correlation was observed between fgf5 expression and a prognosis of glioma patients.

Example 13

Figure 28:
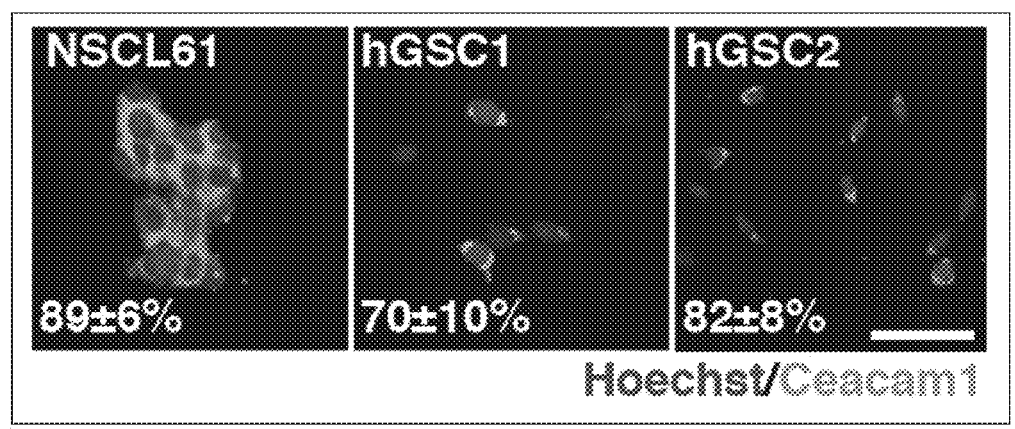
FIG. 28 shows micrographs for illustrating the immunostaining analysis result on an expression of Ceacam1 in NSCL61 and hGSCs. Note that a portion exhibiting green fluorescence in the figure indicates a site stained with an anti-Ceacam1 antibody, and a portion exhibiting blue fluorescence in the figure indicates a nucleus in the cell subjected to counter staining using Hoechst 33342. Moreover, in the figure, the scale bar represents 100 µm.
Figure 29:
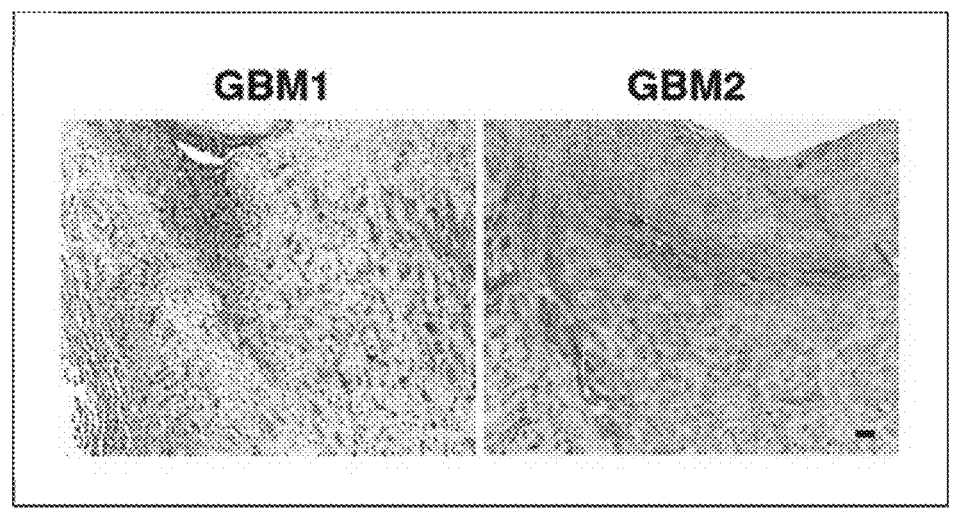
FIG. 29 shows micrographs for illustrating the immunostaining analysis result on an expression of Ceacam1 in primary GBM specimens (GBM1 and GBM2). Note that, in the figure, a brown portion indicates a site stained with the anti-Ceacam1 antibody. Moreover, in the figure, the scale bar represents 100 µm.
Figure 30:
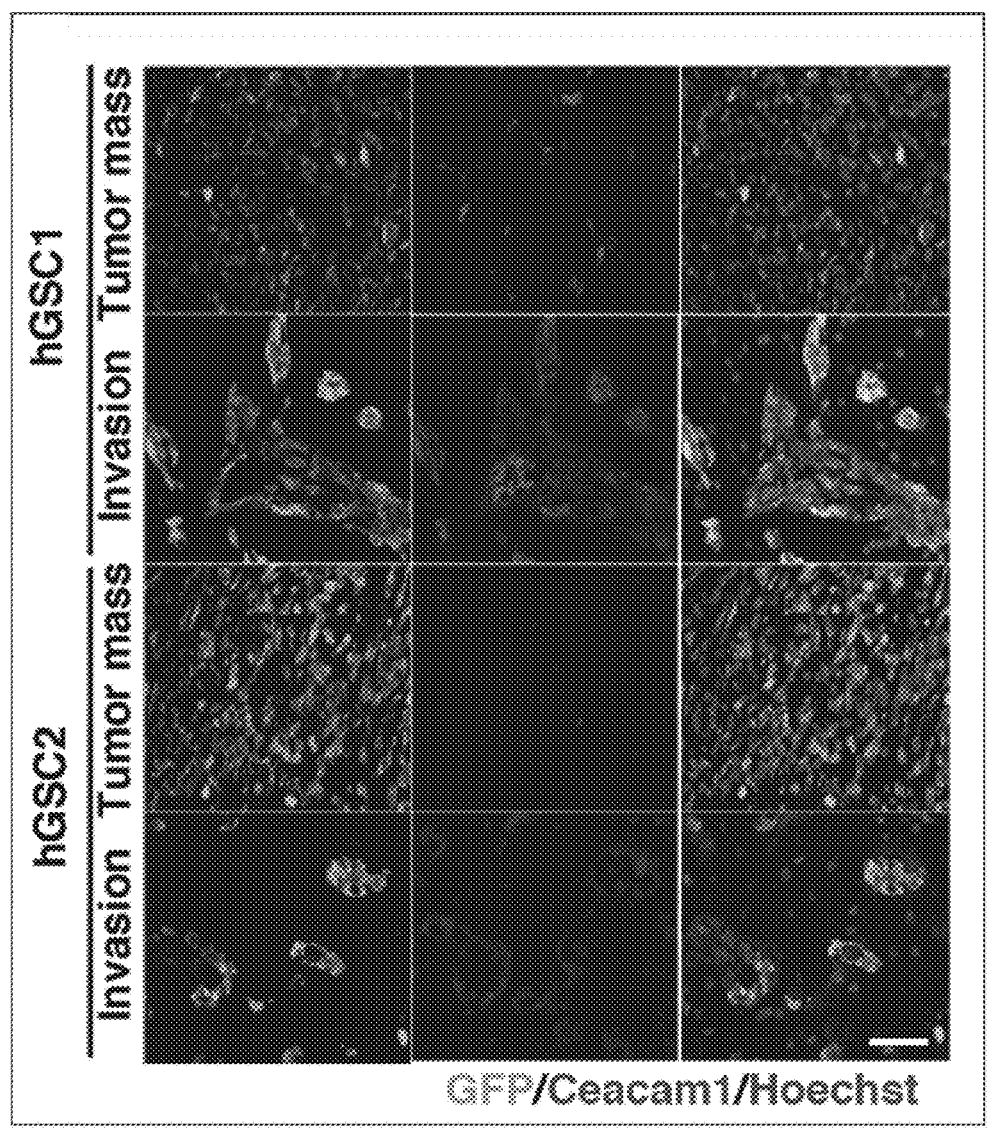
FIG. 30 shows micrographs for illustrating the immunostaining analysis result on an expression of Ceacam1 in xenograft tumors prepared from hGSCs. Note that a portion exhibiting red fluorescence in the figure indicates a site stained with the anti-Ceacam1 antibody (see four panels in the middle). A portion exhibiting green fluorescence in the figure indicates a GFP-expressing site (see top four panels), and a portion exhibiting blue fluorescence in the figure indicates a nucleus in the cell subjected to counter staining using Hoechst 33342. Moreover, in the figure, the scale bar represents 100 µm, and bottom four panels are photographs each obtained by superimposing a staining image with the anti-Ceacam1 antibody, a staining image with an anti-GFP antibody, and a staining image with Hoechst 33342. Further, in the figure, "Invasion" and "Tumor mass" respectively show an "invaded" portion and a "tumor mass" in the xenograft tumors.

The localization of Ceacam1 in cells was analyzed by immunostaining. FIG. 28 shows the obtained result. Moreover, the localization of Ceacam1 in tissues was analyzed by immunostaining. FIGS. 29 and 30 show the obtained result.

As apparent from the result shown in FIG. 28, it was observed that Ceacam1 was expressed on the cell surfaces of NSCL61 and hGSCs. Moreover, as shown in FIGS. 29 and 30, it was revealed that Ceacam1-positive cells were present in the human primary GMB tissues (GBM1 and GBM2). Further, as in the case of Eva1, it was revealed that Ceacam1 was mainly present more on invading hGSCs than on hGSCs in the tumor mass.

Example 14

It is known that splicing variants of Ceacam1 includes: Ceacam-S constituted of an N-terminus variable Ig-like domain, a conserved transmembrane region, and a short cytoplasmic domain; and Ceacam-L constituted of an N-terminus variable Ig-like domain, a conserved transmembrane region, and a long cytoplasmic domain.

In addition, there is also a report that Ceacam1-S and Ceacam6 expressed in a malignant tumor are capable of blocking an inhibitory signal of Ceacam1-L by inhibiting homodimer formation of Ceacam1-L to increase the antigenic activity thereof (Muller, M. M., et al., J. Cell Biol., 2009, vol. 187, pp. 569 to 581, Singer, B. B., et al., PLoS One, 2010, 5, e8747).

Figure 31:
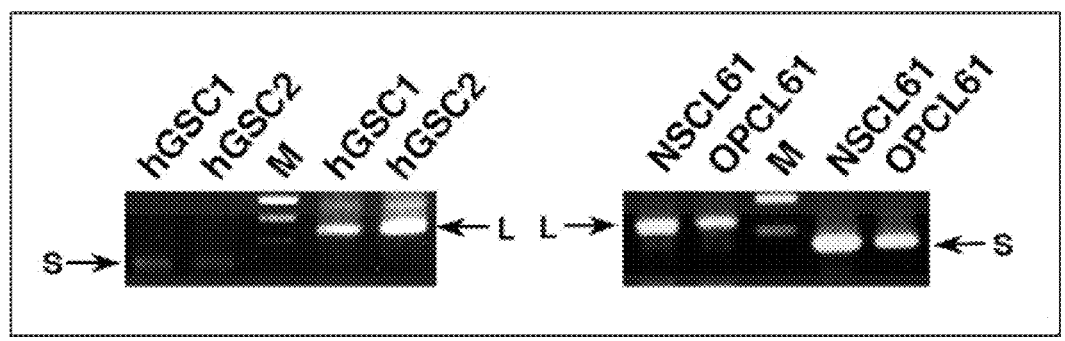
FIG. 31 shows photographs of electrophoreses for illustrating the RT-PCR analysis result on expressions of ceacam1-1 (L) and ceacam1-s (S) in hGSCs, NSCL61, and OPCL61. Note that, in the figure, "M" indicates a lane on which HyperLadder 1 (manufactured by Bioline Reagents Ltd.) was spread.
Figure 32:
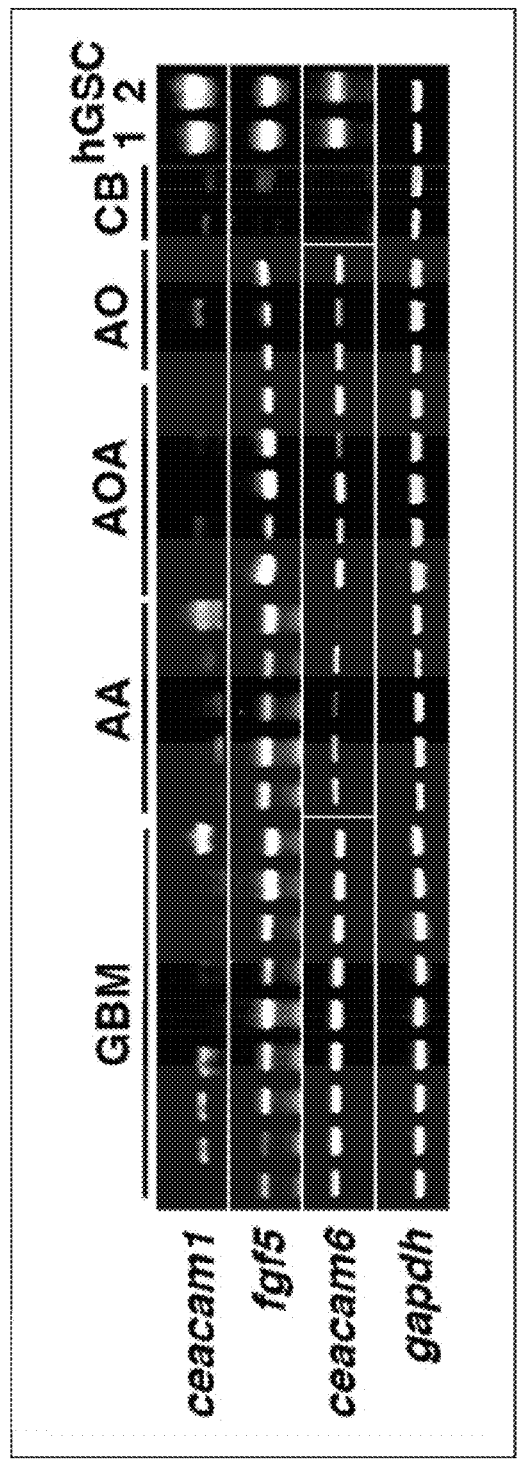
FIG. 32 shows photographs of electrophoreses for illustrating the RT-PCR analysis result on expressions of ceacam1, fgf5, and ceacam6 in human primary gliomas and hGSCs. Note that the expression of a gapdh gene was used as an internal standard.

For this reason, expressions of Ceacam1-L and Ceacam1-S in human and mouse glioma stem cells were analyzed by RT-PCR. FIG. 31 shows the obtained result. Moreover, expressions of Ceacam1 and Ceacam6 in malignant gliomas and human glioma stem cells were analyzed by RT-PCR. FIG. 32 shows the obtained result.

As apparent from the result shown in FIG. 31, mainly Ceacam1-L, but not Ceacam-S, was expressed in the human glioma stem cells. Meanwhile, both of the variants were expressed in the mouse glioma stem cells. Additionally, as apparent from the result shown in FIG. 32, Ceacam6 was expressed in hGSCs and all the human malignant gliomas.

Example 15

Figure 34:
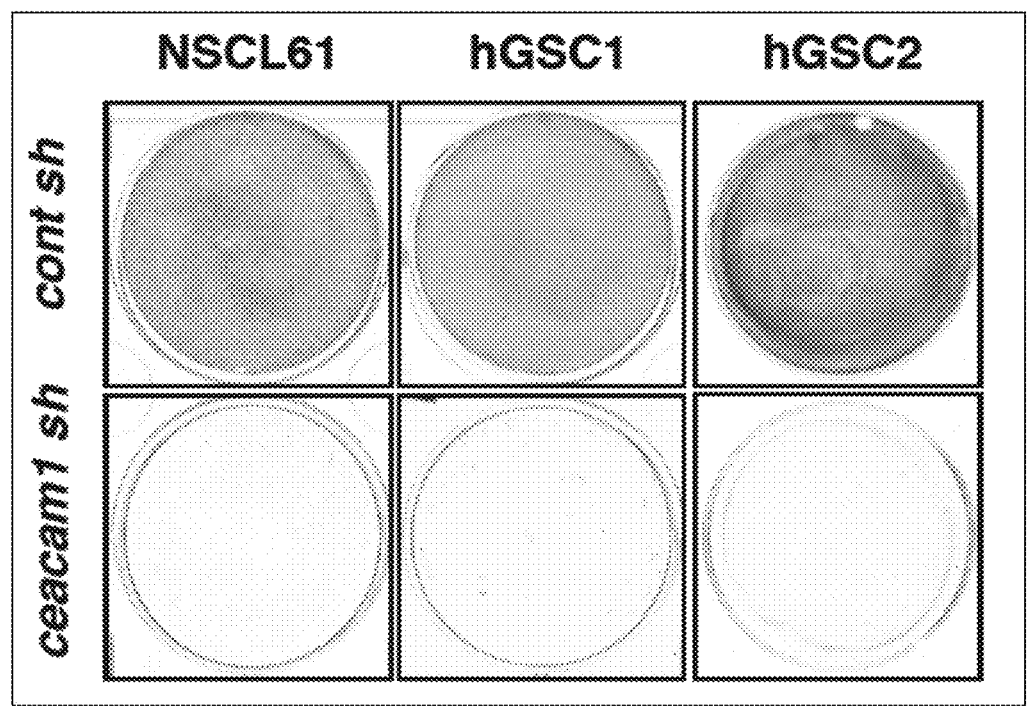
FIG. 34 shows photographs for illustrating the analysis result on proliferations of controlsh-expressing NSCL61, ceacam1sh-expressing NSCL61, controlsh-expressing hGSC61, and ceacam1sh-expressing hGSCs by crystal violet staining.
Figure 35:
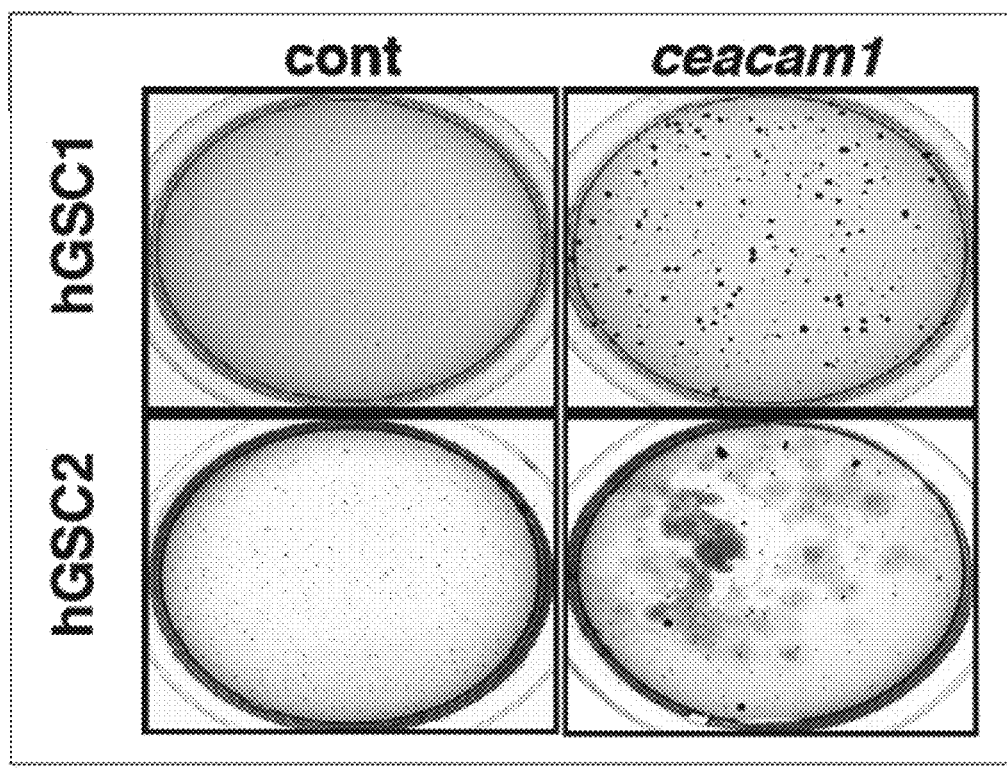
FIG. 35 shows photographs for illustrating that, on soft agar, the Ceacam1-expressing hGSCs formed larger colonies than those by parent cells of the hGSCs (cont).
Figure 36:
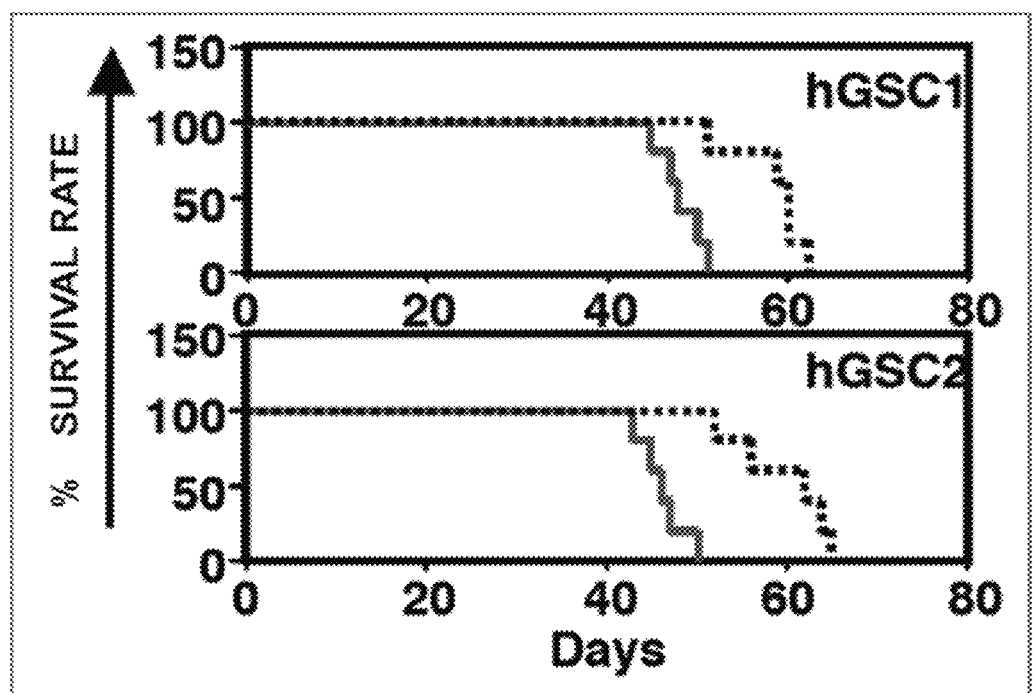
FIG. 36 shows graphs for illustrating a survival curve (solid line) of mice injected with the Ceacam1-expressing hGSCs and a survival curve (dotted line) of mice injected with the parent cells of the hGSCs.
Figure 37:
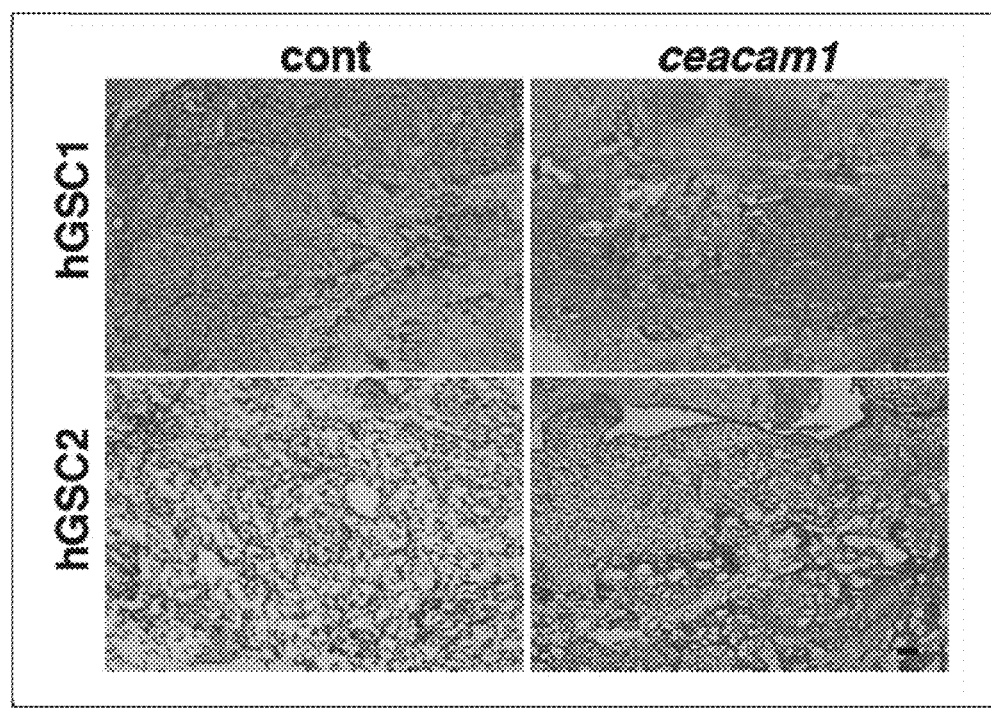
FIG. 37 shows micrographs for illustrating the analysis result on glioma specimens derived from the Ceacam1-expressing hGSCs by hematoxylin and eosin staining. In the figure, the scale bar represents 100 µm.

In order to examine the association between the expressions of Ceacam1-S, Ceacam1-L, and Ceacam6 in a glioma shown in Example 14 and the tumor malignancy or anti-tumor activity, ceacam1sh was overexpressed in glioma stem cells. FIG. 34 shows the obtained result. Moreover, Ceacam1-L was forcibly expressed in glioma stem cells. FIGS. 35 to 37 show the obtained result.

Figure 33:
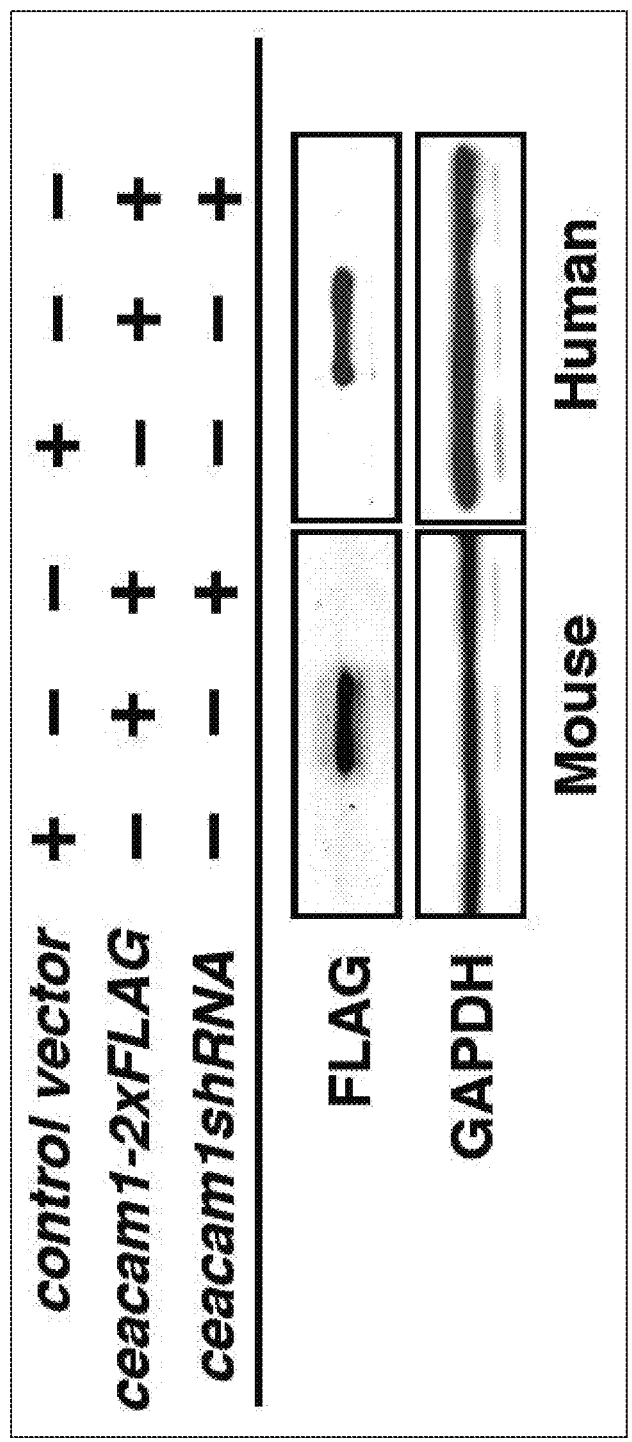
FIG. 33 shows photographs for illustrating the result of analyzing Cos7 cells, which were forced to express FLAG® (DYKDDDDK peptide)-attached Ceacam1-L and/or Ceacam1 shRNA, by western blotting using an anti-FLAG® antibody and an anti-GAPDH antibody. A control vector, a FLAG® (DYKDDDDK peptide)-attached Ceacam1-L expression vector (ceacam1-2×FLAG® (DYKDDDDK peptide), or a ceacam1sh expression vector (ceacam1 shRNA) was introduced into Cos7 cells, and cell extracts collected 2 days after the introduction (transfection) were used for the western blotting. Note that the analysis result using the anti-GAPDH antibody was used as an internal standard (loading control). Moreover, "Mouse" shows the result of mouse Ceacam1, and "Human" shows the result of human Ceacam1.

Note that, in this Example, the effectiveness of ceacam1sh (ceacam1 shRNA) used to suppress the expression of ceacam1 and Ceacam1-2×FLAG® (DYKDDDDK peptide) used to promote the expression of Ceacam1-L had been confirmed by western blotting for both mouse and human as shown in FIG. 33.

As apparent from the result shown in FIG. 34, the overexpression of ceacam1sh inhibited proliferations of NSCL61 and hGSCs. In contrast, as apparent from the result shown in FIGS. 35 to 37, it was observed that the forced expression of Ceacam1-L not only increased the colony formation by hGSCs on soft agar (see FIG. 35) but also promoted the malignancy of hGSCs in vivo (see FIGS. 36 and 37). Specifically, it was revealed that the average survival time of the mice into which Ceacam1-L-overexpressing hGSCs were transplanted (48 dp=0.0044 and 46d, p=0.0039) was shortened in comparison with that of the mice into which control hGSCs were transplanted (60d and 62d) (see FIG. 36). Thus, these results revealed that Ceacam1 was involved in the malignancy of glioma stem cells, and demonstrated that Ceacam1 was also an effective target for glioma treatment and testing as in the case of Eva1.

INDUSTRIAL APPLICABILITY

As has been described above, targeting Eva1 and/or Ceacam1 enables glioma testing and treatment, and delivering of a desired substance to a glioma. Thus, the present invention can greatly contribute to the medical field particularly of gliomas.

SEQUENCE LISTING FREE TEXT

SEQ ID NO: 1
<223> human Eva1
SEQ ID NO: 3
<223> mouse Eva1
SEQ ID NOs: 5 to 8
<223> Artificially synthesized primer sequence
SEQ ID NOs: 9 to 11
<223> shRNA target sequence
SEQ ID NO: 13
<223> human Ceacam1-4L
SEQ ID NO: 15
<223> human Ceacam1-4S
SEQ ID NO: 17
<223> mouse Ceacam1-2L
SEQ ID NO: 19
<223> mouse Ceacam1-2S
SEQ ID NO: 21
<223> human Ceacam6
SEQ ID NOs: 23 to 74
<223> Artificially synthesized primer sequence
SEQ ID NOs: 75 and 76
<223> shRNA target sequence

The invention claimed is:

1. A method of treating glioma comprising:
   (a) administering to a subject in need thereof an anti-Eva1 protein antibody intracranially or via intratumoral administration, to suppress Eva1 protein function; or
   (b) administering to a subject in need thereof an anti-Eva1 protein antibody bound to a blood brain-barrier permeable substance, to suppress Eva1 protein function.

* * * * *

SEQUENCE LISTING

<160> NUMBER OF SEQ ID NOS: 77

<210> SEQ ID NO 1
<211> LENGTH: 648
<212> TYPE: DNA
<213> ORGANISM: Homo sapiens
<220> FEATURE:
<221> NAME/KEY: CDS
<222> LOCATION: (1)..(648)

<400> SEQUENCE: 1

```
atg tat ggc aag agc tct act cgt gcg gtg ctt ctt ctc ctt ggc ata      48
Met Tyr Gly Lys Ser Ser Thr Arg Ala Val Leu Leu Leu Leu Gly Ile
1               5                   10                  15 cag ctc aca gct ctt tgg cct ata gca gct gtg gaa att tat acc tcc      96
Gln Leu Thr Ala Leu Trp Pro Ile Ala Ala Val Glu Ile Tyr Thr Ser
            20                  25                  30 cgg gtg ctg gag gct gtt aat ggg aca gat gct cgg tta aaa tgc act     144
Arg Val Leu Glu Ala Val Asn Gly Thr Asp Ala Arg Leu Lys Cys Thr
        35                  40                  45 ttc tcc agc ttt gcc cct gtg ggt gat gct cta aca gtg acc tgg aat     192
```

```
Phe Ser Ser Phe Ala Pro Val Gly Asp Ala Leu Thr Val Thr Trp Asn
     50                  55                  60 ttt cgt cct cta gac ggg gga cct gag cag ttt gta ttc tac tac cac     240
Phe Arg Pro Leu Asp Gly Gly Pro Glu Gln Phe Val Phe Tyr Tyr His
 65                  70                  75                  80 ata gat ccc ttc caa ccc atg agt ggg cgg ttt aag gac cgg gtg tct     288
Ile Asp Pro Phe Gln Pro Met Ser Gly Arg Phe Lys Asp Arg Val Ser
                 85                  90                  95 tgg gat ggg aat cct gag cgg tac gat gcc tcc atc ctt ctc tgg aaa     336
Trp Asp Gly Asn Pro Glu Arg Tyr Asp Ala Ser Ile Leu Leu Trp Lys
            100                 105                 110 ctg cag ttc gac gac aat ggg aca tac acc tgc cag gtg aag aac cca     384
Leu Gln Phe Asp Asp Asn Gly Thr Tyr Thr Cys Gln Val Lys Asn Pro
        115                 120                 125 cct gat gtt gat ggg gtg ata ggg gag atc cgg ctc agc gtc gtg cac     432
Pro Asp Val Asp Gly Val Ile Gly Glu Ile Arg Leu Ser Val Val His
    130                 135                 140 act gta cgc ttc tct gag atc cac ttc ctg gct ctg gcc att ggc tct     480
Thr Val Arg Phe Ser Glu Ile His Phe Leu Ala Leu Ala Ile Gly Ser
145                 150                 155                 160 gcc tgt gca ctg atg atc ata gta att gta gtg gtc ctc ttc cag         528
Ala Cys Ala Leu Met Ile Ile Ile Val Ile Val Val Leu Phe Gln
                165                 170                 175 cat tac cgg aaa aag cga tgg gcc gaa aga gct cat aaa gtg gtg gag     576
His Tyr Arg Lys Lys Arg Trp Ala Glu Arg Ala His Lys Val Val Glu
            180                 185                 190 ata aaa tca aaa gaa gag gaa agg ctc aac caa gag aaa aag gtc tct     624
Ile Lys Ser Lys Glu Glu Glu Arg Leu Asn Gln Glu Lys Lys Val Ser
        195                 200                 205 gtt tat tta gaa gac aca gac taa                                     648
Val Tyr Leu Glu Asp Thr Asp
    210                 215

<210> SEQ ID NO 2
<211> LENGTH: 215
<212> TYPE: PRT
<213> ORGANISM: Homo sapiens

<400> SEQUENCE: 2

Met Tyr Gly Lys Ser Ser Thr Arg Ala Val Leu Leu Leu Leu Gly Ile
1               5                   10                  15

Gln Leu Thr Ala Leu Trp Pro Ile Ala Ala Val Glu Ile Tyr Thr Ser
            20                  25                  30

Arg Val Leu Glu Ala Val Asn Gly Thr Asp Ala Arg Leu Lys Cys Thr
        35                  40                  45

Phe Ser Ser Phe Ala Pro Val Gly Asp Ala Leu Thr Val Thr Trp Asn
    50                  55                  60

Phe Arg Pro Leu Asp Gly Gly Pro Glu Gln Phe Val Phe Tyr Tyr His
65                  70                  75                  80

Ile Asp Pro Phe Gln Pro Met Ser Gly Arg Phe Lys Asp Arg Val Ser
                85                  90                  95

Trp Asp Gly Asn Pro Glu Arg Tyr Asp Ala Ser Ile Leu Leu Trp Lys
            100                 105                 110

Leu Gln Phe Asp Asp Asn Gly Thr Tyr Thr Cys Gln Val Lys Asn Pro
        115                 120                 125

Pro Asp Val Asp Gly Val Ile Gly Glu Ile Arg Leu Ser Val Val His
    130                 135                 140

Thr Val Arg Phe Ser Glu Ile His Phe Leu Ala Leu Ala Ile Gly Ser
```

```
                145                 150                 155                 160
Ala Cys Ala Leu Met Ile Ile Val Val Ile Val Val Leu Phe Gln
                    165                 170                 175

His Tyr Arg Lys Lys Arg Trp Ala Glu Arg Ala His Lys Val Val Glu
                    180                 185                 190

Ile Lys Ser Lys Glu Glu Glu Arg Leu Asn Gln Glu Lys Lys Val Ser
                195                 200                 205

Val Tyr Leu Glu Asp Thr Asp
                210                 215

<210> SEQ ID NO 3
<211> LENGTH: 648
<212> TYPE: DNA
<213> ORGANISM: Mus musculus
<220> FEATURE:
<221> NAME/KEY: CDS
<222> LOCATION: (1)..(648)

<400> SEQUENCE: 3 atg tat ggc aag agc ccc gcg ctt gtg ctt cca ctt ctc ctg agt tta          48
Met Tyr Gly Lys Ser Pro Ala Leu Val Leu Pro Leu Leu Leu Ser Leu
1               5                   10                  15 cag ctc aca gcc ctt tgt cct aca gaa gct gtg gaa att tac acc tcc          96
Gln Leu Thr Ala Leu Cys Pro Thr Glu Ala Val Glu Ile Tyr Thr Ser
                20                  25                  30 ggg gcc ctg gag gca gtc aac ggg aca gat gtt cgg tta aaa tgc act         144
Gly Ala Leu Glu Ala Val Asn Gly Thr Asp Val Arg Leu Lys Cys Thr
            35                  40                  45 ttc tcc agc ttt gcc cct gtg gga gat gcg cta act gtg acg tgg aat         192
Phe Ser Ser Phe Ala Pro Val Gly Asp Ala Leu Thr Val Thr Trp Asn
50                  55                  60 ttc cga cct cga gat ggg ggt cgt gag cag ttt gta ttc tac tac cac         240
Phe Arg Pro Arg Asp Gly Gly Arg Glu Gln Phe Val Phe Tyr Tyr His
65                  70                  75                  80 atg gac ccc ttc agg ccc atg agc gga cgg ttc aaa gac cgg gtg gtc         288
Met Asp Pro Phe Arg Pro Met Ser Gly Arg Phe Lys Asp Arg Val Val
                85                  90                  95 tgg gac gga aac ccc gag cga tat gac gtc tcc atc ttg ctc tgg aag         336
Trp Asp Gly Asn Pro Glu Arg Tyr Asp Val Ser Ile Leu Leu Trp Lys
            100                 105                 110 ctg cag ttt gac gac aat ggg aca tac acc tgc cag gtg aag aat cca         384
Leu Gln Phe Asp Asp Asn Gly Thr Tyr Thr Cys Gln Val Lys Asn Pro
        115                 120                 125 cct gat gtt gat ggt ctg gtt ggg acg atc cgg ctc agc gtt gtg cac         432
Pro Asp Val Asp Gly Leu Val Gly Thr Ile Arg Leu Ser Val Val His
    130                 135                 140 act gtg ccc ttc tct gag atc tac ttc ctg gcc gtg gcc att ggc tct         480
Thr Val Pro Phe Ser Glu Ile Tyr Phe Leu Ala Val Ala Ile Gly Ser
145                 150                 155                 160 gcg tgc gca ctg atg atc atc gta gtg atc gtg gta gtc ctc ttc cag         528
Ala Cys Ala Leu Met Ile Ile Val Val Ile Val Val Val Leu Phe Gln
                165                 170                 175 cac ttc cgg aaa aag cga tgg gcg gac agt gct gat aaa gcc gag ggg         576
His Phe Arg Lys Lys Arg Trp Ala Asp Ser Ala Asp Lys Ala Glu Gly
            180                 185                 190 aca aaa tca aaa gaa gag gaa aaa ctc aac caa gga aac aag gtc tct         624
Thr Lys Ser Lys Glu Glu Glu Lys Leu Asn Gln Gly Asn Lys Val Ser
        195                 200                 205 gtt ttt gtg gaa gat aca gac taa                                         648
Val Phe Val Glu Asp Thr Asp
```

<210> SEQ ID NO 4
<211> LENGTH: 215
<212> TYPE: PRT
<213> ORGANISM: Mus musculus

<400> SEQUENCE: 4

Met Tyr Gly Lys Ser Pro Ala Leu Val Leu Pro Leu Leu Ser Leu
1               5                   10                  15

Gln Leu Thr Ala Leu Cys Pro Thr Glu Ala Val Glu Ile Tyr Thr Ser
            20                  25                  30

Gly Ala Leu Glu Ala Val Asn Gly Thr Asp Val Arg Leu Lys Cys Thr
        35                  40                  45

Phe Ser Ser Phe Ala Pro Val Gly Asp Ala Leu Thr Val Thr Trp Asn
    50                  55                  60

Phe Arg Pro Arg Asp Gly Gly Arg Glu Gln Phe Val Phe Tyr Tyr His
65                  70                  75                  80

Met Asp Pro Phe Arg Pro Met Ser Gly Arg Phe Lys Asp Arg Val Val
                85                  90                  95

Trp Asp Gly Asn Pro Glu Arg Tyr Asp Val Ser Ile Leu Leu Trp Lys
            100                 105                 110

Leu Gln Phe Asp Asp Asn Gly Thr Tyr Thr Cys Gln Val Lys Asn Pro
        115                 120                 125

Pro Asp Val Asp Gly Leu Val Gly Thr Ile Arg Leu Ser Val Val His
    130                 135                 140

Thr Val Pro Phe Ser Glu Ile Tyr Phe Leu Ala Val Ala Ile Gly Ser
145                 150                 155                 160

Ala Cys Ala Leu Met Ile Ile Val Val Ile Val Val Leu Phe Gln
                165                 170                 175

His Phe Arg Lys Lys Arg Trp Ala Asp Ser Ala Asp Lys Ala Glu Gly
            180                 185                 190

Thr Lys Ser Lys Glu Glu Lys Leu Asn Gln Gly Asn Lys Val Ser
        195                 200                 205

Val Phe Val Glu Asp Thr Asp
    210                 215

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 5
ttctccagct ttgcccctgt                                           20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
ccgcccatcg cttttccgg                                            20

<210> SEQ ID NO 7
<211> LENGTH: 33

-continued

<210> SEQ ID NO 7
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 7
agaattcgcc accatgtatg gcaagagccc cgc                                    33

<210> SEQ ID NO 8
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 8
actcgaggtc tgtatcttcc acaaaaaca                                         29

<210> SEQ ID NO 9
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 9
gcagtcaacg ggacagatgt t                                                 21

<210> SEQ ID NO 10
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 10
gtgcacactg tacgcttctc t                                                 21

<210> SEQ ID NO 11
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 11
gcaagctgac cctgaagttc a                                                 21

<210> SEQ ID NO 12
<211> LENGTH: 17
<212> TYPE: PRT
<213> ORGANISM: Homo sapiens

<400> SEQUENCE: 12

Pro Met Ser Gly Arg Phe Lys Asp Arg Val Ser Trp Asp Gly Asn Pro
1               5                   10                  15

Glu

<210> SEQ ID NO 13
<211> LENGTH: 1581
<212> TYPE: DNA
<213> ORGANISM: Homo sapiens
<220> FEATURE:
<221> NAME/KEY: CDS
<222> LOCATION: (1)..(1581)

<400> SEQUENCE: 13

| | | | | | | | | | | | | | | | | |
|---|---|---|---|---|---|---|---|---|---|---|---|---|---|---|---|---|
| atg | ggg | cac | ctc | tca | gcc | cca | ctt | cac | aga | gtg | cgt | gta | ccc | tgg | cag | 48 |
| Met | Gly | His | Leu | Ser | Ala | Pro | Leu | His | Arg | Val | Arg | Val | Pro | Trp | Gln | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggg | ctt | ctg | ctc | aca | gcc | tca | ctt | cta | acc | ttc | tgg | aac | ccg | ccc | acc | 96 |
| Gly | Leu | Leu | Leu | Thr | Ala | Ser | Leu | Leu | Thr | Phe | Trp | Asn | Pro | Pro | Thr | |
| | | | 20 | | | | | 25 | | | | | 30 | | | |

| | | | | | | | | | | | | | | | | |
|---|---|---|---|---|---|---|---|---|---|---|---|---|---|---|---|---|
| act | gcc | cag | ctc | act | act | gaa | tcc | atg | cca | ttc | aat | gtt | gca | gag | ggg | 144 |
| Thr | Ala | Gln | Leu | Thr | Thr | Glu | Ser | Met | Pro | Phe | Asn | Val | Ala | Glu | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| aag | gag | gtt | ctt | ctc | ctt | gtc | cac | aat | ctg | ccc | cag | caa | ctt | ttt | ggc | 192 |
| Lys | Glu | Val | Leu | Leu | Leu | Val | His | Asn | Leu | Pro | Gln | Gln | Leu | Phe | Gly | |
| | 50 | | | | | 55 | | | | | 60 | | | | | |

| | | | | | | | | | | | | | | | | |
|---|---|---|---|---|---|---|---|---|---|---|---|---|---|---|---|---|
| tac | agc | tgg | tac | aaa | ggg | gaa | aga | gtg | gat | ggc | aac | cgt | caa | att | gta | 240 |
| Tyr | Ser | Trp | Tyr | Lys | Gly | Glu | Arg | Val | Asp | Gly | Asn | Arg | Gln | Ile | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gga | tat | gca | ata | gga | act | caa | caa | gct | acc | cca | ggg | ccc | gca | aac | agc | 288 |
| Gly | Tyr | Ala | Ile | Gly | Thr | Gln | Gln | Ala | Thr | Pro | Gly | Pro | Ala | Asn | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | cga | gag | aca | ata | tac | ccc | aat | gca | tcc | ctg | ctg | atc | cag | aac | gtc | 336 |
| Gly | Arg | Glu | Thr | Ile | Tyr | Pro | Asn | Ala | Ser | Leu | Leu | Ile | Gln | Asn | Val | |
| | | | 100 | | | | | 105 | | | | | 110 | | | |

| | | | | | | | | | | | | | | | | |
|---|---|---|---|---|---|---|---|---|---|---|---|---|---|---|---|---|
| acc | cag | aat | gac | aca | gga | ttc | tac | acc | cta | caa | gtc | ata | aag | tca | gat | 384 |
| Thr | Gln | Asn | Asp | Thr | Gly | Phe | Tyr | Thr | Leu | Gln | Val | Ile | Lys | Ser | Asp | |
| | | 115 | | | | | 120 | | | | | 125 | | | | |

| | | | | | | | | | | | | | | | | |
|---|---|---|---|---|---|---|---|---|---|---|---|---|---|---|---|---|
| ctt | gtg | aat | gaa | gaa | gca | act | gga | cag | ttc | cat | gta | tac | ccg | gag | ctg | 432 |
| Leu | Val | Asn | Glu | Glu | Ala | Thr | Gly | Gln | Phe | His | Val | Tyr | Pro | Glu | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| ccc | aag | ccc | tcc | atc | tcc | agc | aac | aac | tcc | aac | cct | gtg | gag | gac | aag | 480 |
| Pro | Lys | Pro | Ser | Ile | Ser | Ser | Asn | Asn | Ser | Asn | Pro | Val | Glu | Asp | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gat | gct | gtg | gcc | ttc | acc | tgt | gaa | cct | gag | act | cag | gac | aca | acc | tac | 528 |
| Asp | Ala | Val | Ala | Phe | Thr | Cys | Glu | Pro | Glu | Thr | Gln | Asp | Thr | Thr | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| ctg | tgg | tgg | ata | aac | aat | cag | agc | ctc | ccg | gtc | agt | ccc | agg | ctg | cag | 576 |
| Leu | Trp | Trp | Ile | Asn | Asn | Gln | Ser | Leu | Pro | Val | Ser | Pro | Arg | Leu | Gln | |
| | | | 180 | | | | | 185 | | | | | 190 | | | |

| | | | | | | | | | | | | | | | | |
|---|---|---|---|---|---|---|---|---|---|---|---|---|---|---|---|---|
| ctg | tcc | aat | ggc | aac | agg | acc | ctc | act | cta | ctc | agt | gtc | aca | agg | aat | 624 |
| Leu | Ser | Asn | Gly | Asn | Arg | Thr | Leu | Thr | Leu | Leu | Ser | Val | Thr | Arg | Asn | |
| | | 195 | | | | | 200 | | | | | 205 | | | | |

| | | | | | | | | | | | | | | | | |
|---|---|---|---|---|---|---|---|---|---|---|---|---|---|---|---|---|
| gac | aca | gga | ccc | tat | gag | tgt | gaa | ata | cag | aac | cca | gtg | agt | gcg | aac | 672 |
| Asp | Thr | Gly | Pro | Tyr | Glu | Cys | Glu | Ile | Gln | Asn | Pro | Val | Ser | Ala | Asn | |
| | 210 | | | | | 215 | | | | | 220 | | | | | |

| | | | | | | | | | | | | | | | | |
|---|---|---|---|---|---|---|---|---|---|---|---|---|---|---|---|---|
| cgc | agt | gac | cca | gtc | acc | ttg | aat | gtc | acc | tat | ggc | ccg | gac | acc | ccc | 720 |
| Arg | Ser | Asp | Pro | Val | Thr | Leu | Asn | Val | Thr | Tyr | Gly | Pro | Asp | Thr | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| acc | att | tcc | cct | tca | gac | acc | tat | tac | cgt | cca | ggg | gca | aac | ctc | agc | 768 |
| Thr | Ile | Ser | Pro | Ser | Asp | Thr | Tyr | Tyr | Arg | Pro | Gly | Ala | Asn | Leu | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| ctc | tcc | tgc | tat | gca | gcc | tct | aac | cca | cct | gca | cag | tac | tcc | tgg | ctt | 816 |
| Leu | Ser | Cys | Tyr | Ala | Ala | Ser | Asn | Pro | Pro | Ala | Gln | Tyr | Ser | Trp | Leu | |
| | | | 260 | | | | | 265 | | | | | 270 | | | |

| | | | | | | | | | | | | | | | | |
|---|---|---|---|---|---|---|---|---|---|---|---|---|---|---|---|---|
| atc | aat | gga | aca | ttc | cag | caa | agc | aca | caa | gag | ctc | ttt | atc | cct | aac | 864 |
| Ile | Asn | Gly | Thr | Phe | Gln | Gln | Ser | Thr | Gln | Glu | Leu | Phe | Ile | Pro | Asn | |
| | | 275 | | | | | 280 | | | | | 285 | | | | |

| | | | | | | | | | | | | | | | | |
|---|---|---|---|---|---|---|---|---|---|---|---|---|---|---|---|---|
| atc | act | gtg | aat | aat | agt | gga | tcc | tat | acc | tgc | cac | gcc | aat | aac | tca | 912 |
| Ile | Thr | Val | Asn | Asn | Ser | Gly | Ser | Tyr | Thr | Cys | His | Ala | Asn | Asn | Ser | |
| | 290 | | | | | 295 | | | | | 300 | | | | | |

| | | | | | | | | | | | | | | | | |
|---|---|---|---|---|---|---|---|---|---|---|---|---|---|---|---|---|
| gtc | act | ggc | tgc | aac | agg | acc | aca | gtc | aag | acg | atc | ata | gtc | act | gag | 960 |

| | | | | | | | | | | | | | | |
|---|---|---|---|---|---|---|---|---|---|---|---|---|---|---|
| Val | Thr | Gly | Cys | Asn | Arg | Thr | Thr | Val | Lys | Thr | Ile | Ile | Val | Thr | Glu |
| 305 | | | | | 310 | | | | | 315 | | | | | 320 |

```
cta agt cca gta gta gca aag ccc caa atc aaa gcc agc aag acc aca        1008
Leu Ser Pro Val Val Ala Lys Pro Gln Ile Lys Ala Ser Lys Thr Thr
                    325                 330                 335 gtc aca gga gat aag gac tct gtg aac ctg acc tgc tcc aca aat gac        1056
Val Thr Gly Asp Lys Asp Ser Val Asn Leu Thr Cys Ser Thr Asn Asp
                340                 345                 350 act gga atc tcc atc cgt tgg ttc ttc aaa aac cag agt ctc ccg tcc        1104
Thr Gly Ile Ser Ile Arg Trp Phe Phe Lys Asn Gln Ser Leu Pro Ser
            355                 360                 365 tcg gag agg atg aag ctg tcc cag ggc aac acc acc ctc agc ata aac        1152
Ser Glu Arg Met Lys Leu Ser Gln Gly Asn Thr Thr Leu Ser Ile Asn
        370                 375                 380 cct gtc aag agg gag gat gct ggg acg tat tgg tgt gag gtc ttc aac        1200
Pro Val Lys Arg Glu Asp Ala Gly Thr Tyr Trp Cys Glu Val Phe Asn
385                 390                 395                 400 cca atc agt aag aac caa agc gac ccc atc atg ctg aac gta aac tat        1248
Pro Ile Ser Lys Asn Gln Ser Asp Pro Ile Met Leu Asn Val Asn Tyr
                405                 410                 415 aat gct cta cca caa gaa aat ggc ctc tca cct ggg gcc att gct ggc        1296
Asn Ala Leu Pro Gln Glu Asn Gly Leu Ser Pro Gly Ala Ile Ala Gly
                420                 425                 430 att gtg att gga gta gtg gcc ctg gtt gct ctg ata gca gta gcc ctg        1344
Ile Val Ile Gly Val Val Ala Leu Val Ala Leu Ile Ala Val Ala Leu
            435                 440                 445 gca tgt ttt ctg cat ttc ggg aag acc ggc agg gca agc gac cag cgt        1392
Ala Cys Phe Leu His Phe Gly Lys Thr Gly Arg Ala Ser Asp Gln Arg
        450                 455                 460 gat ctc aca gag cac aaa ccc tca gtc tcc aac cac act cag gac cac        1440
Asp Leu Thr Glu His Lys Pro Ser Val Ser Asn His Thr Gln Asp His
465                 470                 475                 480 tcc aat gac cca cct aac aag atg aat gaa gtt act tat tct acc ctg        1488
Ser Asn Asp Pro Pro Asn Lys Met Asn Glu Val Thr Tyr Ser Thr Leu
                485                 490                 495 aac ttt gaa gcc cag caa ccc aca caa cca act tca gcc tcc cca tcc        1536
Asn Phe Glu Ala Gln Gln Pro Thr Gln Pro Thr Ser Ala Ser Pro Ser
                500                 505                 510 cta aca gcc aca gaa ata att tat tca gaa gta aaa aag cag taa            1581
Leu Thr Ala Thr Glu Ile Ile Tyr Ser Glu Val Lys Lys Gln
            515                 520                 525

<210> SEQ ID NO 14
<211> LENGTH: 526
<212> TYPE: PRT
<213> ORGANISM: Homo sapiens

<400> SEQUENCE: 14

Met Gly His Leu Ser Ala Pro Leu His Arg Val Arg Val Pro Trp Gln
1               5                   10                  15

Gly Leu Leu Leu Thr Ala Ser Leu Leu Thr Phe Trp Asn Pro Pro Thr
            20                  25                  30

Thr Ala Gln Leu Thr Thr Glu Ser Met Pro Phe Asn Val Ala Glu Gly
        35                  40                  45

Lys Glu Val Leu Leu Leu Val His Asn Leu Pro Gln Gln Leu Phe Gly
    50                  55                  60

Tyr Ser Trp Tyr Lys Gly Glu Arg Val Asp Gly Asn Arg Gln Ile Val
65                  70                  75                  80

Gly Tyr Ala Ile Gly Thr Gln Gln Ala Thr Pro Gly Pro Ala Asn Ser
```

```
                        85                  90                  95
Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
            115                 120                 125

Leu Val Asn Glu Glu Ala Thr Gly Gln Phe His Val Tyr Pro Glu Leu
130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
            195                 200                 205

Asp Thr Gly Pro Tyr Glu Cys Glu Ile Gln Asn Pro Val Ser Ala Asn
210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
            275                 280                 285

Ile Thr Val Asn Asn Ser Gly Ser Tyr Thr Cys His Ala Asn Asn Ser
290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
            355                 360                 365

Ser Glu Arg Met Lys Leu Ser Gln Gly Asn Thr Thr Leu Ser Ile Asn
370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
            435                 440                 445

Ala Cys Phe Leu His Phe Gly Lys Thr Gly Arg Ala Ser Asp Gln Arg
450                 455                 460

Asp Leu Thr Glu His Lys Pro Ser Val Ser Asn His Thr Gln Asp His
465                 470                 475                 480

Ser Asn Asp Pro Pro Asn Lys Met Asn Glu Val Thr Tyr Ser Thr Leu
                485                 490                 495

Asn Phe Glu Ala Gln Gln Pro Thr Gln Pro Thr Ser Ala Ser Pro Ser
            500                 505                 510
```

<210> SEQ ID NO 15
<211> LENGTH: 1395
<212> TYPE: DNA
<213> ORGANISM: Homo sapiens
<220> FEATURE:
<221> NAME/KEY: CDS
<222> LOCATION: (1)..(1395)

<400> SEQUENCE: 15

| | | | | | | | | | | | | | | | | |
|---|---|---|---|---|---|---|---|---|---|---|---|---|---|---|---|---|
| atg | ggg | cac | ctc | tca | gcc | cca | ctt | cac | aga | gtg | cgt | gta | ccc | tgg | cag | 48 |
| Met | Gly | His | Leu | Ser | Ala | Pro | Leu | His | Arg | Val | Arg | Val | Pro | Trp | Gln | |
| 1 | | | | 5 | | | | | 10 | | | | | 15 | | |
| ggg | ctt | ctg | ctc | aca | gcc | tca | ctt | cta | acc | ttc | tgg | aac | ccg | ccc | acc | 96 |
| Gly | Leu | Leu | Leu | Thr | Ala | Ser | Leu | Leu | Thr | Phe | Trp | Asn | Pro | Pro | Thr | |
| | | | 20 | | | | | 25 | | | | | 30 | | | |
| act | gcc | cag | ctc | act | act | gaa | tcc | atg | cca | ttc | aat | gtt | gca | gag | ggg | 144 |
| Thr | Ala | Gln | Leu | Thr | Thr | Glu | Ser | Met | Pro | Phe | Asn | Val | Ala | Glu | Gly | |
| | | 35 | | | | | 40 | | | | | 45 | | | | |
| aag | gag | gtt | ctt | ctc | ctt | gtc | cac | aat | ctg | ccc | cag | caa | ctt | ttt | ggc | 192 |
| Lys | Glu | Val | Leu | Leu | Leu | Val | His | Asn | Leu | Pro | Gln | Gln | Leu | Phe | Gly | |
| | 50 | | | | | 55 | | | | | 60 | | | | | |
| tac | agc | tgg | tac | aaa | ggg | gaa | aga | gtg | gat | ggc | aac | cgt | caa | att | gta | 240 |
| Tyr | Ser | Trp | Tyr | Lys | Gly | Glu | Arg | Val | Asp | Gly | Asn | Arg | Gln | Ile | Val | |
| 65 | | | | | 70 | | | | | 75 | | | | | 80 | |
| gga | tat | gca | ata | gga | act | caa | caa | gct | acc | cca | ggg | ccc | gca | aac | agc | 288 |
| Gly | Tyr | Ala | Ile | Gly | Thr | Gln | Gln | Ala | Thr | Pro | Gly | Pro | Ala | Asn | Ser | |
| | | | | 85 | | | | | 90 | | | | | 95 | | |
| ggt | cga | gag | aca | ata | tac | ccc | aat | gca | tcc | ctg | ctg | atc | cag | aac | gtc | 336 |
| Gly | Arg | Glu | Thr | Ile | Tyr | Pro | Asn | Ala | Ser | Leu | Leu | Ile | Gln | Asn | Val | |
| | | | 100 | | | | | 105 | | | | | 110 | | | |
| acc | cag | aat | gac | aca | gga | ttc | tac | acc | cta | caa | gtc | ata | aag | tca | gat | 384 |
| Thr | Gln | Asn | Asp | Thr | Gly | Phe | Tyr | Thr | Leu | Gln | Val | Ile | Lys | Ser | Asp | |
| | | 115 | | | | | 120 | | | | | 125 | | | | |
| ctt | gtg | aat | gaa | gaa | gca | act | gga | cag | ttc | cat | gta | tac | ccg | gag | ctg | 432 |
| Leu | Val | Asn | Glu | Glu | Ala | Thr | Gly | Gln | Phe | His | Val | Tyr | Pro | Glu | Leu | |
| | 130 | | | | | 135 | | | | | 140 | | | | | |
| ccc | aag | ccc | tcc | atc | tcc | agc | aac | aac | tcc | aac | cct | gtg | gag | gac | aag | 480 |
| Pro | Lys | Pro | Ser | Ile | Ser | Ser | Asn | Asn | Ser | Asn | Pro | Val | Glu | Asp | Lys | |
| 145 | | | | | 150 | | | | | 155 | | | | | 160 | |
| gat | gct | gtg | gcc | ttc | acc | tgt | gaa | cct | gag | act | cag | gac | aca | acc | tac | 528 |
| Asp | Ala | Val | Ala | Phe | Thr | Cys | Glu | Pro | Glu | Thr | Gln | Asp | Thr | Thr | Tyr | |
| | | | | 165 | | | | | 170 | | | | | 175 | | |
| ctg | tgg | tgg | ata | aac | aat | cag | agc | ctc | ccg | gtc | agt | ccc | agg | ctg | cag | 576 |
| Leu | Trp | Trp | Ile | Asn | Asn | Gln | Ser | Leu | Pro | Val | Ser | Pro | Arg | Leu | Gln | |
| | | | 180 | | | | | 185 | | | | | 190 | | | |
| ctg | tcc | aat | ggc | aac | agg | acc | ctc | act | cta | ctc | agt | gtc | aca | agg | aat | 624 |
| Leu | Ser | Asn | Gly | Asn | Arg | Thr | Leu | Thr | Leu | Leu | Ser | Val | Thr | Arg | Asn | |
| | | 195 | | | | | 200 | | | | | 205 | | | | |
| gac | aca | gga | ccc | tat | gag | tgt | gaa | ata | cag | aac | cca | gtg | agt | gcg | aac | 672 |
| Asp | Thr | Gly | Pro | Tyr | Glu | Cys | Glu | Ile | Gln | Asn | Pro | Val | Ser | Ala | Asn | |
| | 210 | | | | | 215 | | | | | 220 | | | | | |
| cgc | agt | gac | cca | gtc | acc | ttg | aat | gtc | acc | tat | ggc | ccg | gac | acc | ccc | 720 |
| Arg | Ser | Asp | Pro | Val | Thr | Leu | Asn | Val | Thr | Tyr | Gly | Pro | Asp | Thr | Pro | |
| 225 | | | | | 230 | | | | | 235 | | | | | 240 | |
| acc | att | tcc | cct | tca | gac | acc | tat | tac | cgt | cca | ggg | gca | aac | ctc | agc | 768 |
| Thr | Ile | Ser | Pro | Ser | Asp | Thr | Tyr | Tyr | Arg | Pro | Gly | Ala | Asn | Leu | Ser | |
| | | | | 245 | | | | | 250 | | | | | 255 | | |

-continued

| | | |
|---|---|---|
| ctc tcc tgc tat gca gcc tct aac cca cct gca cag tac tcc tgg ctt<br>Leu Ser Cys Tyr Ala Ala Ser Asn Pro Pro Ala Gln Tyr Ser Trp Leu<br>260                           265                         270 | 816 | |
| atc aat gga aca ttc cag caa agc aca caa gag ctc ttt atc cct aac<br>Ile Asn Gly Thr Phe Gln Gln Ser Thr Gln Glu Leu Phe Ile Pro Asn<br>275                         280                         285 | 864 | |
| atc act gtg aat aat agt gga tcc tat acc tgc cac gcc aat aac tca<br>Ile Thr Val Asn Asn Ser Gly Ser Tyr Thr Cys His Ala Asn Asn Ser<br>290                         295                         300 | 912 | |
| gtc act ggc tgc aac agg acc aca gtc aag acg atc ata gtc act gag<br>Val Thr Gly Cys Asn Arg Thr Thr Val Lys Thr Ile Ile Val Thr Glu<br>305                       310                        315                     320 | 960 | |
| cta agt cca gta gta gca aag ccc caa atc aaa gcc agc aag acc aca<br>Leu Ser Pro Val Val Ala Lys Pro Gln Ile Lys Ala Ser Lys Thr Thr<br>                        325                         330                         335 | 1008 | |
| gtc aca gga gat aag gac tct gtg aac ctg acc tgc tcc aca aat gac<br>Val Thr Gly Asp Lys Asp Ser Val Asn Leu Thr Cys Ser Thr Asn Asp<br>                        340                         345                         350 | 1056 | |
| act gga atc tcc atc cgt tgg ttc ttc aaa aac cag agt ctc ccg tcc<br>Thr Gly Ile Ser Ile Arg Trp Phe Phe Lys Asn Gln Ser Leu Pro Ser<br>                 355                         360                         365 | 1104 | |
| tcg gag agg atg aag ctg tcc cag ggc aac acc acc ctc agc ata aac<br>Ser Glu Arg Met Lys Leu Ser Gln Gly Asn Thr Thr Leu Ser Ile Asn<br>370                         375                         380 | 1152 | |
| cct gtc aag agg gag gat gct ggg acg tat tgg tgt gag gtc ttc aac<br>Pro Val Lys Arg Glu Asp Ala Gly Thr Tyr Trp Cys Glu Val Phe Asn<br>385                         390                        395                     400 | 1200 | |
| cca atc agt aag aac caa agc gac ccc atc atg ctg aac gta aac tat<br>Pro Ile Ser Lys Asn Gln Ser Asp Pro Ile Met Leu Asn Val Asn Tyr<br>                        405                         410                         415 | 1248 | |
| aat gct cta cca caa gaa aat ggc ctc tca cct ggg gcc att gct ggc<br>Asn Ala Leu Pro Gln Glu Asn Gly Leu Ser Pro Gly Ala Ile Ala Gly<br>                 420                         425                         430 | 1296 | |
| att gtg att gga gta gtg gcc ctg gtt gct ctg ata gca gta gcc ctg<br>Ile Val Ile Gly Val Val Ala Leu Val Ala Leu Ile Ala Val Ala Leu<br>435                         440                         445 | 1344 | |
| gca tgt ttt ctg cat ttc ggg aag acc ggc agc tca gga cca ctc caa<br>Ala Cys Phe Leu His Phe Gly Lys Thr Gly Ser Ser Gly Pro Leu Gln<br>450                         455                         460 | 1392 | |
| tga | 1395 | |

<210> SEQ ID NO 16
<211> LENGTH: 464
<212> TYPE: PRT
<213> ORGANISM: Homo sapiens

<400> SEQUENCE: 16

Met Gly His Leu Ser Ala Pro Leu His Arg Val Arg Val Pro Trp Gln
1                  5                        10                      15

Gly Leu Leu Leu Thr Ala Ser Leu Leu Thr Phe Trp Asn Pro Pro Thr
                 20                        25                        30

Thr Ala Gln Leu Thr Thr Glu Ser Met Pro Phe Asn Val Ala Glu Gly
                        35                        40                        45

Lys Glu Val Leu Leu Leu Val His Asn Leu Pro Gln Gln Leu Phe Gly
   50                        55                        60

Tyr Ser Trp Tyr Lys Gly Glu Arg Val Asp Gly Asn Arg Gln Ile Val
65                   70                        75                      80

Gly Tyr Ala Ile Gly Thr Gln Gln Ala Thr Pro Gly Pro Ala Asn Ser
                        85                        90                        95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Thr Gln Asp Thr Thr Tyr
                165                 170                 175

Leu Trp Trp Ile Asn Asn Gln Ser Leu Pro Val Ser Pro Arg Leu Gln
            180                 185                 190

Leu Ser Asn Gly Asn Arg Thr Leu Thr Leu Leu Ser Val Thr Arg Asn
        195                 200                 205

Asp Thr Gly Pro Tyr Glu Cys Glu Ile Gln Asn Pro Val Ser Ala Asn
    210                 215                 220

Arg Ser Asp Pro Val Thr Leu Asn Val Thr Tyr Gly Pro Asp Thr Pro
225                 230                 235                 240

Thr Ile Ser Pro Ser Asp Thr Tyr Tyr Arg Pro Gly Ala Asn Leu Ser
                245                 250                 255

Leu Ser Cys Tyr Ala Ala Ser Asn Pro Pro Ala Gln Tyr Ser Trp Leu
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Thr Cys His Ala Asn Asn Ser
    290                 295                 300

Val Thr Gly Cys Asn Arg Thr Thr Val Lys Thr Ile Ile Val Thr Glu
305                 310                 315                 320

Leu Ser Pro Val Val Ala Lys Pro Gln Ile Lys Ala Ser Lys Thr Thr
                325                 330                 335

Val Thr Gly Asp Lys Asp Ser Val Asn Leu Thr Cys Ser Thr Asn Asp
            340                 345                 350

Thr Gly Ile Ser Ile Arg Trp Phe Phe Lys Asn Gln Ser Leu Pro Ser
        355                 360                 365

Ser Glu Arg Met Lys Leu Ser Gln Gly Asn Thr Thr Leu Ser Ile Asn
    370                 375                 380

Pro Val Lys Arg Glu Asp Ala Gly Thr Tyr Trp Cys Glu Val Phe Asn
385                 390                 395                 400

Pro Ile Ser Lys Asn Gln Ser Asp Pro Ile Met Leu Asn Val Asn Tyr
                405                 410                 415

Asn Ala Leu Pro Gln Glu Asn Gly Leu Ser Pro Gly Ala Ile Ala Gly
            420                 425                 430

Ile Val Ile Gly Val Val Ala Leu Val Ala Leu Ile Ala Val Ala Leu
        435                 440                 445

Ala Cys Phe Leu His Phe Gly Lys Thr Gly Ser Ser Gly Pro Leu Gln
    450                 455                 460

<210> SEQ ID NO 17
<211> LENGTH: 1026
<212> TYPE: DNA
<213> ORGANISM: Mus musculus
<220> FEATURE:
<221> NAME/KEY: CDS
<222> LOCATION: (1)..(1026)

```
<400> SEQUENCE: 17 atg gag ctg gcc tca gca cat ctc cac aaa ggg cag gtt ccc tgg gga      48
Met Glu Leu Ala Ser Ala His Leu His Lys Gly Gln Val Pro Trp Gly
  1               5                  10                  15 gga cta ctg ctc aca gcc tca ctt tta gcc tcc tgg agc cct gcc acc      96
Gly Leu Leu Leu Thr Ala Ser Leu Leu Ala Ser Trp Ser Pro Ala Thr
             20                  25                  30 act gct gaa gtc acc gtt gag gct gtg ccg ccc cag gtt gct gaa gac     144
Thr Ala Glu Val Thr Val Glu Ala Val Pro Pro Gln Val Ala Glu Asp
         35                  40                  45 aac aat gtt ctt cta ctt gtt cac aat ctg ccc ctg gcg ctt gga gcc     192
Asn Asn Val Leu Leu Leu Val His Asn Leu Pro Leu Ala Leu Gly Ala
 50                  55                  60 ttt gcc tgg tac aag gga aac act acg gct ata gac aaa gaa att gca     240
Phe Ala Trp Tyr Lys Gly Asn Thr Thr Ala Ile Asp Lys Glu Ile Ala
 65                  70                  75                  80 cga ttt gta cca aat agt aat atg aat ttc acg ggg caa gca tac agc     288
Arg Phe Val Pro Asn Ser Asn Met Asn Phe Thr Gly Gln Ala Tyr Ser
                 85                  90                  95 ggc aga gag ata ata tac agc aat gga tcc ctg ctc ttc caa atg atc     336
Gly Arg Glu Ile Ile Tyr Ser Asn Gly Ser Leu Leu Phe Gln Met Ile
            100                 105                 110 acc atg aag gat atg gga gtc tac aca cta gat atg aca gat gaa aac     384
Thr Met Lys Asp Met Gly Val Tyr Thr Leu Asp Met Thr Asp Glu Asn
        115                 120                 125 tat cgt cgt act cag gcg act gtg cga ttt cat gta cac cag cca gtg     432
Tyr Arg Arg Thr Gln Ala Thr Val Arg Phe His Val His Gln Pro Val
    130                 135                 140 act cag ccc ttc ctc caa gtc acc aac acc aca gtc aaa gaa cta gac     480
Thr Gln Pro Phe Leu Gln Val Thr Asn Thr Thr Val Lys Glu Leu Asp
145                 150                 155                 160 tct gtg acc ctg acc tgc ttg tcg aat gac att gga gcc aac atc cag     528
Ser Val Thr Leu Thr Cys Leu Ser Asn Asp Ile Gly Ala Asn Ile Gln
                165                 170                 175 tgg ctc ttc aat agc cag agt ctt cag ctc aca gag aga atg aca ctc     576
Trp Leu Phe Asn Ser Gln Ser Leu Gln Leu Thr Glu Arg Met Thr Leu
            180                 185                 190 tcc cag aac aac agc atc ctc aga ata gac cct att aag agg gaa gat     624
Ser Gln Asn Asn Ser Ile Leu Arg Ile Asp Pro Ile Lys Arg Glu Asp
        195                 200                 205 gcc ggc gag tat cag tgt gag atc tcg aat cca gtc agc gtc agg agg     672
Ala Gly Glu Tyr Gln Cys Glu Ile Ser Asn Pro Val Ser Val Arg Arg
    210                 215                 220 agc aac tca atc aag ctg gac ata ata ttt gac cca aca caa gga ggc     720
Ser Asn Ser Ile Lys Leu Asp Ile Ile Phe Asp Pro Thr Gln Gly Gly
225                 230                 235                 240 ctc tca gat ggc gcc att gct ggc atc gtg att gga gtt gtg gct ggg     768
Leu Ser Asp Gly Ala Ile Ala Gly Ile Val Ile Gly Val Val Ala Gly
                245                 250                 255 gtg gct cta ata gca ggg ctg gca tat ttc ctc tat tcc agg aag tct     816
Val Ala Leu Ile Ala Gly Leu Ala Tyr Phe Leu Tyr Ser Arg Lys Ser
            260                 265                 270 ggc ggg gga ggt gac cag cga gat ctc aca gag cac aaa ccc tca gcc     864
Gly Gly Gly Gly Asp Gln Arg Asp Leu Thr Glu His Lys Pro Ser Ala
        275                 280                 285 tcc aac cac aat ctg gct cct tct gac aac tct cct aac aag gtg gat     912
Ser Asn His Asn Leu Ala Pro Ser Asp Asn Ser Pro Asn Lys Val Asp
    290                 295                 300 gac gtc gca tac act gtc ctg aac ttc aat tcc cag caa ccc aac cgg     960
```

```
Asp Val Ala Tyr Thr Val Leu Asn Phe Asn Ser Gln Gln Pro Asn Arg
305                 310                 315                 320 cca act tca gcc cct tct tct cca aga gcc aca gaa aca gtt tat tca        1008
Pro Thr Ser Ala Pro Ser Ser Pro Arg Ala Thr Glu Thr Val Tyr Ser
                325                 330                 335 gaa gta aaa aag aag tga                                                1026
Glu Val Lys Lys Lys
            340

<210> SEQ ID NO 18
<211> LENGTH: 341
<212> TYPE: PRT
<213> ORGANISM: Mus musculus

<400> SEQUENCE: 18

Met Glu Leu Ala Ser Ala His Leu His Lys Gly Gln Val Pro Trp Gly
1               5                   10                  15

Gly Leu Leu Leu Thr Ala Ser Leu Leu Ala Ser Trp Ser Pro Ala Thr
                20                  25                  30

Thr Ala Glu Val Thr Val Glu Ala Val Pro Pro Gln Val Ala Glu Asp
            35                  40                  45

Asn Asn Val Leu Leu Val His Asn Leu Pro Leu Ala Leu Gly Ala
50                  55                  60

Phe Ala Trp Tyr Lys Gly Asn Thr Thr Ala Ile Asp Lys Glu Ile Ala
65                  70                  75                  80

Arg Phe Val Pro Asn Ser Asn Met Asn Phe Thr Gly Gln Ala Tyr Ser
                85                  90                  95

Gly Arg Glu Ile Ile Tyr Ser Asn Gly Ser Leu Leu Phe Gln Met Ile
                100                 105                 110

Thr Met Lys Asp Met Gly Val Tyr Thr Leu Asp Met Thr Asp Glu Asn
            115                 120                 125

Tyr Arg Arg Thr Gln Ala Thr Val Arg Phe His Val His Gln Pro Val
130                 135                 140

Thr Gln Pro Phe Leu Gln Val Thr Asn Thr Thr Val Lys Glu Leu Asp
145                 150                 155                 160

Ser Val Thr Leu Thr Cys Leu Ser Asn Asp Ile Gly Ala Asn Ile Gln
                165                 170                 175

Trp Leu Phe Asn Ser Gln Ser Leu Gln Leu Thr Glu Arg Met Thr Leu
            180                 185                 190

Ser Gln Asn Asn Ser Ile Leu Arg Ile Asp Pro Ile Lys Arg Glu Asp
            195                 200                 205

Ala Gly Glu Tyr Gln Cys Glu Ile Ser Asn Pro Val Ser Val Arg Arg
        210                 215                 220

Ser Asn Ser Ile Lys Leu Asp Ile Ile Phe Asp Pro Thr Gln Gly Gly
225                 230                 235                 240

Leu Ser Asp Gly Ala Ile Ala Gly Ile Val Ile Gly Val Val Ala Gly
                245                 250                 255

Val Ala Leu Ile Ala Gly Leu Ala Tyr Phe Leu Tyr Ser Arg Lys Ser
                260                 265                 270

Gly Gly Gly Gly Asp Gln Arg Asp Leu Thr Glu His Lys Pro Ser Ala
            275                 280                 285

Ser Asn His Asn Leu Ala Pro Ser Asp Asn Ser Pro Asn Lys Val Asp
        290                 295                 300

Asp Val Ala Tyr Thr Val Leu Asn Phe Asn Ser Gln Gln Pro Asn Arg
305                 310                 315                 320
```

```
Pro Thr Ser Ala Pro Ser Ser Pro Arg Ala Thr Glu Thr Val Tyr Ser
            325                 330                 335

Glu Val Lys Lys Lys
        340

<210> SEQ ID NO 19
<211> LENGTH: 837
<212> TYPE: DNA
<213> ORGANISM: Mus musculus
<220> FEATURE:
<221> NAME/KEY: CDS
<222> LOCATION: (1)..(837)

<400> SEQUENCE: 19 atg gag ctg gcc tca gca cat ctc cac aaa ggg cag gtt ccc tgg gga       48
Met Glu Leu Ala Ser Ala His Leu His Lys Gly Gln Val Pro Trp Gly
1               5                   10                  15 gga cta ctg ctc aca gcc tca ctt tta gcc tcc tgg agc cct gcc acc       96
Gly Leu Leu Leu Thr Ala Ser Leu Leu Ala Ser Trp Ser Pro Ala Thr
            20                  25                  30 act gct gaa gtc acc att gag gct gtg ccg ccc cag gtt gct gaa gac      144
Thr Ala Glu Val Thr Ile Glu Ala Val Pro Pro Gln Val Ala Glu Asp
        35                  40                  45 aac aat gtt ctt cta ctt gtt cac aat ctg ccc ctg gcg ctt gga gcc      192
Asn Asn Val Leu Leu Leu Val His Asn Leu Pro Leu Ala Leu Gly Ala
    50                  55                  60 ttt gcc tgg tac aag gga aac act acg gct ata gac aaa gaa att gca      240
Phe Ala Trp Tyr Lys Gly Asn Thr Thr Ala Ile Asp Lys Glu Ile Ala
65                  70                  75                  80 cga ttt gta cca aat agt aat atg aat ttc acg ggg caa gca tac agc      288
Arg Phe Val Pro Asn Ser Asn Met Asn Phe Thr Gly Gln Ala Tyr Ser
                85                  90                  95 ggc aga gag ata ata tac agc aat gga tcc ctg ctc ttc caa atg atc      336
Gly Arg Glu Ile Ile Tyr Ser Asn Gly Ser Leu Leu Phe Gln Met Ile
            100                 105                 110 acc atg aag gat atg gga gtc tac aca cta gat atg aca gat gaa aac      384
Thr Met Lys Asp Met Gly Val Tyr Thr Leu Asp Met Thr Asp Glu Asn
        115                 120                 125 tat cgt cgt act cag gcg act gtg cga ttt cat gta cac cag cca gtg      432
Tyr Arg Arg Thr Gln Ala Thr Val Arg Phe His Val His Gln Pro Val
    130                 135                 140 act cag ccc ttc ctc caa gtc acc aac acc aca gtc aaa gaa cta gac      480
Thr Gln Pro Phe Leu Gln Val Thr Asn Thr Thr Val Lys Glu Leu Asp
145                 150                 155                 160 tct gtg acc ctg acc tgc ttg tcg aat gac att gga gcc aac atc cag      528
Ser Val Thr Leu Thr Cys Leu Ser Asn Asp Ile Gly Ala Asn Ile Gln
                165                 170                 175 tgg ctc ttc aat agc cag agt ctt cag ctc aca gag aga atg aca ctc      576
Trp Leu Phe Asn Ser Gln Ser Leu Gln Leu Thr Glu Arg Met Thr Leu
            180                 185                 190 tcc cag aac aac agc atc ctc aga ata gac cct att aag agg gaa gat      624
Ser Gln Asn Asn Ser Ile Leu Arg Ile Asp Pro Ile Lys Arg Glu Asp
        195                 200                 205 gcc ggc gag tat cag tgt gaa atc tcg aat cca gtc agc gtc agg agg      672
Ala Gly Glu Tyr Gln Cys Glu Ile Ser Asn Pro Val Ser Val Arg Arg
    210                 215                 220 agc aac tca atc aag ctg gac ata ata ttt gac cca aca caa gga ggc      720
Ser Asn Ser Ile Lys Leu Asp Ile Ile Phe Asp Pro Thr Gln Gly Gly
225                 230                 235                 240 ctc tca gat ggc gcc att gct ggc atc gtg att gga gtt gtg gct ggg      768
Leu Ser Asp Gly Ala Ile Ala Gly Ile Val Ile Gly Val Val Ala Gly
```

```
                    245                 250                 255
gtg gct cta ata gca ggg ctg gca tat ttc ctc tat tcc agg aag tct      816
Val Ala Leu Ile Ala Gly Leu Ala Tyr Phe Leu Tyr Ser Arg Lys Ser
            260                 265                 270 ggc gga tct ggc tcc ttc tga                                          837
Gly Gly Ser Gly Ser Phe
        275

<210> SEQ ID NO 20
<211> LENGTH: 278
<212> TYPE: PRT
<213> ORGANISM: Mus musculus

<400> SEQUENCE: 20

Met Glu Leu Ala Ser Ala His Leu His Lys Gly Gln Val Pro Trp Gly
1               5                   10                  15

Gly Leu Leu Leu Thr Ala Ser Leu Leu Ala Ser Trp Ser Pro Ala Thr
            20                  25                  30

Thr Ala Glu Val Thr Ile Glu Ala Val Pro Pro Gln Val Ala Glu Asp
        35                  40                  45

Asn Asn Val Leu Leu Val His Asn Leu Pro Leu Ala Leu Gly Ala
    50                  55                  60

Phe Ala Trp Tyr Lys Gly Asn Thr Thr Ala Ile Asp Lys Glu Ile Ala
65                  70                  75                  80

Arg Phe Val Pro Asn Ser Asn Met Asn Phe Thr Gly Gln Ala Tyr Ser
                85                  90                  95

Gly Arg Glu Ile Ile Tyr Ser Asn Gly Ser Leu Leu Phe Gln Met Ile
            100                 105                 110

Thr Met Lys Asp Met Gly Val Tyr Thr Leu Asp Met Thr Asp Glu Asn
        115                 120                 125

Tyr Arg Arg Thr Gln Ala Thr Val Arg Phe His Val His Gln Pro Val
    130                 135                 140

Thr Gln Pro Phe Leu Gln Val Thr Asn Thr Thr Val Lys Glu Leu Asp
145                 150                 155                 160

Ser Val Thr Leu Thr Cys Leu Ser Asn Asp Ile Gly Ala Asn Ile Gln
                165                 170                 175

Trp Leu Phe Asn Ser Gln Ser Leu Gln Leu Thr Glu Arg Met Thr Leu
            180                 185                 190

Ser Gln Asn Asn Ser Ile Leu Arg Ile Asp Pro Ile Lys Arg Glu Asp
        195                 200                 205

Ala Gly Glu Tyr Gln Cys Glu Ile Ser Asn Pro Val Ser Val Arg Arg
    210                 215                 220

Ser Asn Ser Ile Lys Leu Asp Ile Ile Phe Asp Pro Thr Gln Gly Gly
225                 230                 235                 240

Leu Ser Asp Gly Ala Ile Ala Gly Ile Val Ile Gly Val Val Ala Gly
                245                 250                 255

Val Ala Leu Ile Ala Gly Leu Ala Tyr Phe Leu Tyr Ser Arg Lys Ser
            260                 265                 270

Gly Gly Ser Gly Ser Phe
        275

<210> SEQ ID NO 21
<211> LENGTH: 1035
<212> TYPE: DNA
<213> ORGANISM: Homo sapiens
<220> FEATURE:
<221> NAME/KEY: CDS
```

<222> LOCATION: (1)..(1035)

<400> SEQUENCE: 21

| | | | | | | | | | | | | | | | | |
|---|---|---|---|---|---|---|---|---|---|---|---|---|---|---|---|---|
| atg | gga | ccc | ccc | tca | gcc | cct | ccc | tgc | aga | ttg | cat | gtc | ccc | tgg | aag | 48 |
| Met | Gly | Pro | Pro | Ser | Ala | Pro | Pro | Cys | Arg | Leu | His | Val | Pro | Trp | Lys | |
| 1 | | | | 5 | | | | | 10 | | | | | 15 | | |
| gag | gtc | ctg | ctc | aca | gcc | tca | ctt | cta | acc | ttc | tgg | aac | cca | ccc | acc | 96 |
| Glu | Val | Leu | Leu | Thr | Ala | Ser | Leu | Leu | Thr | Phe | Trp | Asn | Pro | Pro | Thr | |
| | | | 20 | | | | | 25 | | | | | 30 | | | |
| act | gcc | aag | ctc | act | att | gaa | tcc | acg | ccg | ttc | aat | gtc | gca | gag | ggg | 144 |
| Thr | Ala | Lys | Leu | Thr | Ile | Glu | Ser | Thr | Pro | Phe | Asn | Val | Ala | Glu | Gly | |
| | | 35 | | | | | 40 | | | | | 45 | | | | |
| aag | gag | gtt | ctt | cta | ctc | gcc | cac | aac | ctg | ccc | cag | aat | cgt | att | ggt | 192 |
| Lys | Glu | Val | Leu | Leu | Leu | Ala | His | Asn | Leu | Pro | Gln | Asn | Arg | Ile | Gly | |
| | 50 | | | | | 55 | | | | | 60 | | | | | |
| tac | agc | tgg | tac | aaa | ggc | gaa | aga | gtg | gat | ggc | aac | agt | cta | att | gta | 240 |
| Tyr | Ser | Trp | Tyr | Lys | Gly | Glu | Arg | Val | Asp | Gly | Asn | Ser | Leu | Ile | Val | |
| 65 | | | | | 70 | | | | | 75 | | | | | 80 | |
| gga | tat | gta | ata | gga | act | caa | caa | gct | acc | cca | ggg | ccc | gca | tac | agt | 288 |
| Gly | Tyr | Val | Ile | Gly | Thr | Gln | Gln | Ala | Thr | Pro | Gly | Pro | Ala | Tyr | Ser | |
| | | | | 85 | | | | | 90 | | | | | 95 | | |
| ggt | cga | gag | aca | ata | tac | ccc | aat | gca | tcc | ctg | ctg | atc | cag | aac | gtc | 336 |
| Gly | Arg | Glu | Thr | Ile | Tyr | Pro | Asn | Ala | Ser | Leu | Leu | Ile | Gln | Asn | Val | |
| | | | 100 | | | | | 105 | | | | | 110 | | | |
| acc | cag | aat | gac | aca | gga | ttc | tat | acc | cta | caa | gtc | ata | aag | tca | gat | 384 |
| Thr | Gln | Asn | Asp | Thr | Gly | Phe | Tyr | Thr | Leu | Gln | Val | Ile | Lys | Ser | Asp | |
| | | 115 | | | | | 120 | | | | | 125 | | | | |
| ctt | gtg | aat | gaa | gaa | gca | acc | gga | cag | ttc | cat | gta | tac | ccg | gag | ctg | 432 |
| Leu | Val | Asn | Glu | Glu | Ala | Thr | Gly | Gln | Phe | His | Val | Tyr | Pro | Glu | Leu | |
| | 130 | | | | | 135 | | | | | 140 | | | | | |
| ccc | aag | ccc | tcc | atc | tcc | agc | aac | aac | tcc | aac | ccc | gtg | gag | gac | aag | 480 |
| Pro | Lys | Pro | Ser | Ile | Ser | Ser | Asn | Asn | Ser | Asn | Pro | Val | Glu | Asp | Lys | |
| 145 | | | | | 150 | | | | | 155 | | | | | 160 | |
| gat | gct | gtg | gcc | ttc | acc | tgt | gaa | cct | gag | gtt | cag | aac | aca | acc | tac | 528 |
| Asp | Ala | Val | Ala | Phe | Thr | Cys | Glu | Pro | Glu | Val | Gln | Asn | Thr | Thr | Tyr | |
| | | | | 165 | | | | | 170 | | | | | 175 | | |
| ctg | tgg | tgg | gta | aat | ggt | cag | agc | ctc | ccg | gtc | agt | ccc | agg | ctg | cag | 576 |
| Leu | Trp | Trp | Val | Asn | Gly | Gln | Ser | Leu | Pro | Val | Ser | Pro | Arg | Leu | Gln | |
| | | | 180 | | | | | 185 | | | | | 190 | | | |
| ctg | tcc | aat | ggc | aac | atg | acc | ctc | act | cta | ctc | agc | gtc | aaa | agg | aac | 624 |
| Leu | Ser | Asn | Gly | Asn | Met | Thr | Leu | Thr | Leu | Leu | Ser | Val | Lys | Arg | Asn | |
| | | 195 | | | | | 200 | | | | | 205 | | | | |
| gat | gca | gga | tcc | tat | gaa | tgt | gaa | ata | cag | aac | cca | gcg | agt | gcc | aac | 672 |
| Asp | Ala | Gly | Ser | Tyr | Glu | Cys | Glu | Ile | Gln | Asn | Pro | Ala | Ser | Ala | Asn | |
| | 210 | | | | | 215 | | | | | 220 | | | | | |
| cgc | agt | gac | cca | gtc | acc | ctg | aat | gtc | ctc | tat | ggc | cca | gat | ggc | ccc | 720 |
| Arg | Ser | Asp | Pro | Val | Thr | Leu | Asn | Val | Leu | Tyr | Gly | Pro | Asp | Gly | Pro | |
| 225 | | | | | 230 | | | | | 235 | | | | | 240 | |
| acc | att | tcc | ccc | tca | aag | gcc | aat | tac | cgt | cca | ggg | gaa | aat | ctg | aac | 768 |
| Thr | Ile | Ser | Pro | Ser | Lys | Ala | Asn | Tyr | Arg | Pro | Gly | Glu | Asn | Leu | Asn | |
| | | | | 245 | | | | | 250 | | | | | 255 | | |
| ctc | tcc | tgc | cac | gca | gcc | tct | aac | cca | cct | gca | cag | tac | tct | tgg | ttt | 816 |
| Leu | Ser | Cys | His | Ala | Ala | Ser | Asn | Pro | Pro | Ala | Gln | Tyr | Ser | Trp | Phe | |
| | | | 260 | | | | | 265 | | | | | 270 | | | |
| atc | aat | ggg | acg | ttc | cag | caa | tcc | aca | caa | gag | ctc | ttt | atc | ccc | aac | 864 |
| Ile | Asn | Gly | Thr | Phe | Gln | Gln | Ser | Thr | Gln | Glu | Leu | Phe | Ile | Pro | Asn | |
| | | 275 | | | | | 280 | | | | | 285 | | | | |
| atc | act | gtg | aat | aat | agc | gga | tcc | tat | atg | tgc | caa | gcc | cat | aac | tca | 912 |
| Ile | Thr | Val | Asn | Asn | Ser | Gly | Ser | Tyr | Met | Cys | Gln | Ala | His | Asn | Ser | |
| | 290 | | | | | 295 | | | | | 300 | | | | | |

```
gcc act ggc ctc aat agg acc aca gtc acg atg atc aca gtc tct gga       960
Ala Thr Gly Leu Asn Arg Thr Thr Val Thr Met Ile Thr Val Ser Gly
305                 310                 315                 320 agt gct cct gtc ctc tca gct gtg gcc acc gtc ggc atc acg att gga      1008
Ser Ala Pro Val Leu Ser Ala Val Ala Thr Val Gly Ile Thr Ile Gly
            325                 330                 335 gtg ctg gcc agg gtg gct ctg ata tag                                   1035
Val Leu Ala Arg Val Ala Leu Ile
            340
```

<210> SEQ ID NO 22
<211> LENGTH: 344
<212> TYPE: PRT
<213> ORGANISM: Homo sapiens

<400> SEQUENCE: 22

```
Met Gly Pro Pro Ser Ala Pro Pro Cys Arg Leu His Val Pro Trp Lys
1               5                   10                  15

Glu Val Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Ala His Asn Leu Pro Gln Asn Arg Ile Gly
    50                  55                  60

Tyr Ser Trp Tyr Lys Gly Glu Arg Val Asp Gly Asn Ser Leu Ile Val
65                  70                  75                  80

Gly Tyr Val Ile Gly Thr Gln Gln Ala Thr Pro Gly Pro Ala Tyr Ser
                85                  90                  95

Gly Arg Glu Thr Ile Tyr Pro Asn Ala Ser Leu Leu Ile Gln Asn Val
            100                 105                 110

Thr Gln Asn Asp Thr Gly Phe Tyr Thr Leu Gln Val Ile Lys Ser Asp
        115                 120                 125

Leu Val Asn Glu Glu Ala Thr Gly Gln Phe His Val Tyr Pro Glu Leu
    130                 135                 140

Pro Lys Pro Ser Ile Ser Ser Asn Asn Ser Asn Pro Val Glu Asp Lys
145                 150                 155                 160

Asp Ala Val Ala Phe Thr Cys Glu Pro Glu Val Gln Asn Thr Thr Tyr
                165                 170                 175

Leu Trp Trp Val Asn Gly Gln Ser Leu Pro Val Ser Pro Arg Leu Gln
            180                 185                 190

Leu Ser Asn Gly Asn Met Thr Leu Thr Leu Leu Ser Val Lys Arg Asn
        195                 200                 205

Asp Ala Gly Ser Tyr Glu Cys Glu Ile Gln Asn Pro Ala Ser Ala Asn
    210                 215                 220

Arg Ser Asp Pro Val Thr Leu Asn Val Leu Tyr Gly Pro Asp Gly Pro
225                 230                 235                 240

Thr Ile Ser Pro Ser Lys Ala Asn Tyr Arg Pro Gly Glu Asn Leu Asn
                245                 250                 255

Leu Ser Cys His Ala Ala Ser Asn Pro Pro Ala Gln Tyr Ser Trp Phe
            260                 265                 270

Ile Asn Gly Thr Phe Gln Gln Ser Thr Gln Glu Leu Phe Ile Pro Asn
        275                 280                 285

Ile Thr Val Asn Asn Ser Gly Ser Tyr Met Cys Gln Ala His Asn Ser
    290                 295                 300

Ala Thr Gly Leu Asn Arg Thr Thr Val Thr Met Ile Thr Val Ser Gly
```

```
            305                 310                 315                 320
Ser Ala Pro Val Leu Ser Ala Val Ala Thr Val Gly Ile Thr Ile Gly
                325                 330                 335
Val Leu Ala Arg Val Ala Leu Ile
            340
```

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 23
atcctcccaa gagctcttta tc                                              22

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 24
tttgtgctct gtgagatctc g                                               21

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 25
acaccatggg gcacctctca                                                 20

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 26
gatcgtcttg actgtggtcc t                                               21

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 27
actctgtgaa cctgacctgc t                                               21

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 28
ttactgcttt tttacttctg aata                                            24

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 29
actctgtgaa cctgacctgc t                                         21

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 30
ggtcctgagc tgccggtctt                                           20

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 31
caacatccag tggctcttca a                                         21

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 32
cttctttttt acttctgaat aaac                                      24

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 33
caacatccag tggctcttca a                                         21

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 34
tcagaaggag ccagatccgc                                           20

<210> SEQ ID NO 35
<211> LENGTH: 20
<212> TYPE: DNA
<213> ORGANISM: Artificial Sequence
<220> FEATURE:

<223> OTHER INFORMATION: Synthetic oligonucleotide primer

<400> SEQUENCE: 35
ctcacgggga gaagcgtctc                                               20

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 36
tggcacttgc atggagtttt c                                             21

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 37
agcaggagat tgctgagatc                                               20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 38
gcaccacaga gatgttgact                                               20

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 39
atgggcttcc tgaagttctc c                                             21

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 40
cttagatctg gggctgtcca                                               20

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 41
atgggcttcc aaaagttctc c                                             21

```
<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 42
cttagatctg gggctgtcca                                              20

<210> SEQ ID NO 43
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 43
ttctttcctt ttctggctct ca                                           22

<210> SEQ ID NO 44
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 44
tcaggcctgc aggtccctg                                               19

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 45
atgggtttcc ggaagttctc c                                            21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 46
acattggtgg gcacgaagtt g                                            21

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 47
ttttgcatgc ctggaaaact cc                                           22

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide primer
```

```
<400> SEQUENCE: 48
gtctgtctgc aggatgtgga a                                              21

<210> SEQ ID NO 49
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 49
tatgtaccat cccatctcta tc                                             22

<210> SEQ ID NO 50
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 50
gacagagcct taatgtagat aac                                            23

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 51
aagaaggaag gggccaagct                                                20

<210> SEQ ID NO 52
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 52
tggtgacagt tttcacttct gt                                             22

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 53
gcggacgaga atggaaactt g                                              21

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 54
agtccttcaa tgatgctcag at                                             22

<210> SEQ ID NO 55
<211> LENGTH: 20
```

```
<212> TYPE: DNA
<213> ORGANISM: Artificial Sequence
<220> FEATURE:
<223> OTHER INFORMATION: Synthetic oligonucleotide primer

<400> SEQUENCE: 55
gaccctggtg ctatgtgcag                                                20

<210> SEQ ID NO 56
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 56
ccaaagccag tgatctcaca g                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 57
ggcttagagg tgactggcaa a                                              21

<210> SEQ ID NO 58
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 58
gtccaggttt catcatcatc aaa                                            23

<210> SEQ ID NO 59
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 59
catcctttta aaatgaagtg gca                                            23

<210> SEQ ID NO 60
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 60
ttcttcttcc tggctatttt gg                                             22

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 61
```
aacccggcca gcatttcaga                                        20

<210> SEQ ID NO 62
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 62
ccaagttcac gtgcataaca c                                      21

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 63
cgcatctcag aggccaagct                                        20

<210> SEQ ID NO 64
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 64
gttgttgaag aggctgatgc c                                      21

<210> SEQ ID NO 65
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 65
gcttctctaa agaagtcagg aaa                                    23

<210> SEQ ID NO 66
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 66
gacaaaccgg ttggcagagg                                        20

<210> SEQ ID NO 67
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 67
gtccatgtgg gagattgtga c                                      21

<210> SEQ ID NO 68
<211> LENGTH: 20
<212> TYPE: DNA
<213> ORGANISM: Artificial Sequence

```
<220> FEATURE:
<223> OTHER INFORMATION: Synthetic oligonucleotide primer

<400> SEQUENCE: 68
tcagtcctca gccccctctt                                                   20

<210> SEQ ID NO 69
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 69
atggaagaag ggagtgatga c                                                 21

<210> SEQ ID NO 70
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 70
gtgtccttgc tggtgtagtg                                                   20

<210> SEQ ID NO 71
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 71
agaattcgcc accatggagc tggcctcagc aca                                    33

<210> SEQ ID NO 72
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 72
actcgagctt cttttttact tctgaata                                          28

<210> SEQ ID NO 73
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 73
agctagcgcc accatggggc acctctcagc ccc                                    33

<210> SEQ ID NO 74
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 74
actcgagctg cttttttact tctgaata                                          28
```

```
<210> SEQ ID NO 75
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 75
gggaaacact acggctatag a                                        21

<210> SEQ ID NO 76
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 76
ggatggcaac cgtcaaattg t                                        21

<210> SEQ ID NO 77
<211> LENGTH: 8
<212> TYPE: PRT
<213> ORGANISM: Artificial Sequence
<220> FEATURE:
<223> OTHER INFORMATION: Synthetic peptide

<400> SEQUENCE: 77

Asp Tyr Lys Asp Asp Asp Asp Lys
1               5
```